(12) United States Patent
Chen

(10) Patent No.: US 10,441,169 B2
(45) Date of Patent: Oct. 15, 2019

(54) NANO-BIOMIMETIC MEMS-TRANSFORMER DEVICES OF MAKING AND AN APPLICATION IN ENERGY-SENSORY IMAGES THERETO

(71) Applicant: Ellen T Chen, Rockville, MD (US)

(72) Inventor: Ellen T Chen, Rockville, MD (US)

( * ) Notice: Subject to any disclaimer, the term of this patent is extended or adjusted under 35 U.S.C. 154(b) by 0 days.

(21) Appl. No.: 15/361,068

(22) Filed: Nov. 24, 2016

(65) Prior Publication Data
US 2018/0144238 A1    May 24, 2018

(51) Int. Cl.
*A61B 5/00* (2006.01)
*G01R 33/48* (2006.01)

(52) U.S. Cl.
CPC ........ *A61B 5/00* (2013.01); *G01N 2333/4709* (2013.01); *G01R 33/4806* (2013.01)

(58) Field of Classification Search
CPC .... G06N 3/04; A61B 5/00; G01N 2333/4709; G01R 33/4806
See application file for complete search history.

(56) References Cited

U.S. PATENT DOCUMENTS

| | | | |
|---|---|---|---|
| 8,083,926 B2 * | 12/2011 | Chen ....................... | C12Q 1/006 204/403.01 |
| 8,641,876 B2 * | 2/2014 | Chen ..................... | G01N 33/548 204/403.01 |
| 9,793,503 B2 * | 10/2017 | Chen ..................... | H01L 51/0591 |
| 9,950,002 B2 * | 4/2018 | Kandimalla ....... | A61K 49/1863 |
| 2007/0238184 A1 * | 10/2007 | Lal .......................... | B01J 20/205 436/86 |
| 2014/0011691 A1 * | 1/2014 | Sierks ................ | G01N 33/5438 506/9 |
| 2016/0282338 A1 * | 9/2016 | Miklas ................... | C12M 21/08 |
| 2018/0088069 A1 * | 3/2018 | Chen ...................... | G01N 27/27 |

* cited by examiner

*Primary Examiner* — Michael C Zarroli

(57) ABSTRACT

An electromagnetic mems-transformer includes arrays of nanostructured first toroid winding by a self-assembled organic conductive membrane on an electrode, and a second toroid winding with "donut" shape cyclodextrins (CDs) comprising of different electronegativity functional groups was inserted in the first toroid; a hydrophobic laminate agent forms a linen lining the first cavity of the toroid in perpendicular to the first and second toroid with air gaps for adjusting, upon applying a DC potential crosses two electrodes in a fluid medium for initiation of the device, a changing current flows until reached the s-s state in a nano Ampere level. When held the nano Ampere current in constant for spontaneous discharge voltage pulses, the current induced an electromagnetic flux change with orders of magnitude higher output voltage produced compared with the initiation potential. Embedded on-off switches promoted hysteresis i-V curves for memory function. Applications in sensing neuronal dysfunctions in an Energy-Sensory Image were demonstrated.

21 Claims, 77 Drawing Sheets

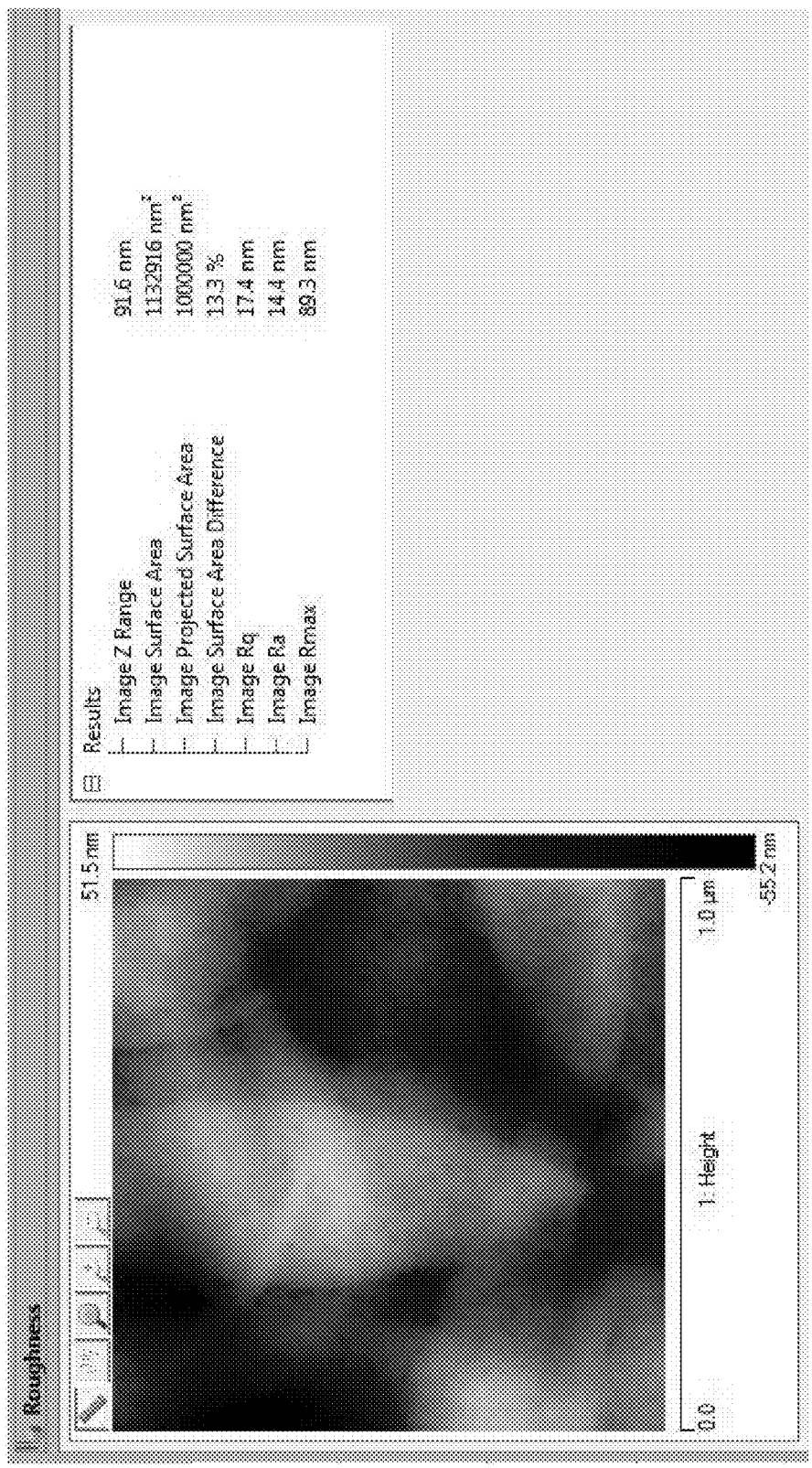

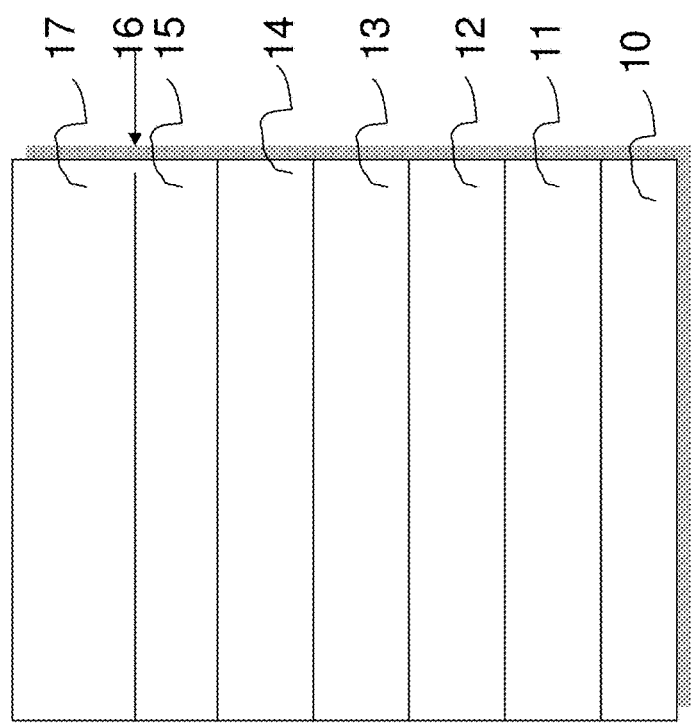

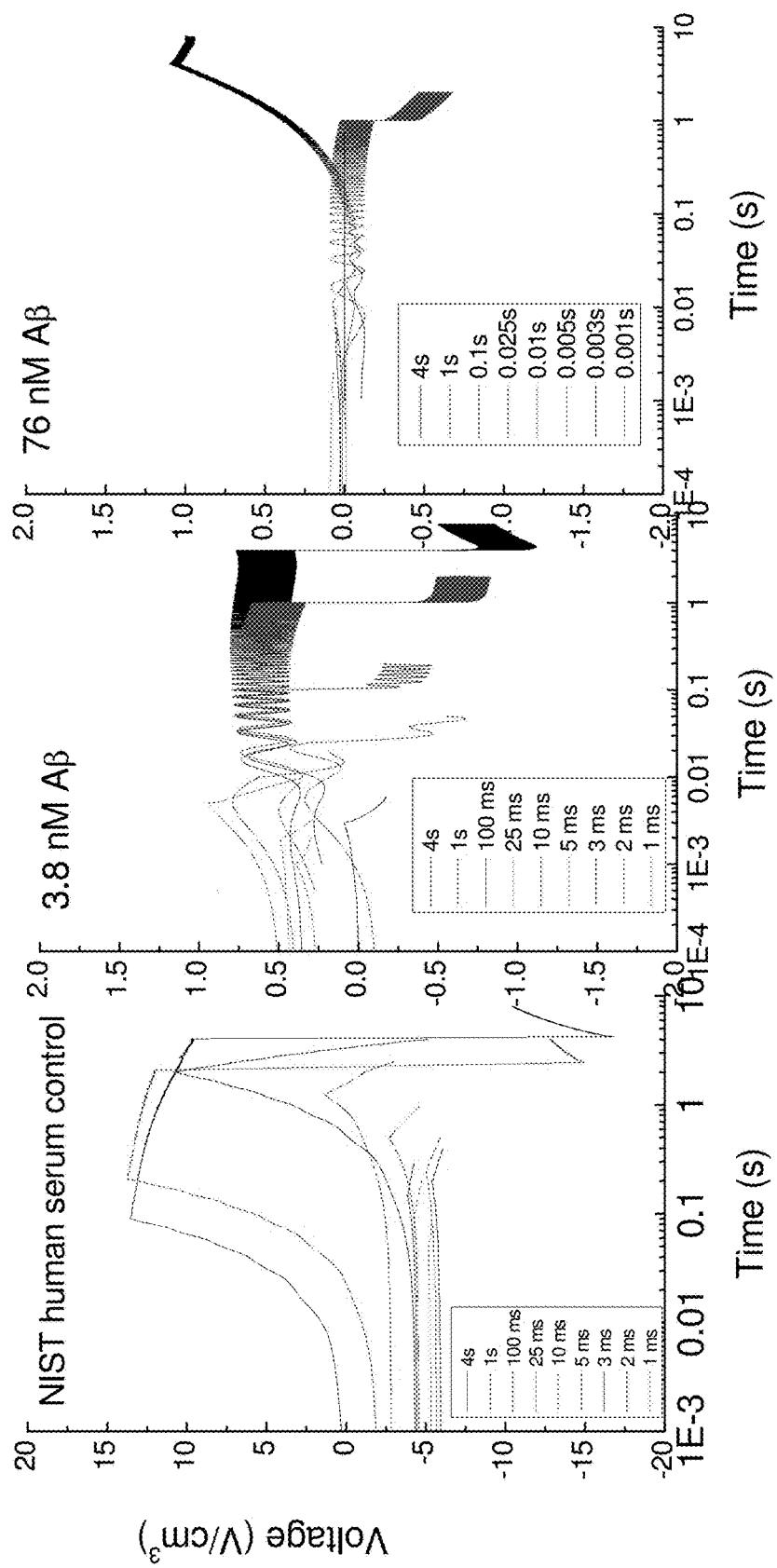
Fig. 11A₁ Fig. 11A₂ Fig. 11A₃

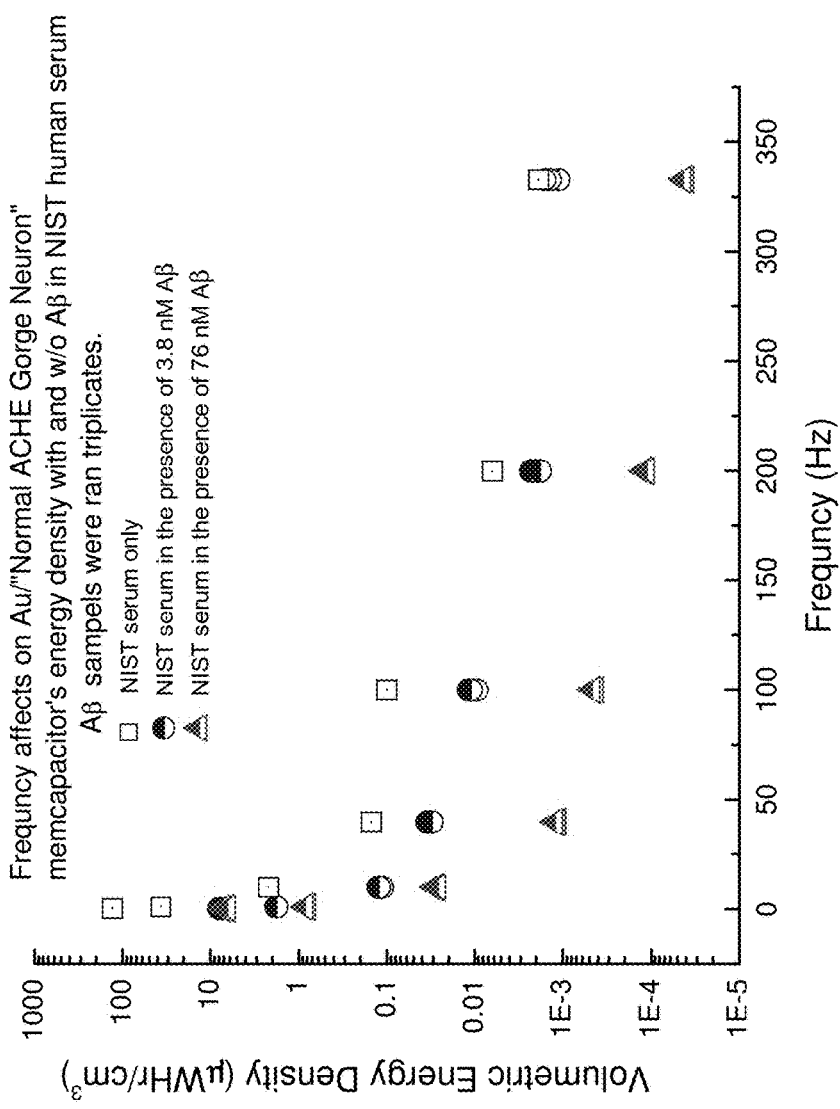

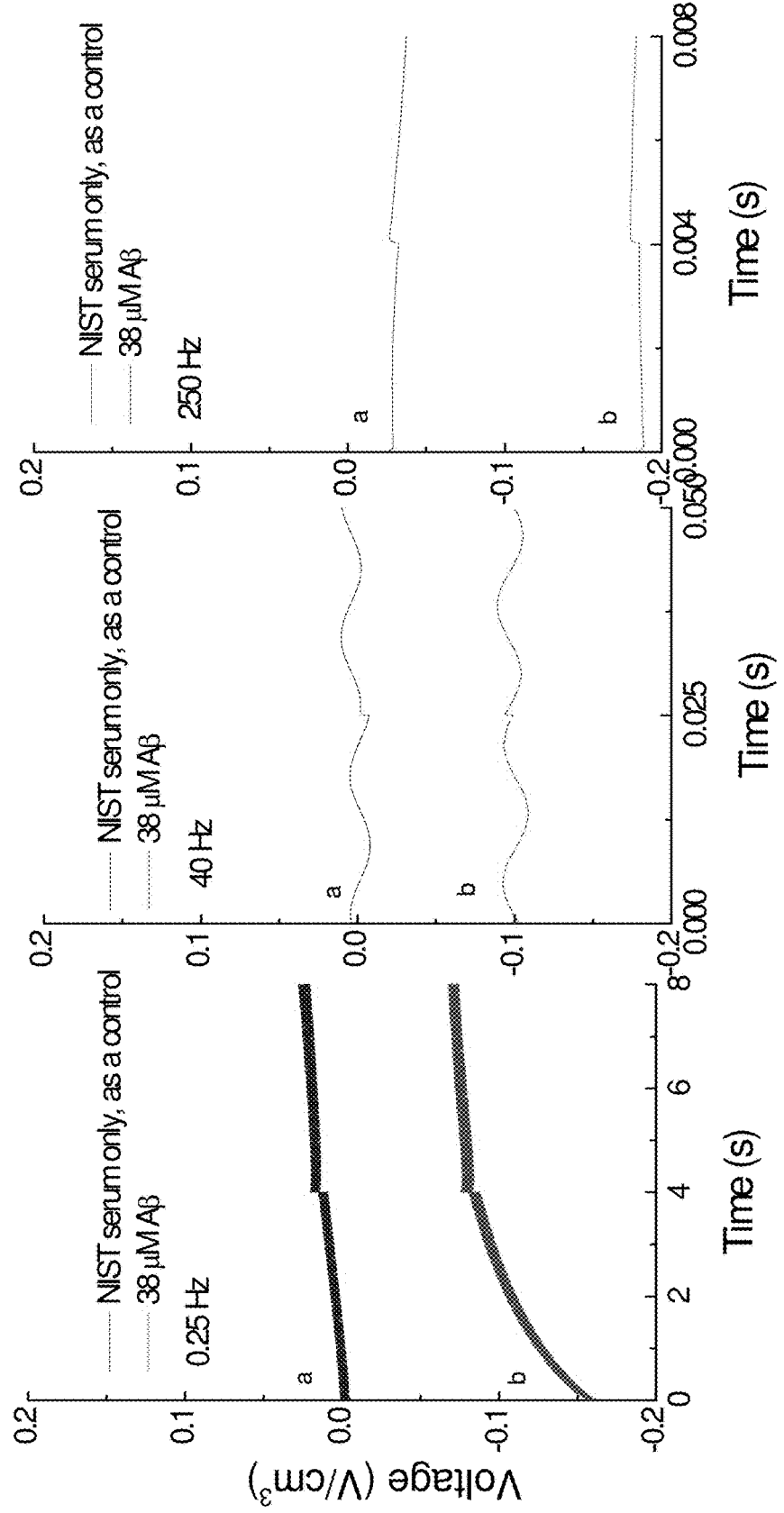

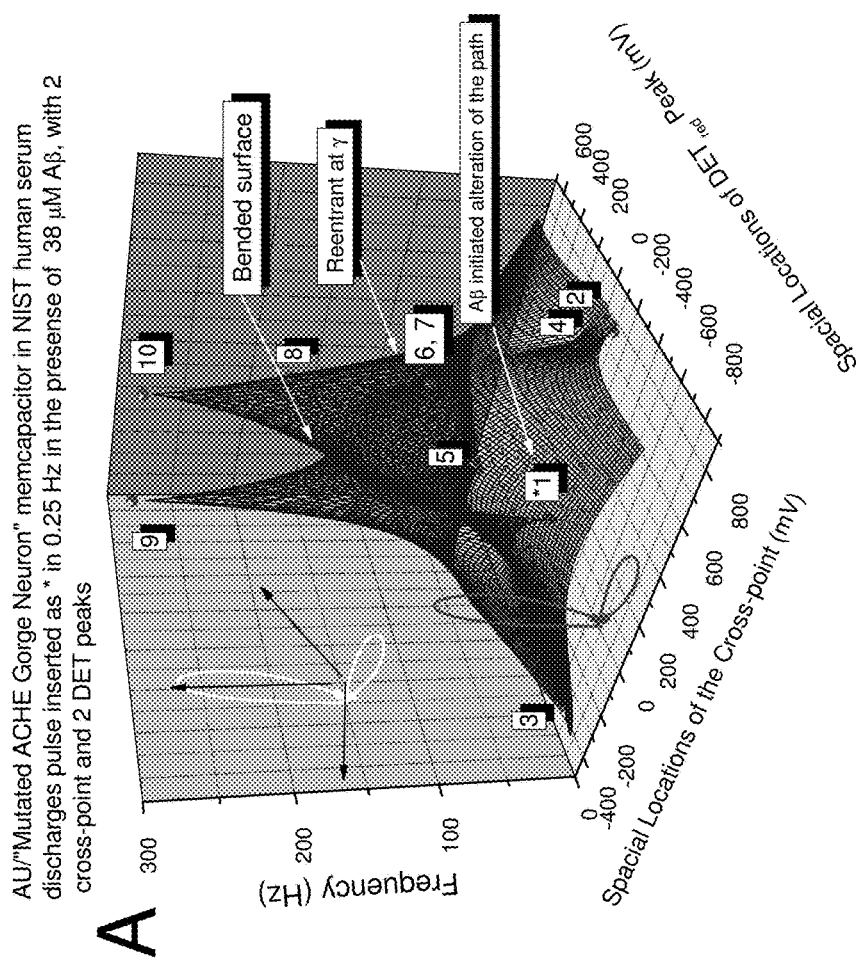

AU/"Mutated ACHE Gorge Neuron" memcapacitor in NIST human serum discharges pulses infused as * with 38 µM Aβ over 1–300 Hz, with multiple cross-point and DET peaks

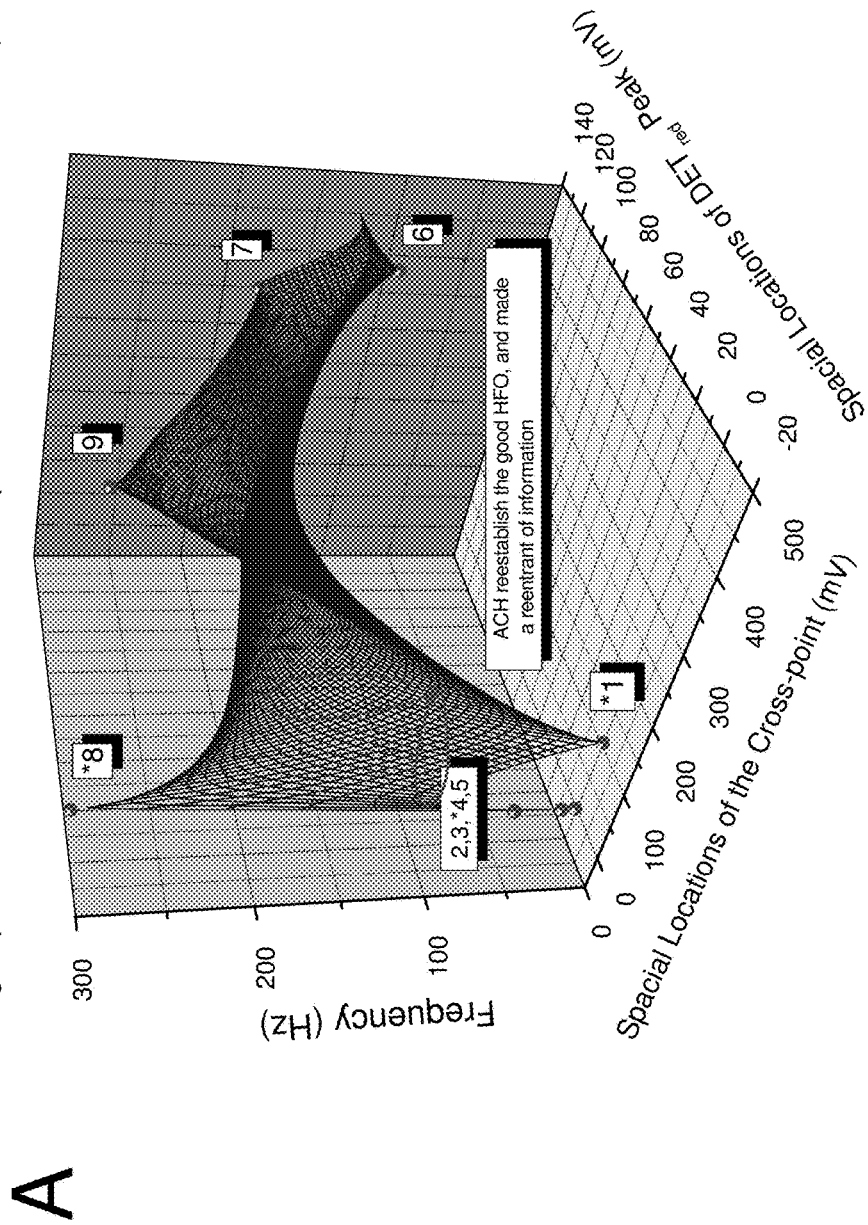

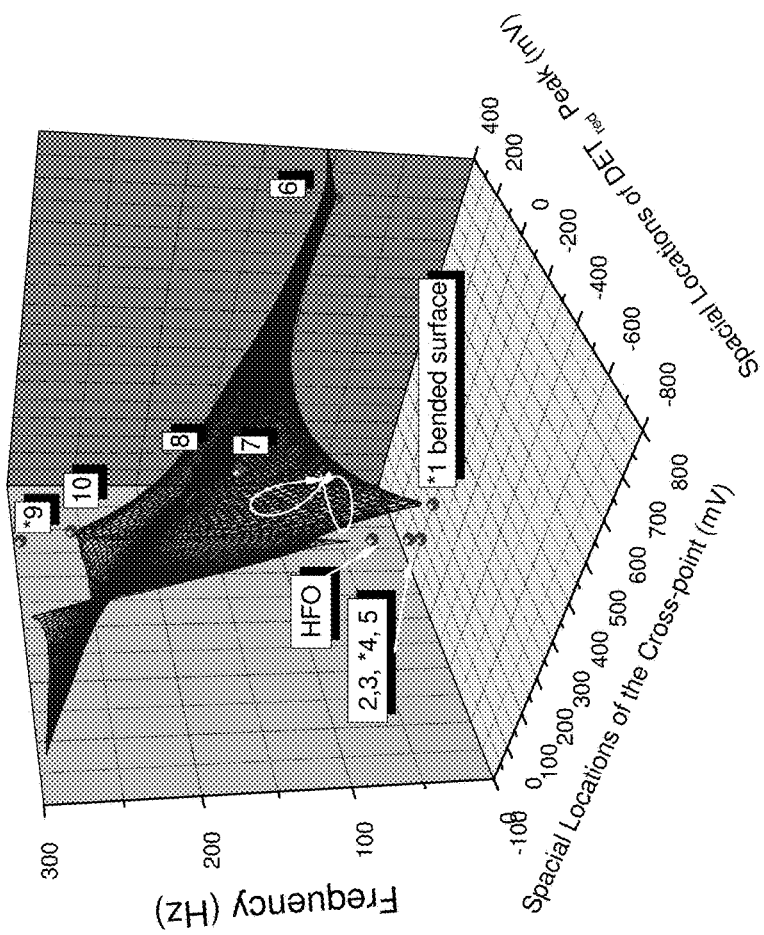

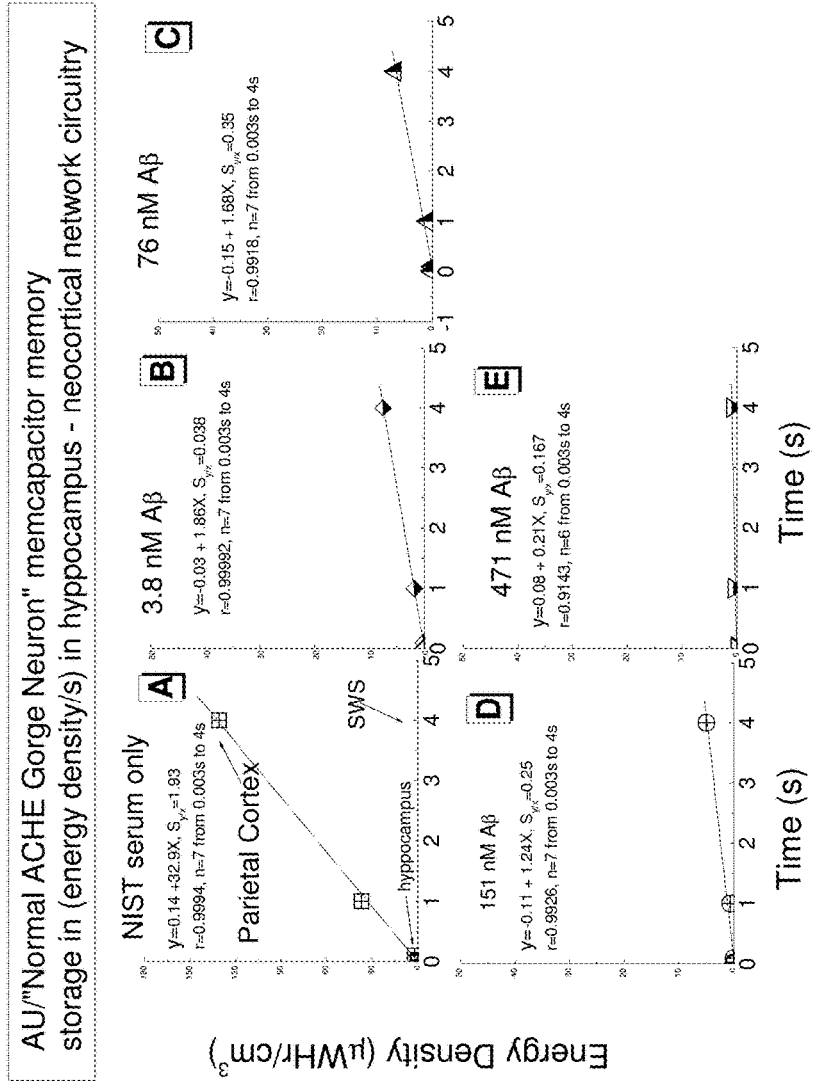

NANO-BIOMIMETIC MEMS-TRANSFORMER DEVICES OF MAKING AND AN APPLICATION IN ENERGY-SENSORY IMAGES THERETO

FIELD OF THE INVENTION

This non provisional patent application entitled of "Nano-biomimetic Mems-transformer Devices of Making And An Application in Energy-Sensory Images Thereto" relates to the field of electromagnetic systems and induction. In particular, to a device having the characteristics of mems-capacitive, mems-ristive and mems-inductive comprising of a first and a second nanostructured toroid along with its applications invented in Energy-Sensory images thereto.

The shortcomings of artificial neuronal networks (ANN)s systems developed through electric circuitry architectures have no or loose connections to neuroscience were mentioned in the literature [1]. As a consequence, the shortcomings include, not limited to ignore features of biological neural processing systems, such as their extremely low-power consumption features, sensory and flexibility. Memristors and memcapacitors have made significant progresses in the recent decades [2-4]; especially with nanotechnology has been incorporated [5-7]. Many diseases are rooted in circadian rhythm (CR) dysfunction. Severe CR dysfunction leads to memory loss and worsens the quality of life. There are 40 million American reported to have chronic long-term sleep deprivation [8]. Researchers reported that Amyloid-β (Aβ) overturns the acetylcholine (ACH) and melatonin release from a normal CR function to a dysfunctional CR [9-10]. Our group developed a sensor that mimics acetylcholinesterase (ACHE) active sites in the ACHE gorge and is able to detect ACH in fM level compared with a "mutated ACHE neuronal gorge" sensor, whose 14 hydrophobic residue groups were knocked out [7]. Aβ's accumulation and neurofibrillary tangle are identified as major pathological biomarkers linked to Alzheimer's disease (AD) [11-14]. Obviously, it is desirable that the ACH sensor is able to detect sub pM Aβ [15].

Slow-wave sleep (SWS) is closely associated with declarative memory consolidation, and the signal is stronger in SWS than in wakeful time [16-18]. One of the neuronal safe guards to this cognitive function is the bidirectional invariant reentry neuronal network circuitry [19-21]. Many models propose to simulate the closed-loop circuitry's reentry functions, however, very few, if any, to really develop a neuronal device which can correlate the reentrant characteristics of "memory" and the influence of neuronal toxins and visualize its function in an image. We thought a memristor/memcapacitor with biomimetic ACHE neuronal gorge functions might be able to face this challenge [22-23]. A review by Cabaret for organic memristors' capability as artificial neural networks was published [24, 6].

Researchers discovered Alzheimer's disease (AD) patients have lost the sense of smell due to Aβ inhibition of olfactory bulb activity [25-28]. Here, we further propose a hypothesis that memories of an artificial, intelligent neural network are not only associated with the "Sensory Biomarkers", but also correlated with the primary neural network's energy density in a frequency domain that must governed by the memristor/memcapacitor's rules under the inspiration of our previous work [16].

A normal neural network circuitry constantly fires high frequency oscillation (HFO) (150-200 Hz) producing synchronization within the connection between hippocampus and neocortex for long term memory storage during Slow-Wave Sleeping (SWS), and where pathological high frequency oscillation (pHFO) (200-600 Hz) fires randomly leading to seizures and epilepsy [29-31]. The biggest problem in epilepsy research, as the Editor Noebels explained in the book, is that researchers are "not clear how abnormal synchrony is generated during pHFO. Clearly there is a need for additional studies that will differentiate normal from pathologic HFO in vitro and in vivo."[29]. In this invention, we attempted to find a method to differentiate and predict the presence of pHFO and HFO based on a mem-transformer that embodiments with memcapacitive/memresistive/meminductive characteristics to mimicking neural network circuitries and herein find its applications in the energy-sensory optical images.

SUMMARY OF THE INVENTION

It is an object of the present invention to provide a new generation of mem-transformer that embodiments with memresistive/memcapacitive/meminductive characteristics that closely linked to neuroscience in particular, they are memory devices which can conduct memory retrieve and storage in biological fluid.

It is an object of the present invention to provide a new generation of mem-transformer that was not made by metal oxide, but of biomimetic organic polymer membrane that mimics a normal cylindrical confined acetylecholenesterase (ACHE) eternal gorge as a "normal brain" prosthesis model with a "biomimetic linen" attached in the gorge thereto.

It is an object of the present invention to provide a new generation of mem-transformer with new method of making multiple-layers membrane with cross-bridge and bars.

It is an object of the present invention to provide a new generation of mem-transformers that are comprising of an biomimetic organic polymer membrane that mimics a mutated acetylecholenesterase (ACHE) eternal gorge with 14 hydrophobic residues groups knocked out, serves as a "damaged brain" prosthesis model.

It is an object of the present invention to provide a new generation mem-transformer that mimics a normal brain circuitry integrity from the "normal brain" device and the "mutated ACHE" device mimics damaged brain circuitry, in particular, the neocortex-hyppocampus circuitries with and without the presence of Aβ.

It is a still further object of the present invention to provide the mem-transformer having an application in an Energy-Sensory brain circuitry image that dynamically displays the circuitry synapse change and the circuitry surface conformation change over frequencies from SWS to 300 Hz in 3D; and in contour color map and in optical image in the presence of an intruder or analyte, such as Aβ, cancer cells, ACH and viral with $10^{-3}$ to $10^{-5}$ s temporal resolution and sub $\mu m^3$ special resolution. The primary group synapse circuitry has a circular current flow special resolution.

It is a still further object of the present invention to provide a method to establish Sensory Biomarker from any brain circuitry that use i-V curves of memristor for cross-point electric field location and the direct electron transfer peak location in a given electrochemical field; and establish a matrix of the Sensory Biomarker at a fixed frequency.

It is a still further object of the present invention to provide a method to establish brain discharge pulse energy infusing into a Sensory Biomarker random gridding correlation matrix in order to enable the communication between brain prosthesis with sensory matrix, pulse energy and the analyte.

It is a still further object of the present invention to provide a method for quantitatively assess the brain reentrant memory sensitivity in less than 1 fj/bit/μm³ in biological fluid and senses the energy change in atto WHr.

It is a still further object of the present invention to provide a new generation of energy device to recognize the presence of pHFO from HFO and establish a link to early CR dysfunction and a link to early AD.

It is a still further object of the present invention to provide an Energy-Sensory brain circuitry images that are capable to identify and predict the four stages of epilepsy from asymptomatic to "life threatening".

It is a still further object of the present invention to provide an in vitro diagnosis and monitoring neuronal dysfunction method that monitor before and after the therapeutic administration of medicine through monitor the communication between patient blood specimen and the device prosthesis painlessly, then the results are demonstrated and compared in the Energy-Sensory image suite as a tool for doctors and pharmaceutical drug developers to seek a new road.

It is a still further object of the present invention to provide an Energy-Sensory brain circuitry images that are capable to identify and predict early CR dysfunction.

It is a still further object of the present invention to provide an in vivo healing tool pain-freely to repair neuronal dysfunction patients by put on the flexible device patches over their head at different locations to release stimulate pulses during SWS.

It is a still further object of the present invention to provide orders of magnitudes amplified output voltage or amplified output current without a special electric circuitry added, it is solely depending upon the design and the architecture of the membranes in winding and inserting in the form of a toroid.

BRIEF DESCRIPTION OF THE DRAWINGS

FIG. 1D shows the AFM specification of the surface roughness results based on the side view.

FIG. 4D depicts the schematic components of the device 2 having different layers and each one serves their own functions. "10" is the plastic plate; "11" is the Au, or Pt, or metal electrode; "12" is the imidazolyl derived mono-substitute β-dimethylcyclodextrin (m-β-DMCD, in short, MCD) cross-linked with PEG, PVP and TCD forming self-assembled conductive organic membrane with clockwise electron-relay circular currents flow; "13" is the nano air gap between two chucked CD "donuts-like" cavity; "14" is the cross-bar consists of polymers residue groups having counter clockwise electron-relay circular current of TCD . . . MCD . . . PEG . . . PVP wrapping around with ribbon of TCD . . . PEG//TCD . . . PVP; "15" is the nano air gap between 14 and 15 cross-bars; "16" is the slot for injection of biological sample; "17" is the 50 nm thickness pure gold electrode on the plastic substrate.

FIG. $11A_1$ illustrates device 1's volumetric energy density vs. time using the DSCPO voltage method at ±10 nA over 0.25 to 1000 Hz in NIST serum without spiking Aβ; FIG. $11A_2$ is the voltage vs. time profiles in the presence of 3.8 nM Aβ; and FIG. $11A_3$ is the profiles in the presence of 76 nM Aβ.

FIG. 11B depicts the profiles of various concentrations of Aβ impacting on the device 1's performance in volumetric energy density vs. change of frequencies from 0.25 Hz to 333 Hz compared without spiking Aβ in NIST standard human serum at ±10 nA at room temperature with each sample run triplicates.

FIG. 12A, FIG. 12B and FIG. 12C depict the voltage profiles vs. time using the DSCPO method in NIST serum with 38 μM Aβ or without Aβ at ±10 nA on device 2. The blue line refers to serum only without Aβ and without spiking ACH as "a"; the red curve refers to in the presence of 38 μM Aβ as "b" in 0.25 Hz, at 40 Hz and at 250 Hz, respectively.

Figure 13:
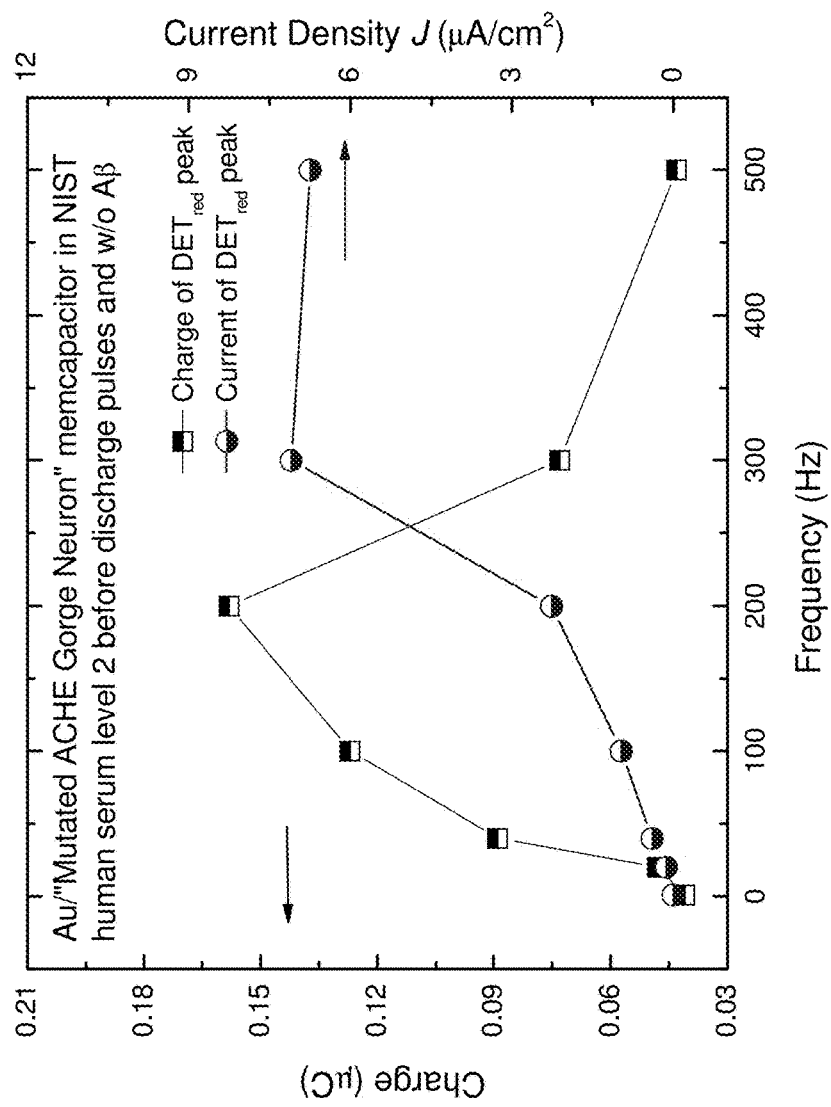

FIG. 13 depicts the memcapacitor characteristics of non-linearity of charge vs. frequencies and the current density vs. frequencies before discharge pulses and without spiking Aβ, respectively for device 2 in NIST serum with certified blood glucose level 2.

Figure 14:
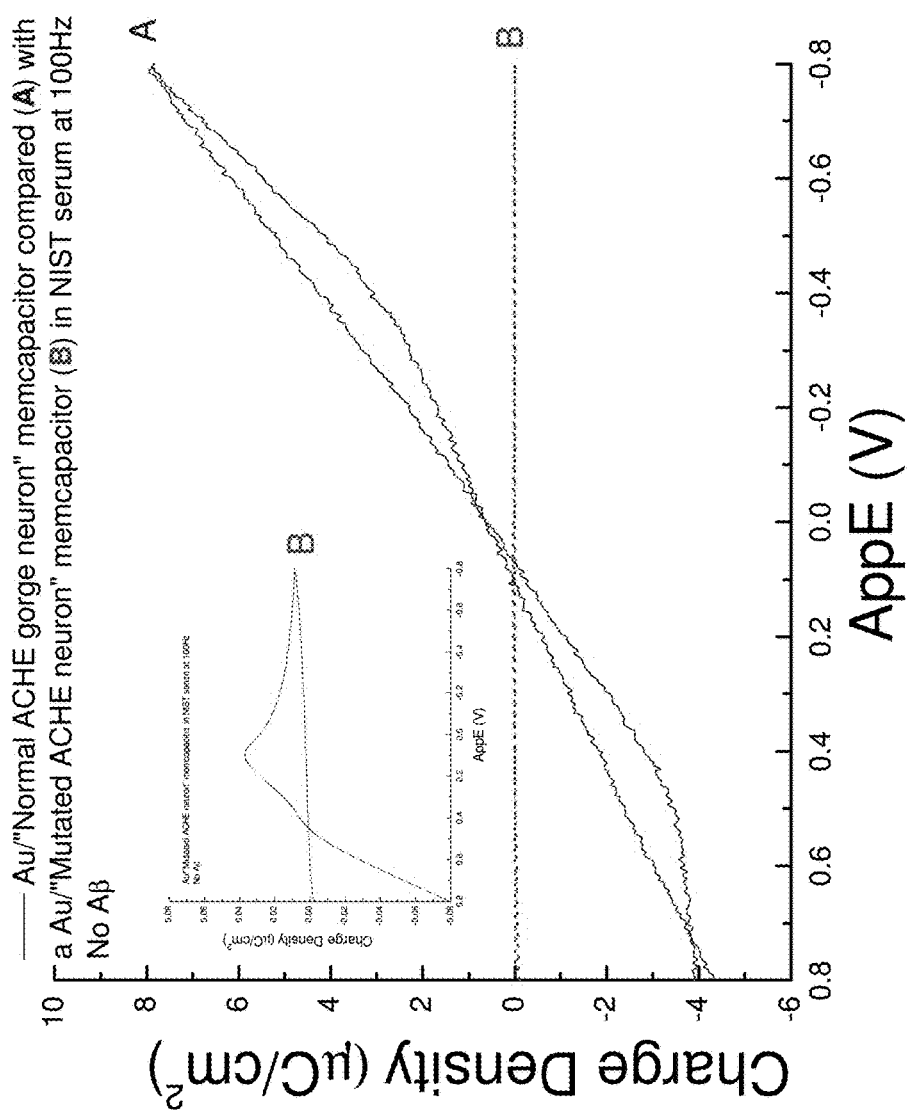

FIG. 14 depicts the memristor's characteristics of charge density vs. potential with hysteresis pinch at different potentials compared with device 1 (blue curve) and 2 (red) at 100 Hz using the CV method in NIST serum without Aβ.

Figure 15:
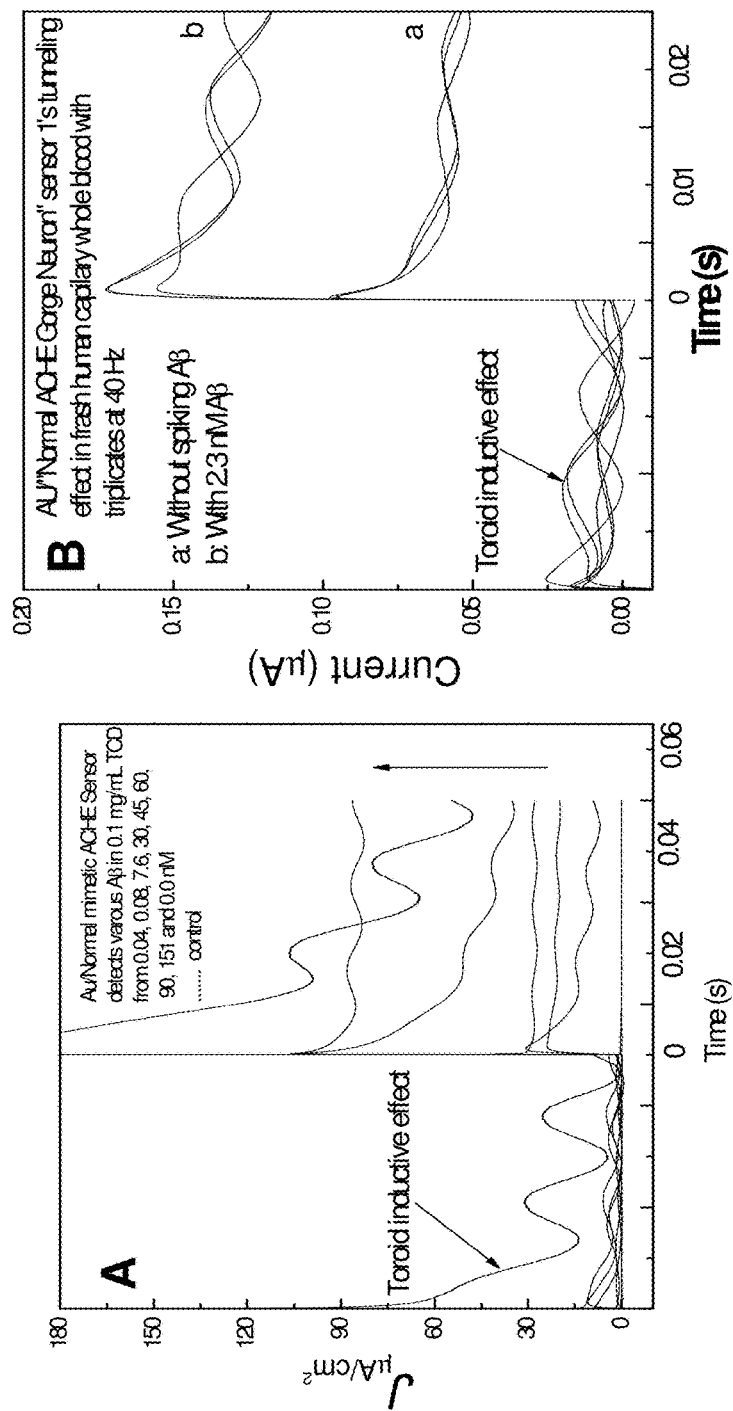

FIG. 15 panel A depicts the toroidal transformer's longitudinal tunneling effect and the DC/AC convertor effect due to the electromagnetic inductivity on device 1 with a flat ACHE gorge bridge/nanopore configuration using a CA method with a DC voltage $E_0$=0 mV, $E_1$=−50 mV, $E_2$=−200 mV with 50 ms at each of two steps with 80 KHz data rate at various concentration levels of Aβ from 0.04, 0.08, 7.6, 30, 45, 60, 90, 151 nM in aqueous solution with 0.1 mg/mL TCD stabilizer against the control of 0.1 mg/mL TCD in aqueous solution.

FIG. 15 panel B depicts the toroidal transformer's longitudinal tunneling effect on device 1 in fresh human capillary whole blood specimens with triplicates using the CA method under the same experimental condition as in FIG. 15 panel A, but step time is 25 ms (a): without spiking Aβ; (b): in the presence of 2.3 nM Aβ.

Figure 16:
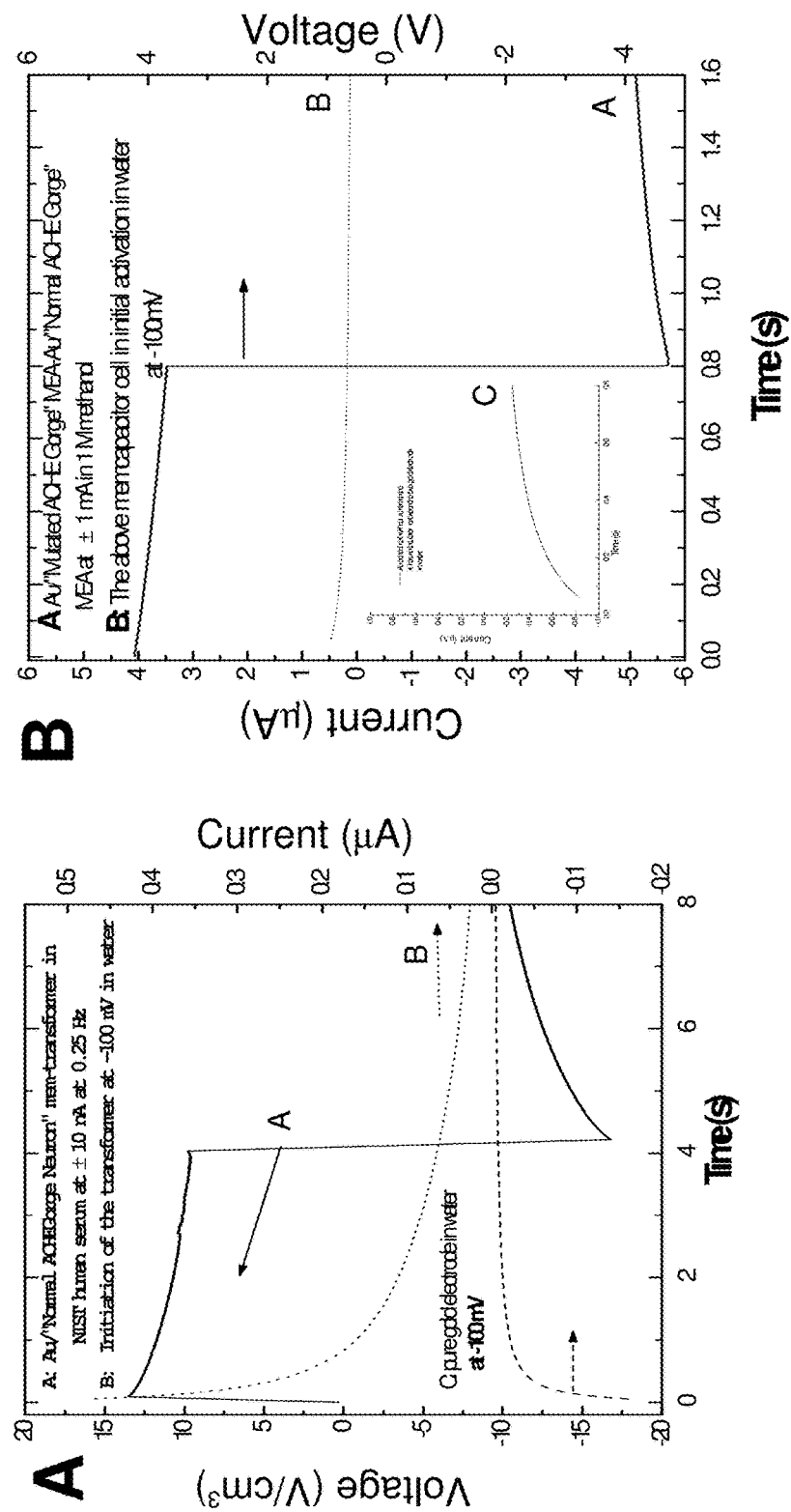
Figure 16:
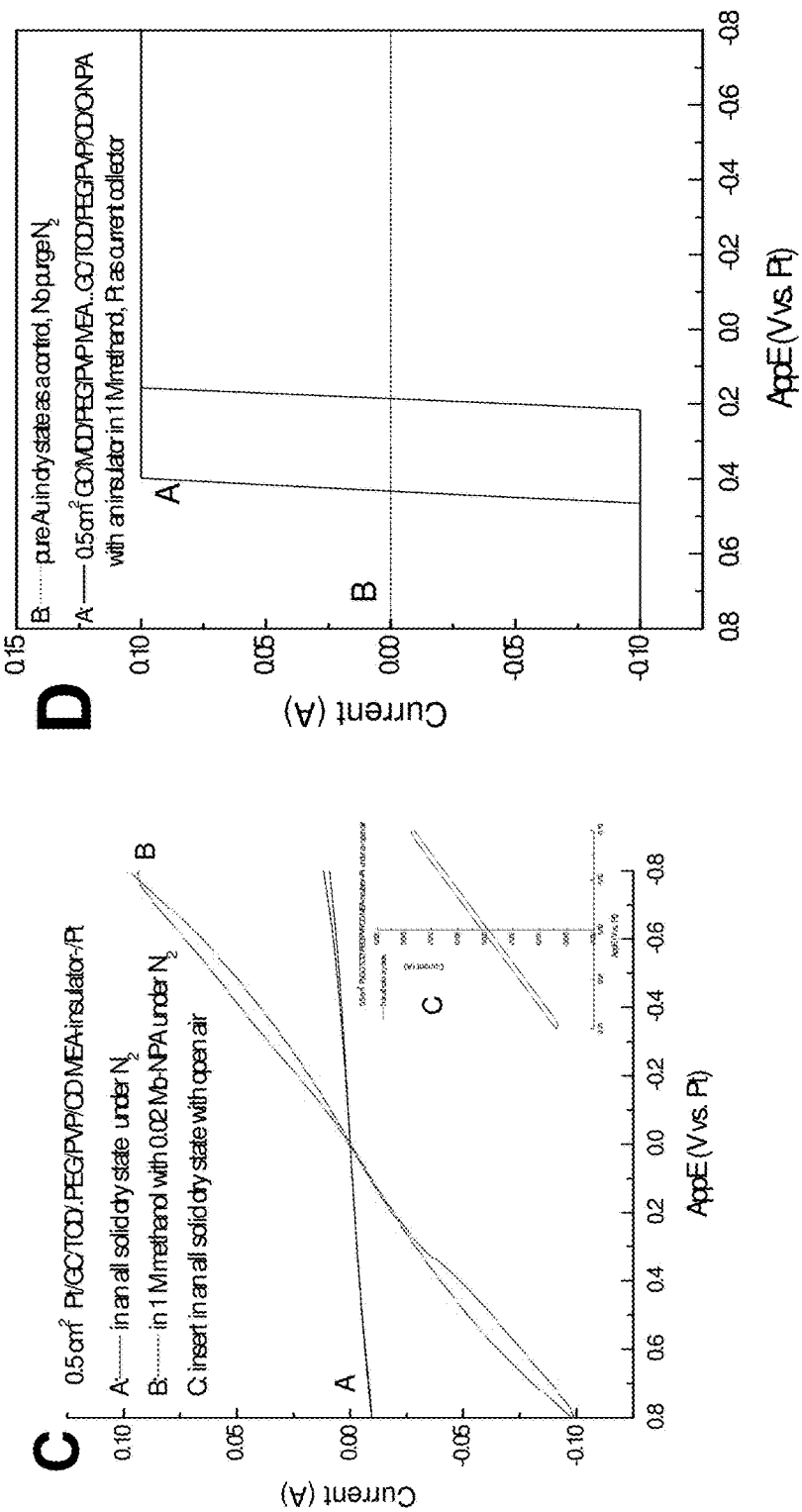

FIG. 16 panel A depicts the toroidal transformer's out put voltage amplification effect using a simple Au/"Normal ACHE Gorge neuron" mem-transformer with flat bridge/nanopore AFM configuration in NIST human serum without spiking Aβ at ±10 nA at 0.25 Hz (a); Against the control of the same device in aqueous solution for the initiation of the device at −100 mV (b); Against the control of the pure gold electrode in aqueous solution at −100 mV.

FIG. 16 panel B depicts Au/"Mutated ACHE Gorge" MEA-insulator-AU/"Normal ACHE Gorge" flat bridge/nanopore MEA configuration in 1 M methanol at room temperature using the DSCPO method at ±1 mA (a); Against the initial activation of the same device in pure water under an applied potential −100 mV using the DC potential amperometry method (b); The insert curve depicts a control curve with a pure gold sensor made of same size, but without a membrane attached, in pure water under an applied potential −100 mV using the DC potential amperometry method.

FIG. 16 panel C depicts 0.5 $cm^2$ GC/TCD/PEG/PVP/CD MEA-insulator-/Pt in an all solid dry state under purge $N_2$ (a); In 1 M methanol with 0.02M o-NPA under purge $N_2$ (b); the insert in an all solid dry state with open air (c); FIG. 16 panel D depicts 0.5 $cm^2$ GC/MCD/PEG/PVP MEA . . . GC/TCD/PEG/PVP/CD/O-NPA with an insulator in 1 M methanol, Pt as current collectors as (a); pure Au in dry state as a control, no purge $N_2$ (b).

Figure 17:
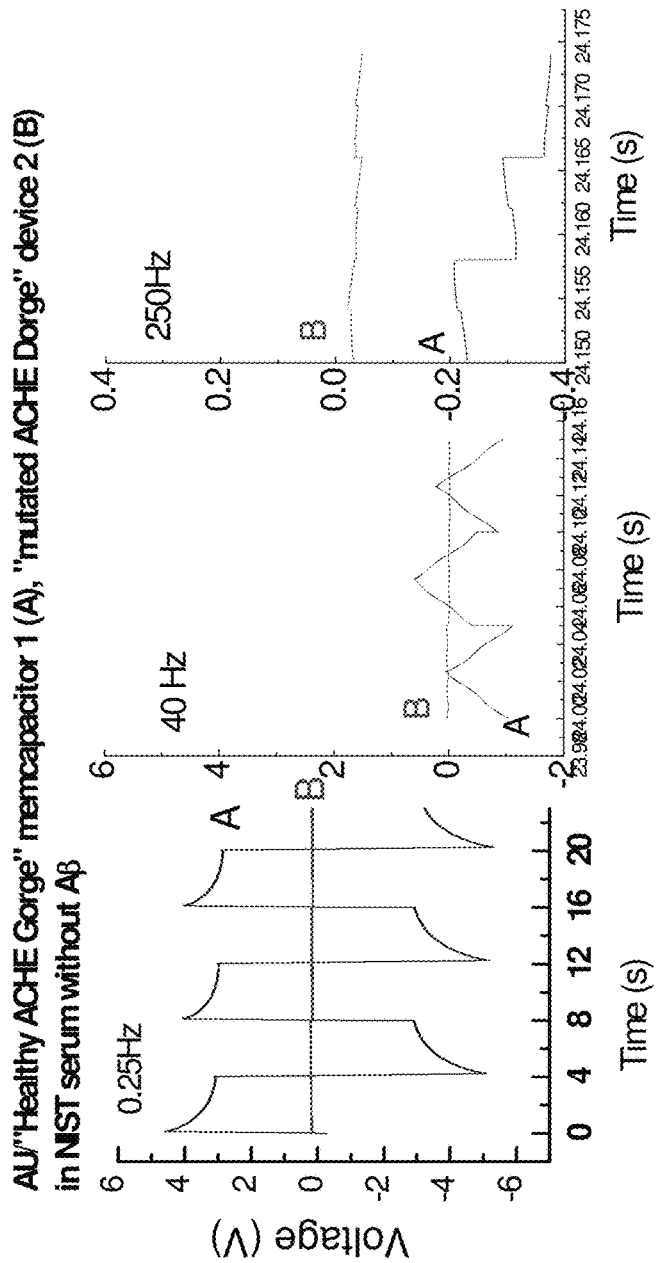

FIG. 17 illustrates the CR profiles at ±10 nA in 0.25, 40 and 250 Hz using the DSCPO method, respectively, from device 1 (blue) compared with device 2 (red) in NIST serum without Aβ. Curves are averaged for three runs.

Figure 18:
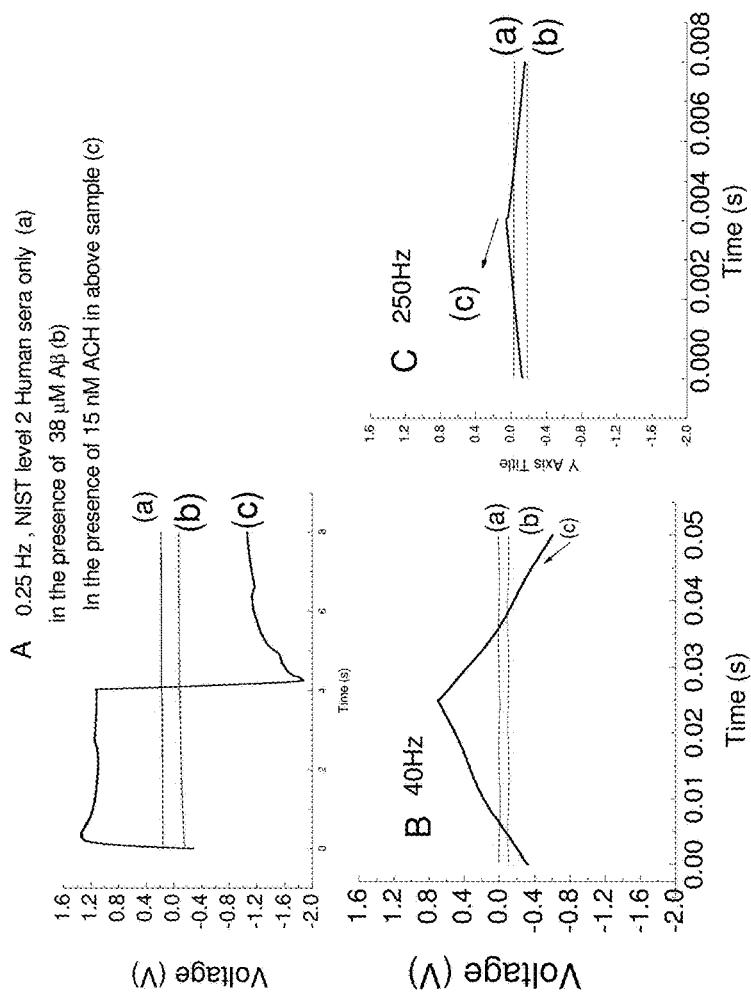

FIG. 18 depicts ACH repairs dysfunction CR at SWS using device 2. The blue line refers to serum only without Aβ and no ACH as "a"; the red line refers to in the presence of 38 μM Aβ as "b" and the black line refers to after a 15 nM ACH presence in the above Aβ serum as "c" at ±10 nA in 0.25 Hz (A), 40 Hz (B) and 250 Hz (C), respectively.

Figure 19:
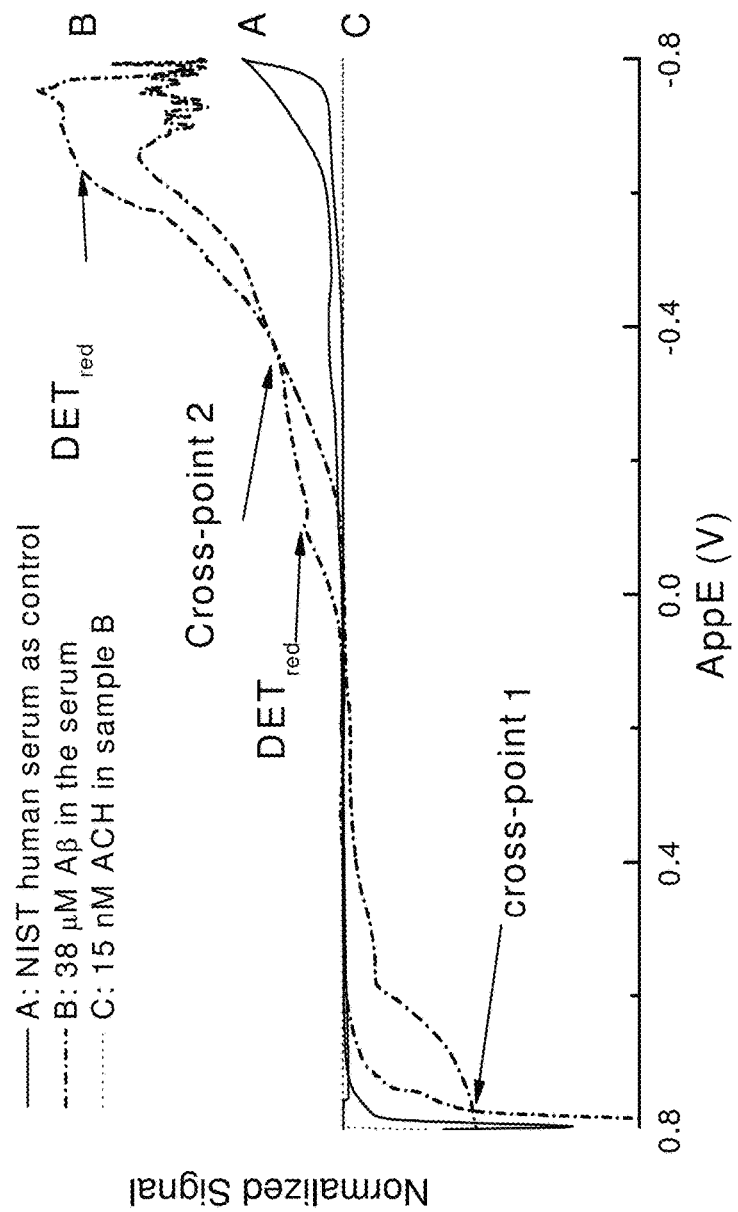

FIG. 19 depicts the CV profiles under the same conditions as in FIG. 18 for device 2.

Figure 20:
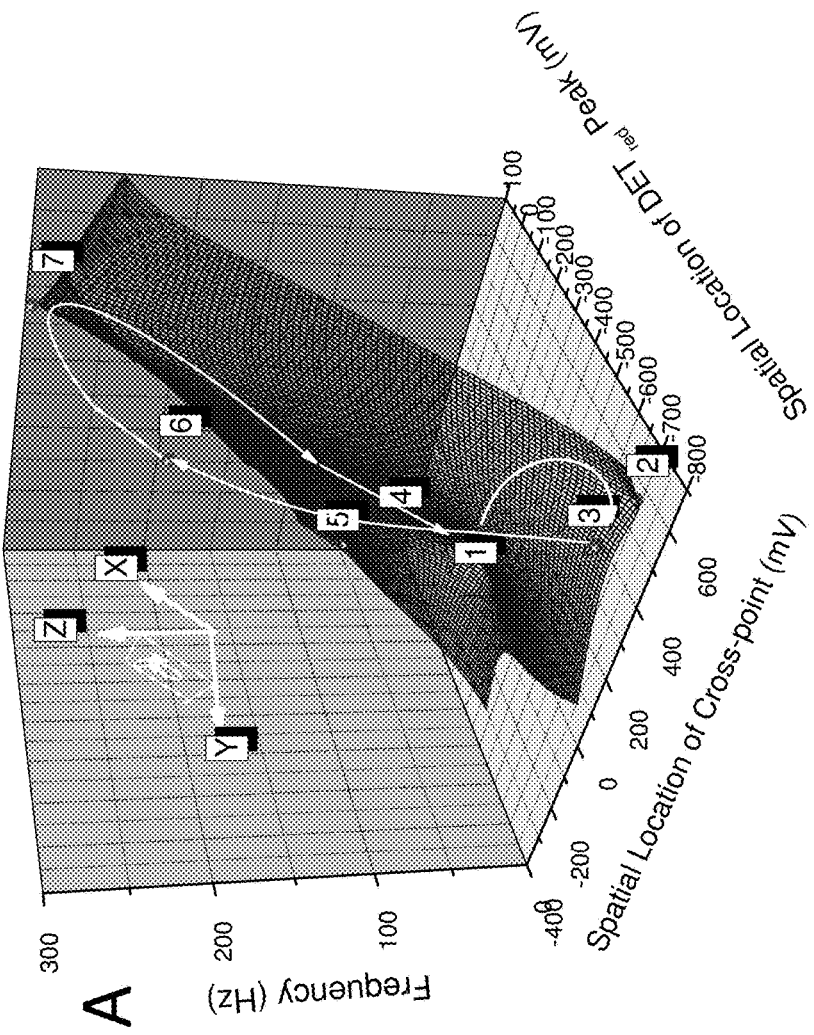
Figure 20:
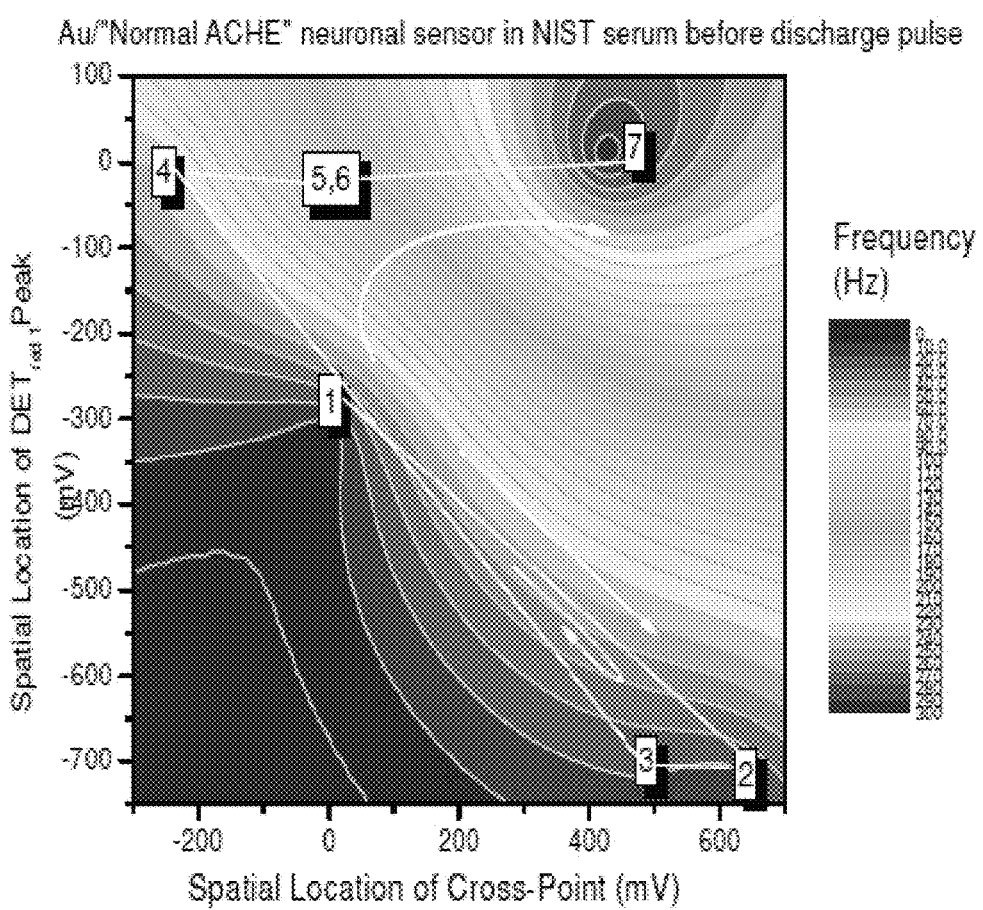
Figure 20:
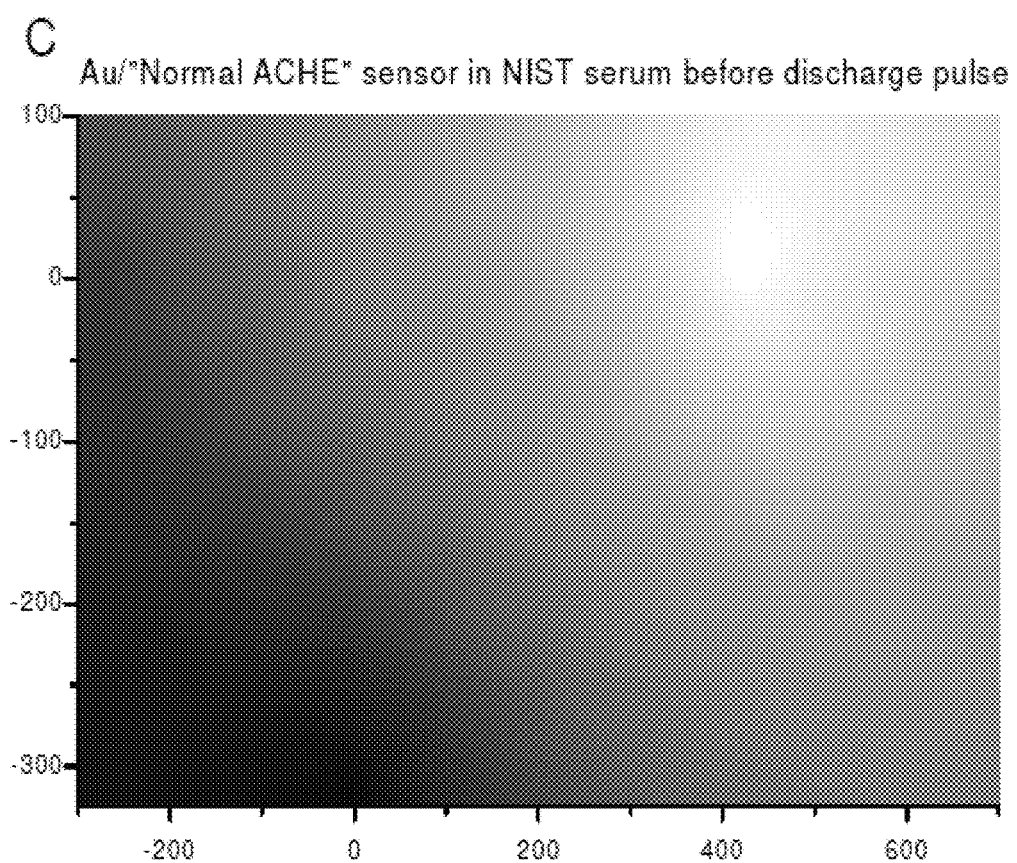

FIG. 20, the panel A depicts the synapse circuitry dynamic 3D Energy-Sensory map of Device 1 interacted with NIST serum before discharges a synapse pulse, and without Aβ. The x-axis is the cross-point location (mV), the y-axis is the DET peak location (mV) and the frequency (Hz) as Z-axis. The labels of the alphabetic numbers refer to the peak at each of different frequencies, started at lowest frequency as "1" in "neocortex", final ending is at the highest frequencies in "hippocampus". The panel B depicts the contour map at the same definitions of axis. The panel C depicts the optical image of the Energy-Sensory map. The light intensity emitted comes from the communication between the bipolar circular electro-relay "neuron network" prosthesis and the media of human serum taken as the original background light intensity at the 3D orientations in the electric field.

Figure 21:
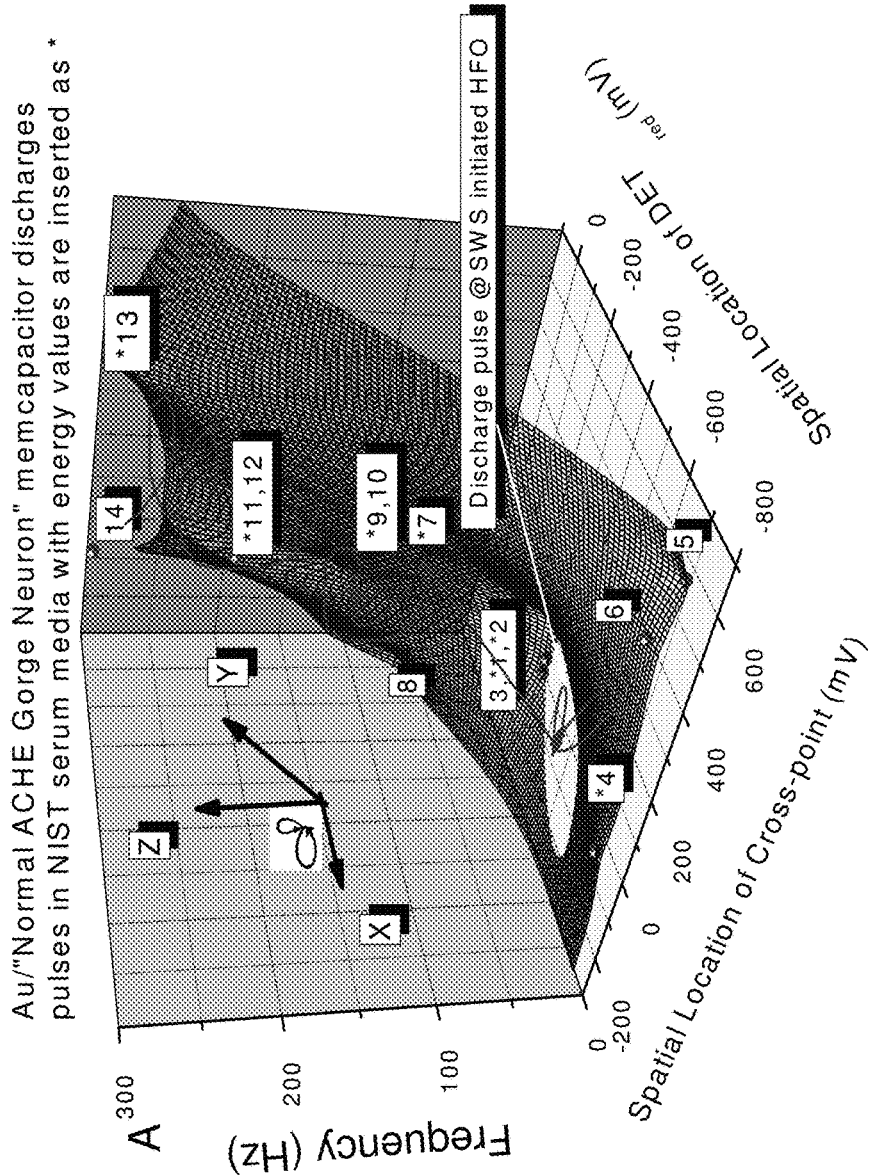
Figure 21:
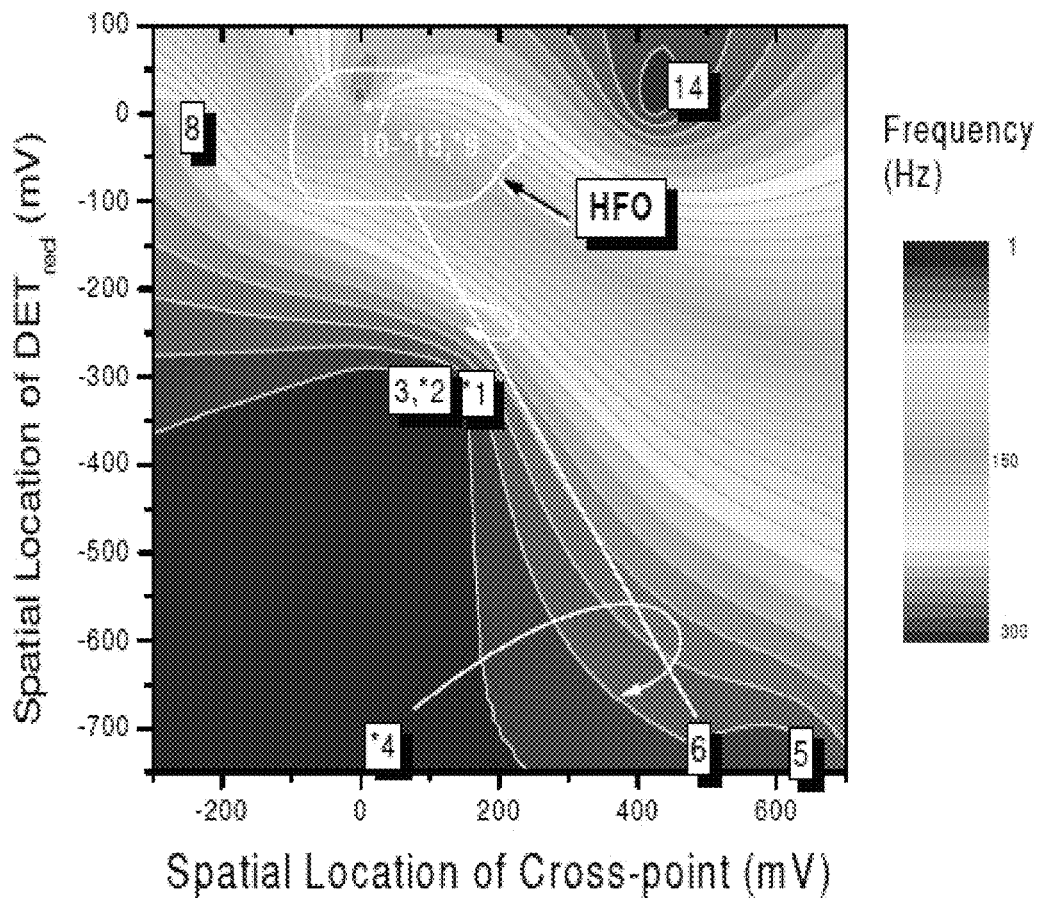
Figure 21:
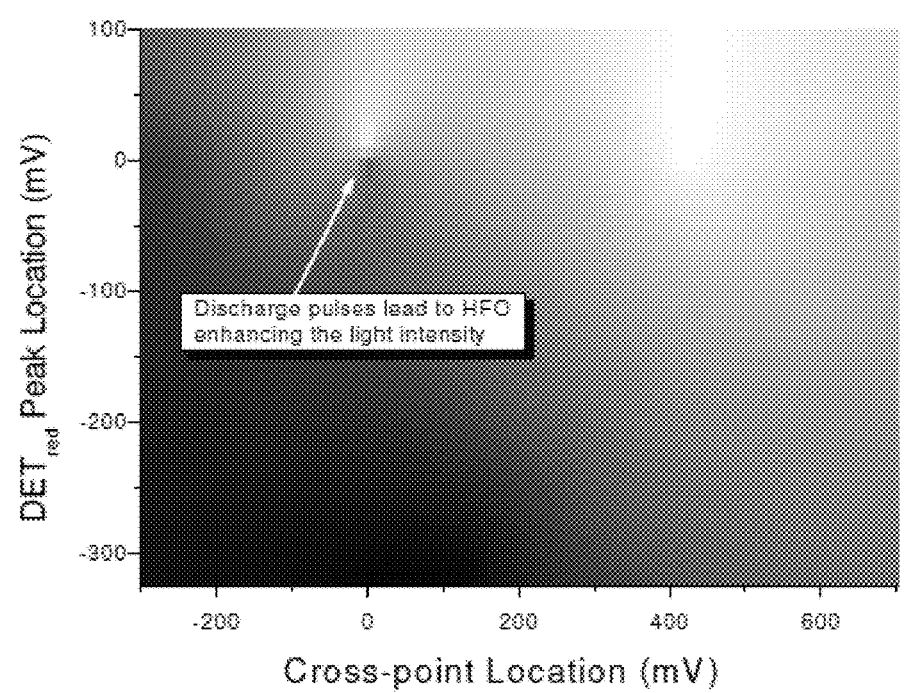

In FIG. 21 the Panel A depicts the synapse circuitry dynamic 3D Energy-Sensory map of Device 1 interacted with NIST serum after discharges synapse pulses and infused the pulse energies into the matrix and labeled as * were shown, and without Aβ. The reentrant point was labeled. The panel B depicts the contour map at the same definitions of axis. The HFO was labeled. The panel C depicts the optical image of the Energy-Sensory map. The HFO was labeled in the optical image.

Figure 22:
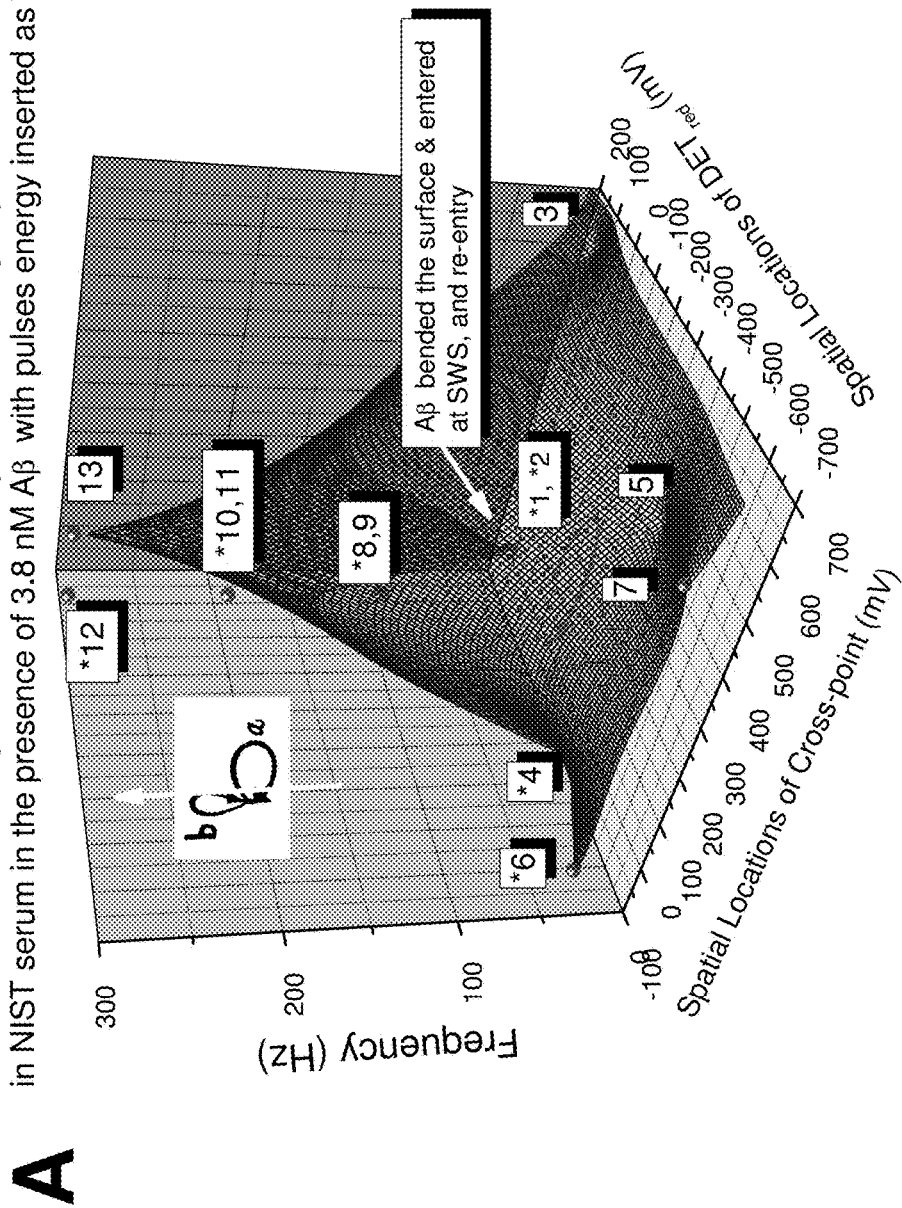
Figure 22:
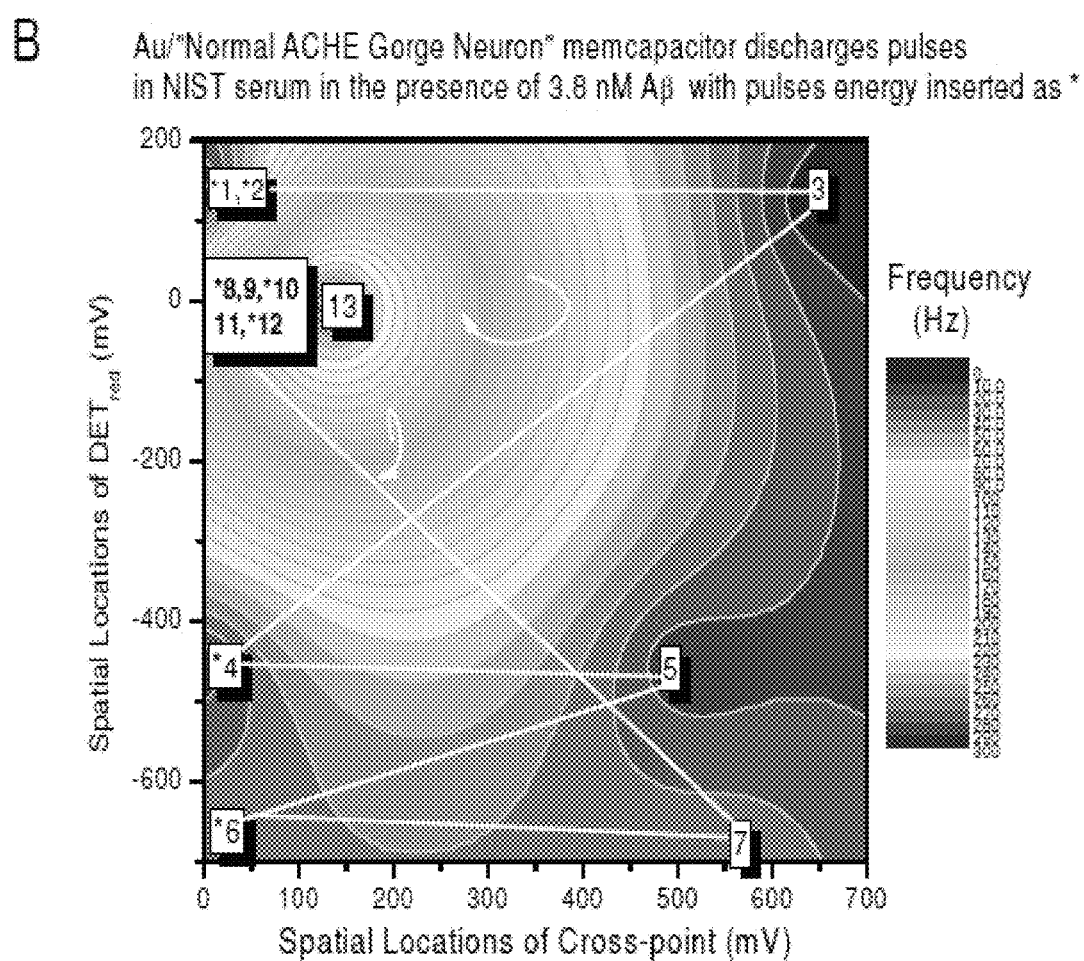
Figure 22:
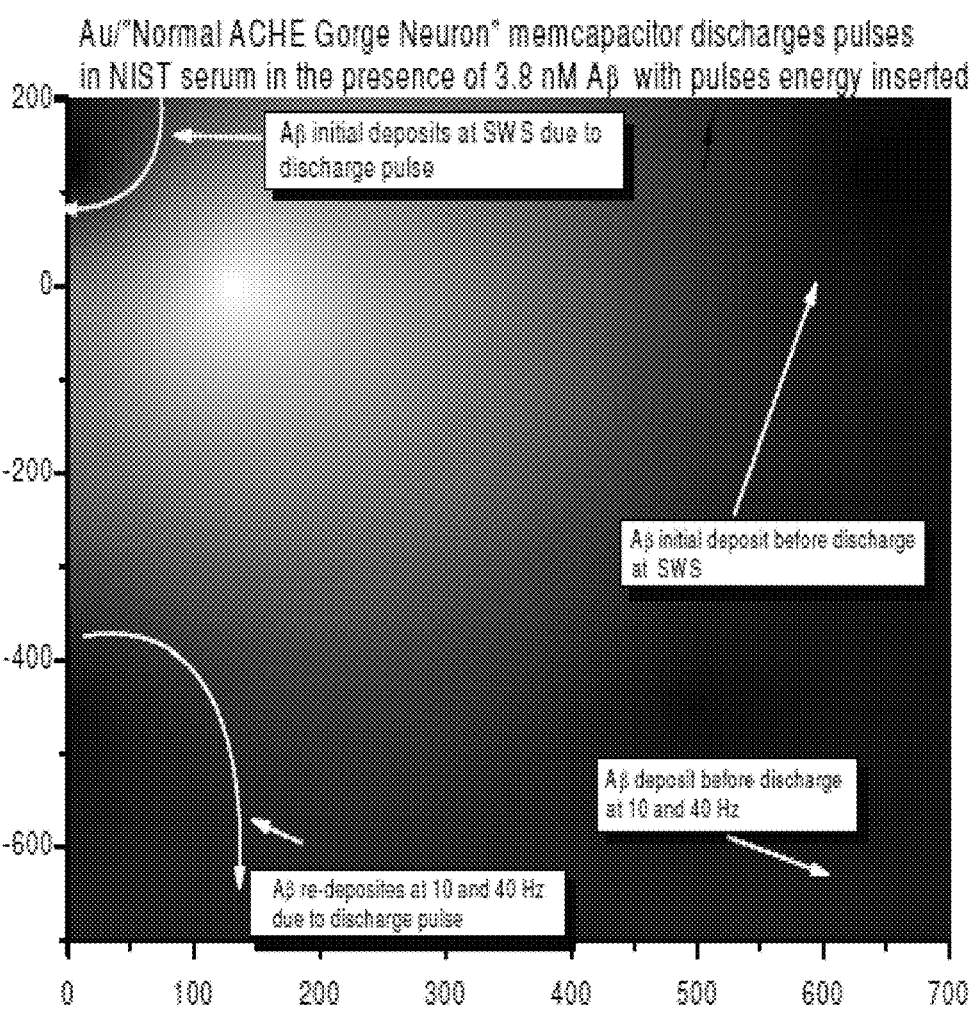

In FIG. 22 the panel A depicts the synapse circuitry dynamic 3D Energy-Sensory map of Device 1 interacted with NIST serum after discharges synapse pulses and infused the pulse energies into the matrix and labeled as * were shown, and with 3.8 nM Aβ. The bad reentrant center was labeled. The panel B depicts the contour map at the same definitions of axis. The panel C depicts the optical image of the Energy-Sensory map. Aβ depositions were labeled.

Figure 23:
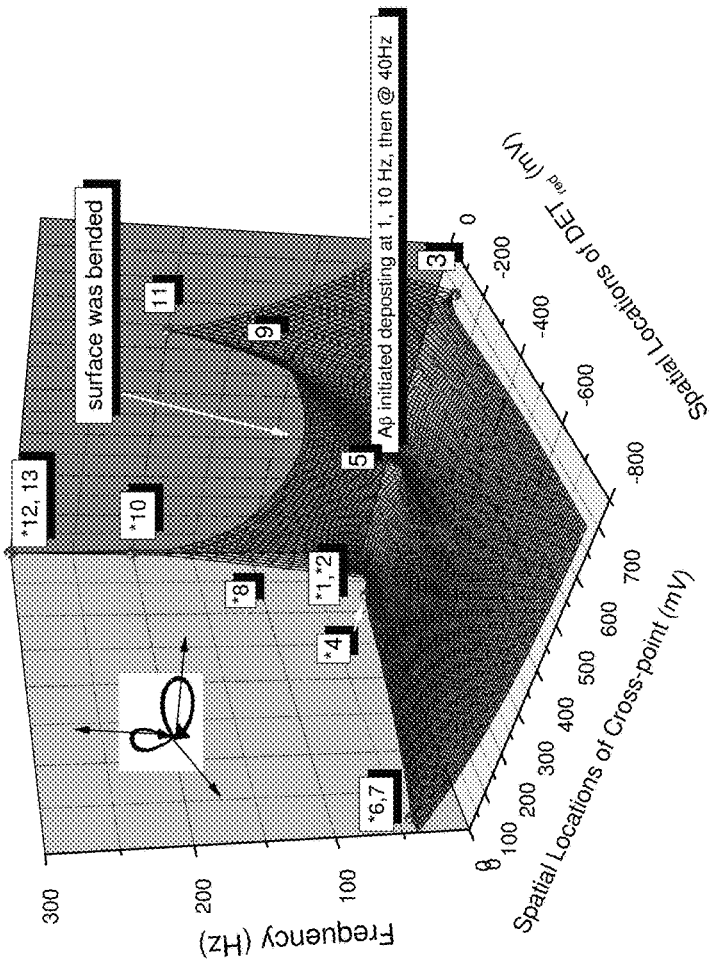
Figure 23:
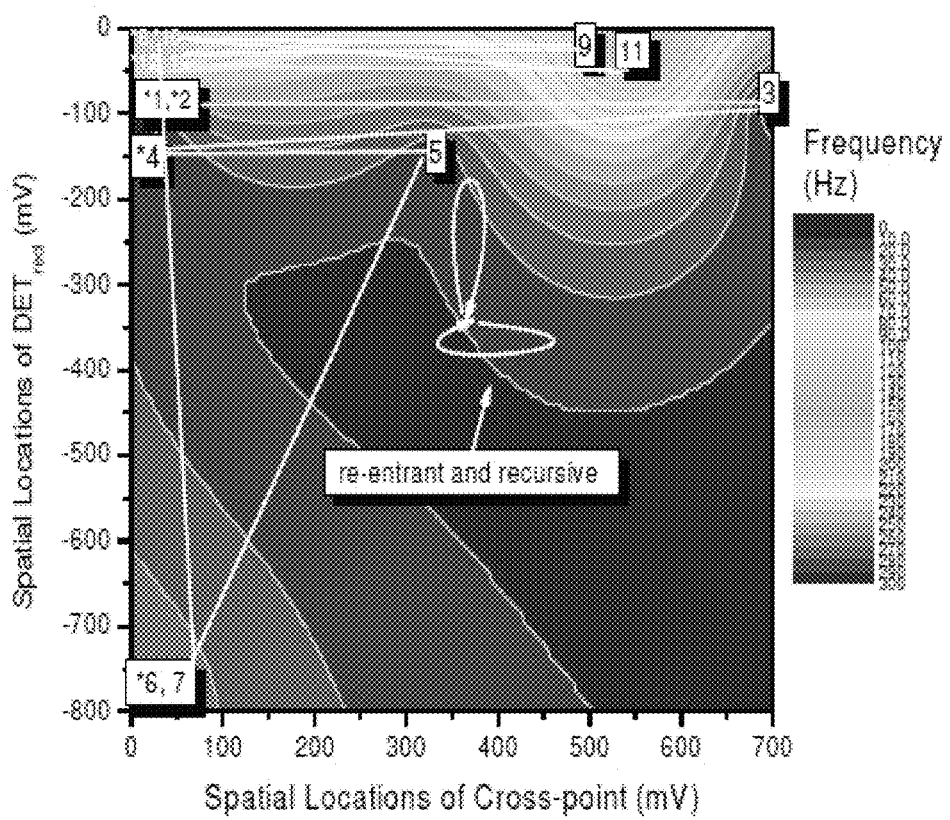
Figure 23:
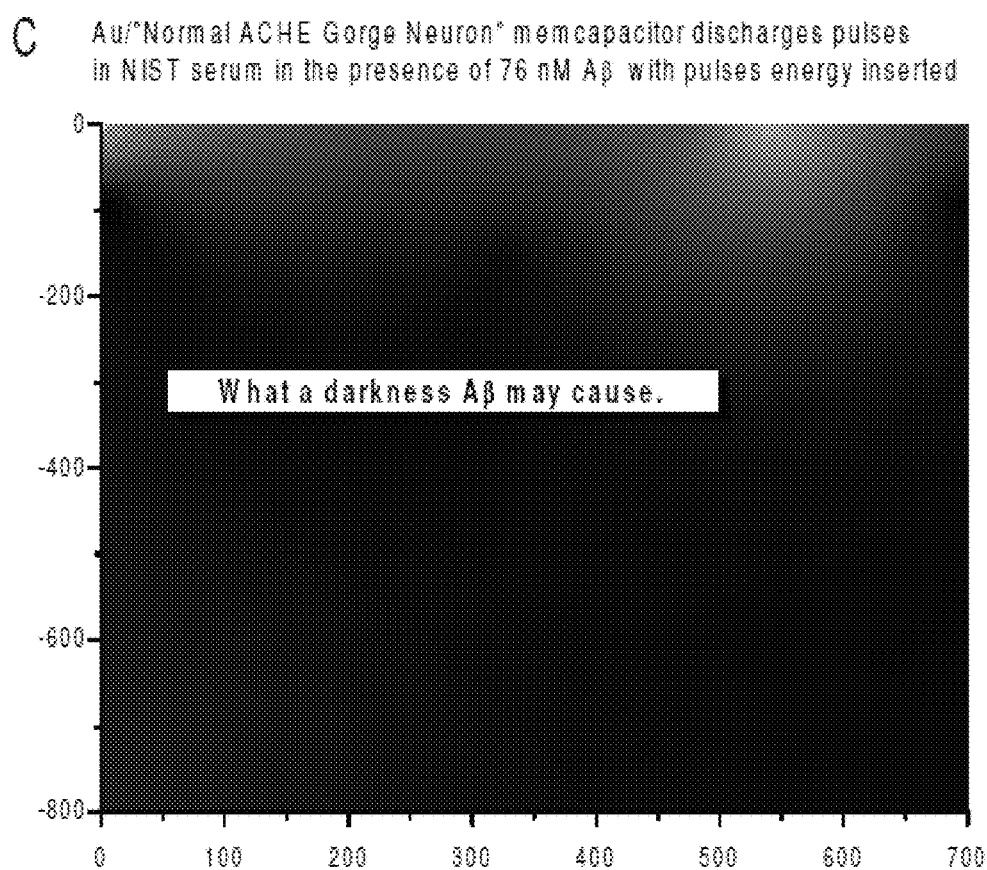

In FIG. 23 the panel A depicts the synapse circuitry dynamic 3D Energy-Sensory map in Panel A of Device 1 interacted with NIST serum after discharges synapse pulses and infused the pulse energies into the matrix and labeled as * were shown, and with 76 nM Aβ. The bad reentrant point was identified with the induction point identified with arrow. The panel B depicts the contour map. The panel C depicts the optical image of the Energy-Sensory map with Aβ depositions were labeled.

Figure 24:
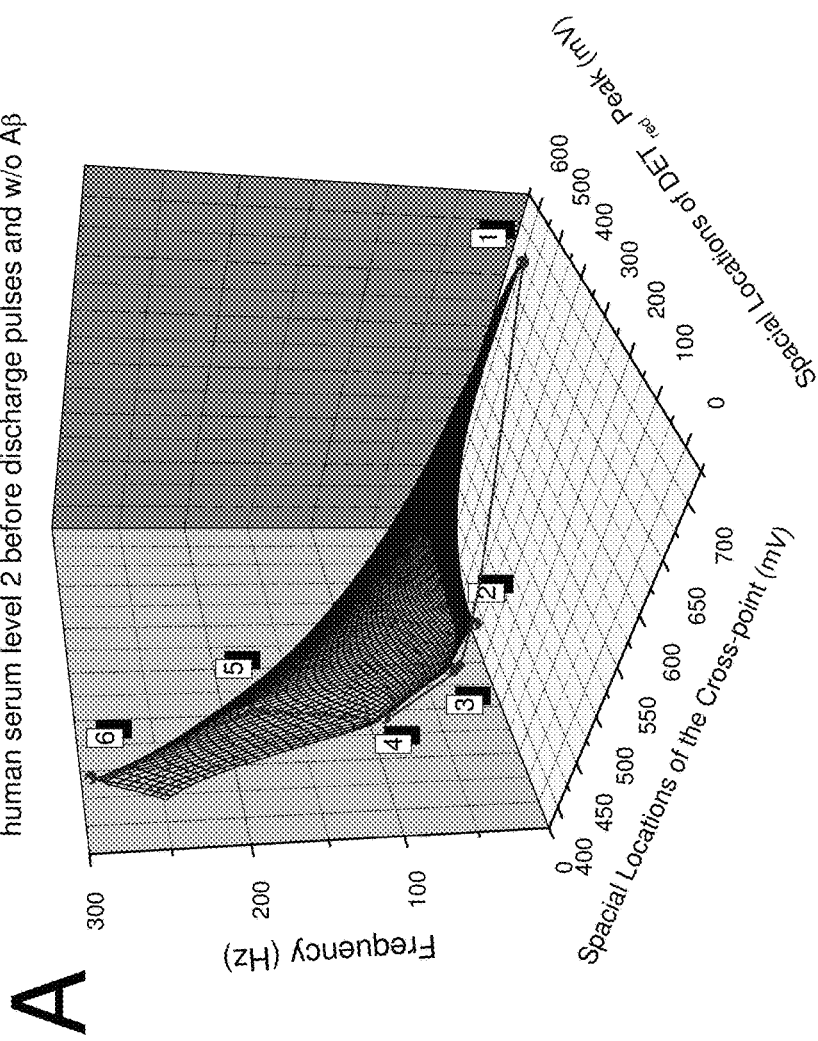
Figure 24:
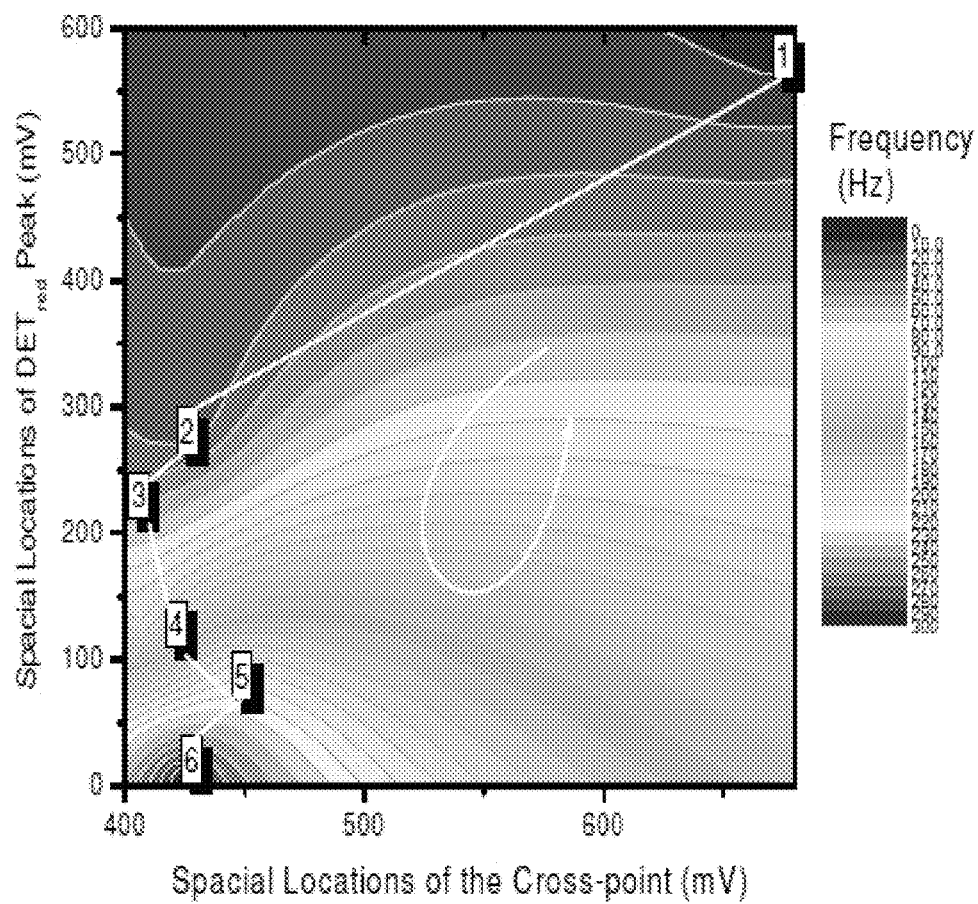
Figure 24:
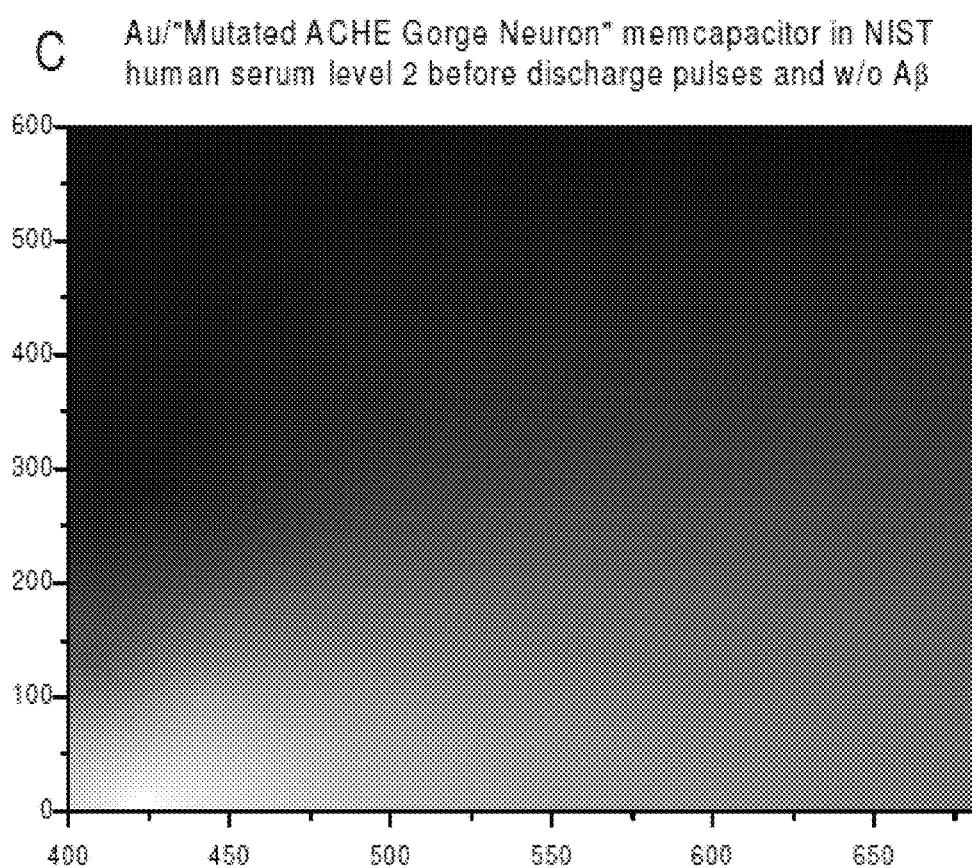

FIG. 24 in Panel A it depicts the synapse circuitry dynamic 3D Energy-Sensory map of Device 2 interacted with NIST serum before discharges a synapse pulse, and without Aβ as "Epilepsy stage 0". The Panel B depicts the contour map and the Panel C depicts the optical image of the Energy-Sensory map.

Figure 25:
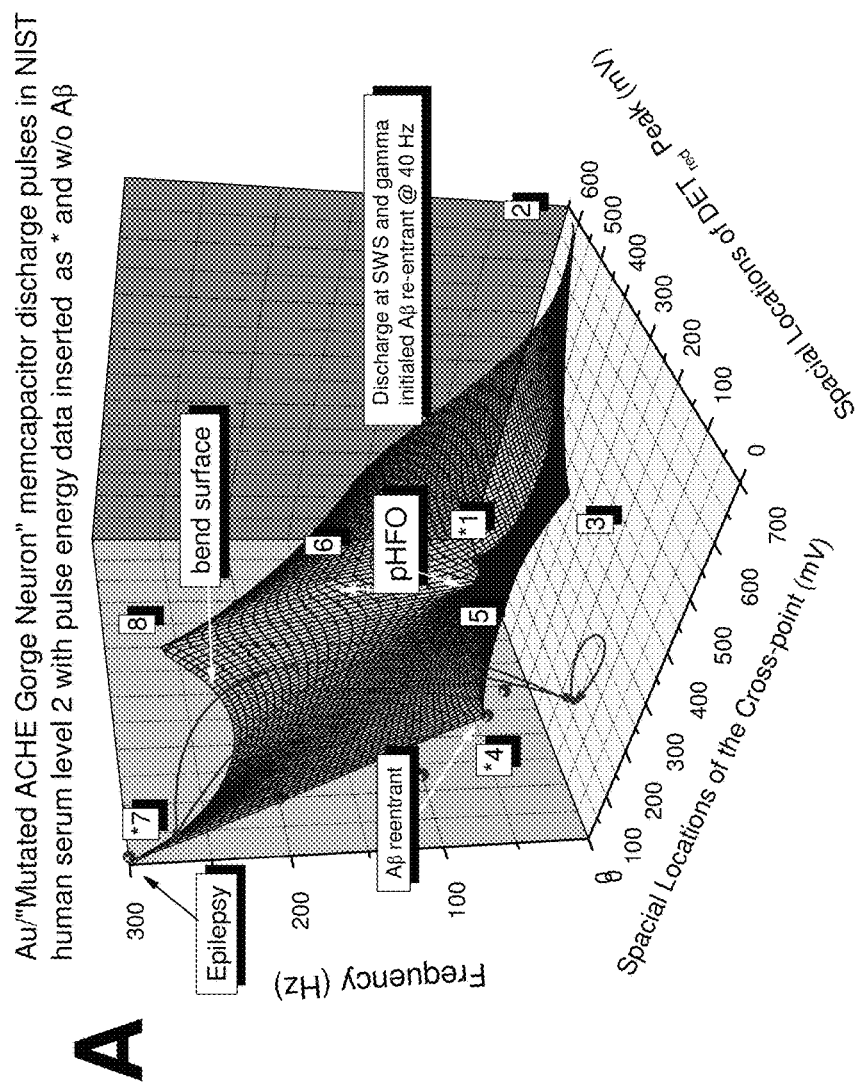
Figure 25:
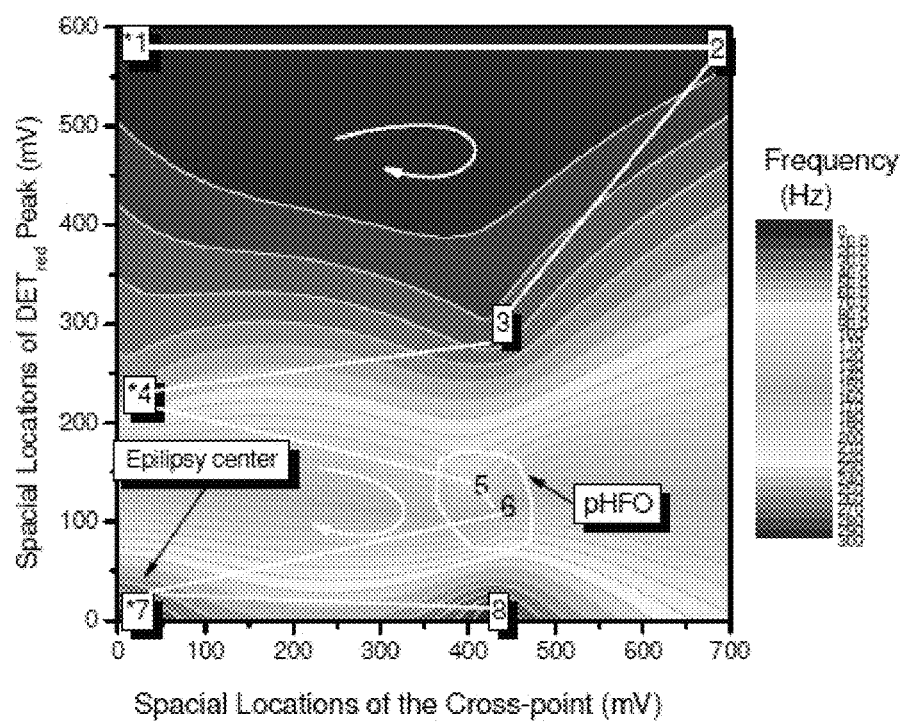
Figure 25:
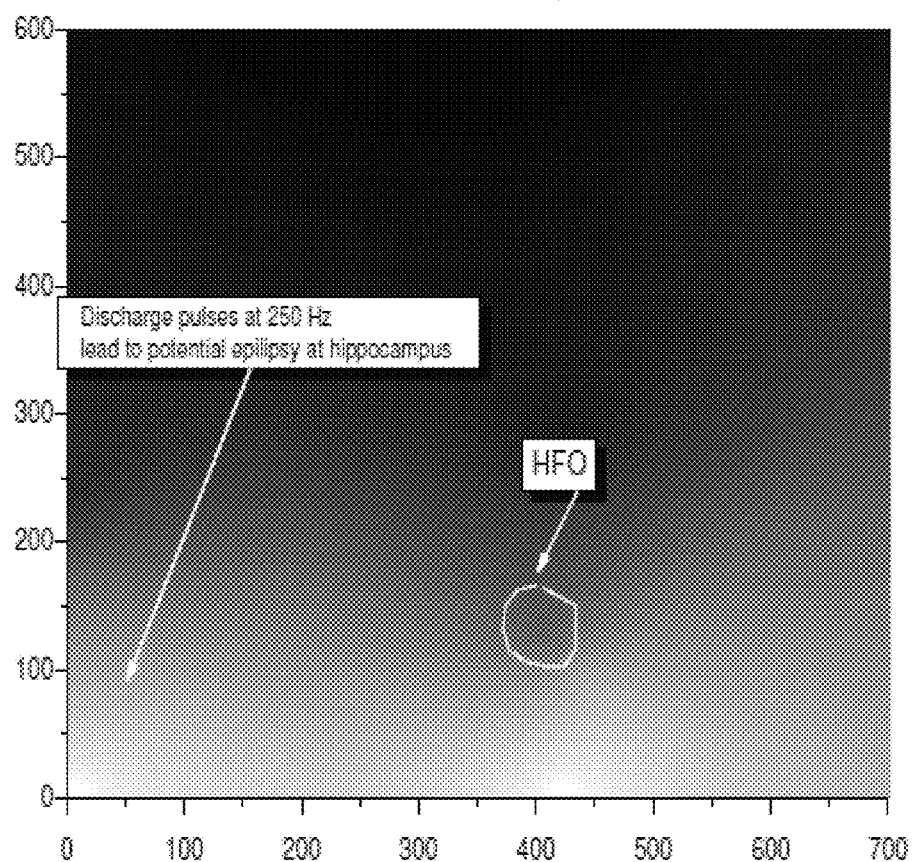

FIG. 25 in the Panel A depicts the synapse circuitry dynamic 3D Energy-Sensory map of Device 2 interacted with NIST serum after discharges synapse pulses and infused the pulse energies into the matrix and labeled as * were shown, and without Aβ as "Epilepsy stage 1" and "asumptomatic". The pHFO were labeled. The e epilepsy point was labeled. The Panel B depicts the contour map with the pHFO were labeled. The Panel C depicts the optical image of the Energy-Sensory map. The pHFO was labeled in the optical image.

Figure 26:
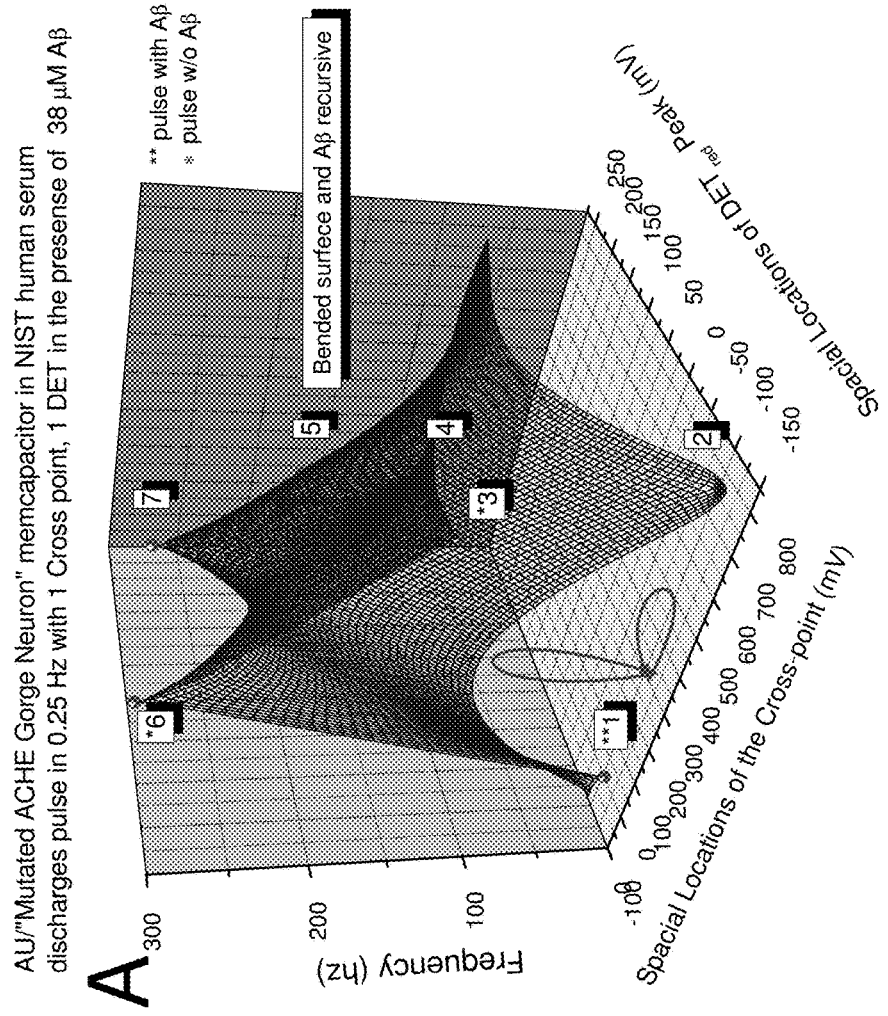
Figure 26:
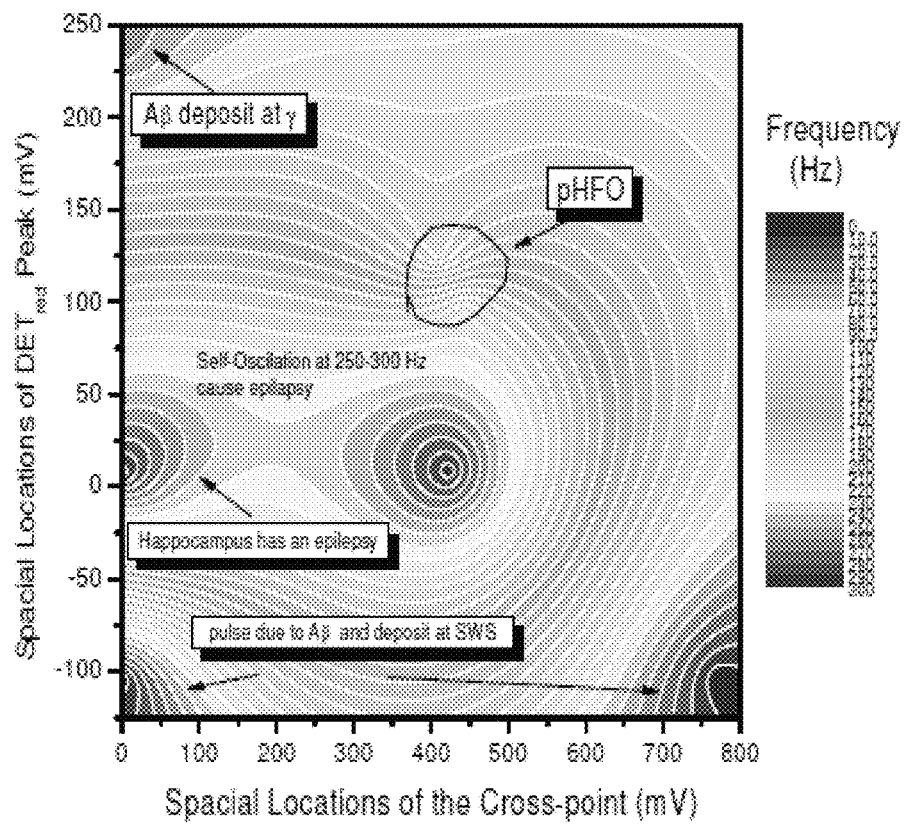
Figure 26:
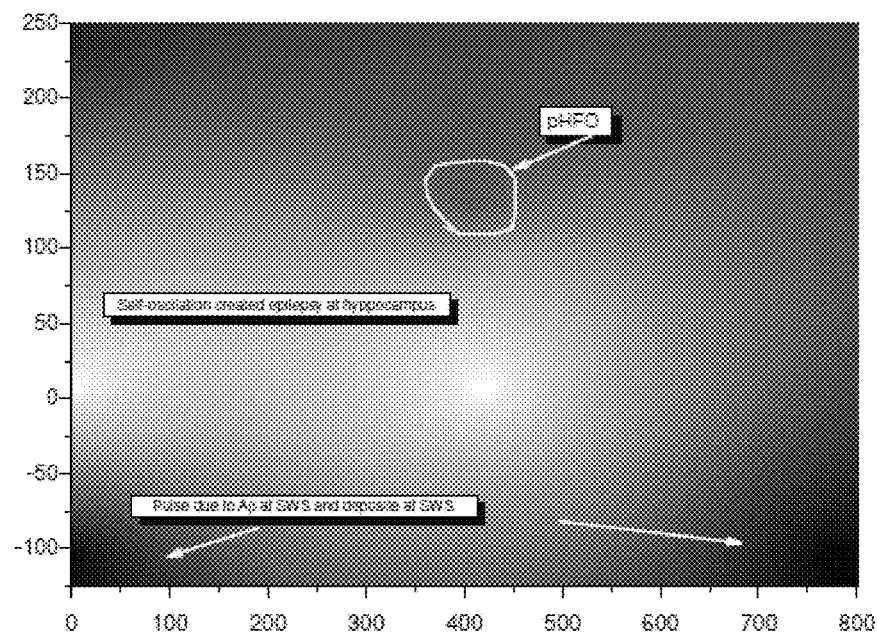

FIG. 26 in the Panel A depicts the synapse circuitry dynamic 3D Energy-Sensory map of Device 2 interacted with NIST serum after discharges synapse pulses and infused the pulse energy with 38 μM Aβ at SWS Hz into the matrix as **, other discharge pulses infused in the matrix in higher frequencies without Aβ, and labeled as * were shown. The pHFO were labeled, as "Epilepsy stage 2" and is "asymptomatic". The epilepsy site was labeled. The Aβ reentrant sport was identified. The Panel B depicts the contour map with the pHFO were labeled as the "weak sport" of draining energy. The epilepsy site was labeled. The Aβ depositions were labeled as arrows. The Panel C depicts the optical image of the Energy-Sensory map. The pHFO was labeled in the optical image.

Figure 27:
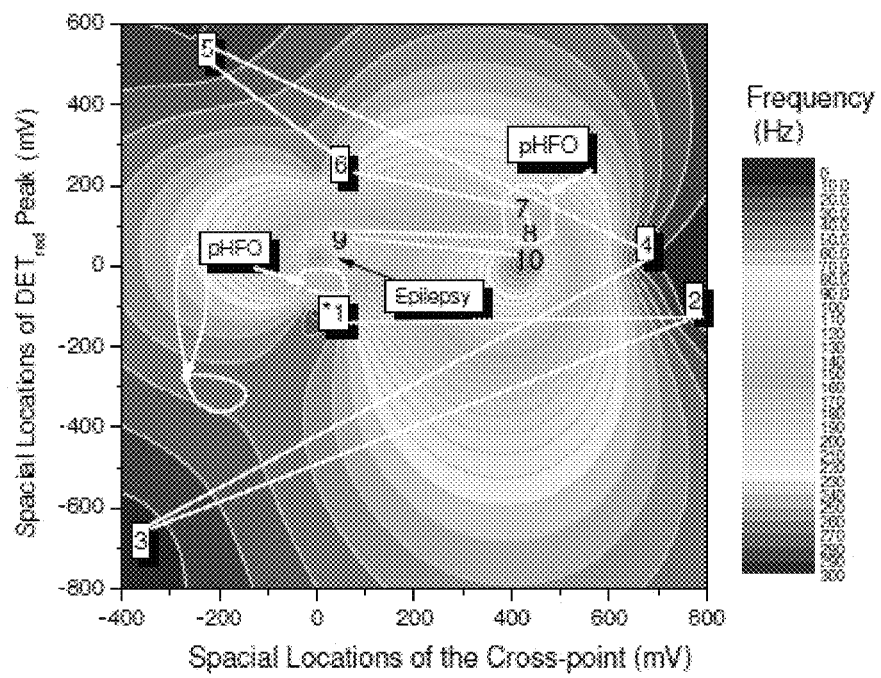
Figure 27:
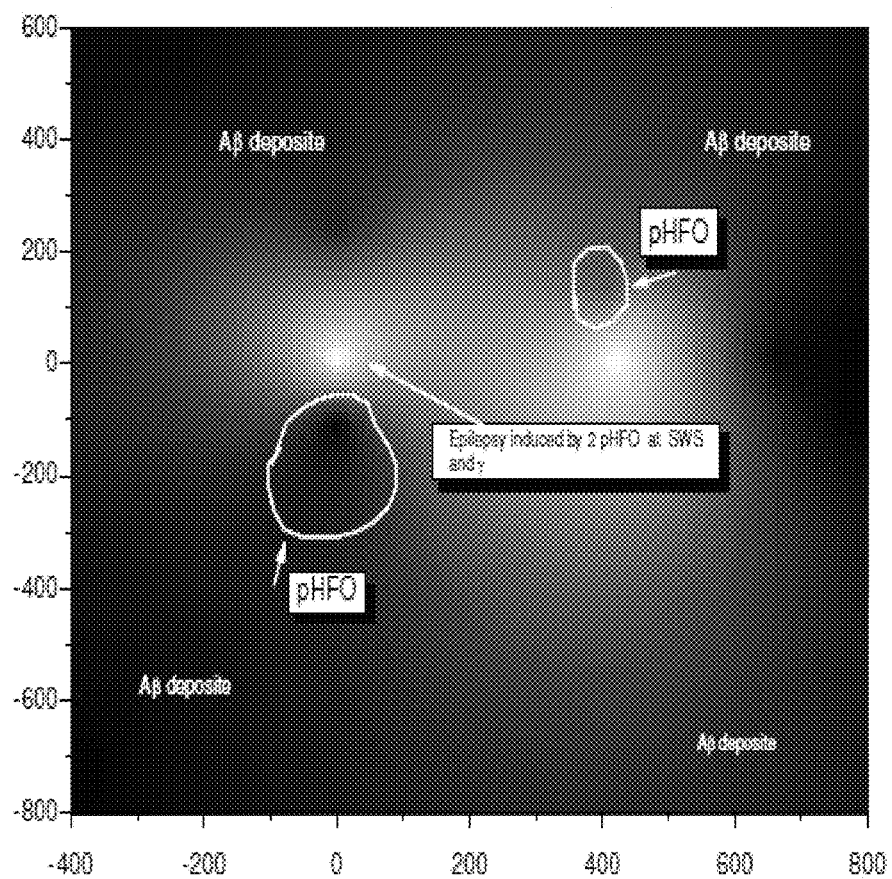

FIG. 27 in the Panel A depicts the synapse circuitry dynamic 3D Energy-Sensory map of Device 2 interacted with NIST serum after discharges a synapse pulse at 0.25 Hz, and infused the pulse energy under the condition of with 38 μM Aβ into the matrix as a * and the neural network prosthesis built under the same concentration of Aβ from 1 to 10 Hz with 2 DET peaks and 2 cross-point locations at each frequency; DET and cross-point CV data from 40 Hz to 300 Hz have no Aβ, so same as to the discharge pulses infused in the matrix, without Aβ. The 2 pHFO inducing centers were labeled. This is "Epilepsy stage 3" and is "symptomatic". The Aβ reentrant center was labeled. The epilepsy site was labeled. The Panel B depicts the contour map with the pHFO were labeled as the "weak sport" of draining energy. The epilepsy site was labeled. The Aβ depositions were shown as the dark blue colors. The Panel C depicts the optical image of the Energy-Sensory map. The pHFO was labeled in the optical image. The epilepsy center was labeled. Aβ depositions were labeled.

Figure 28:
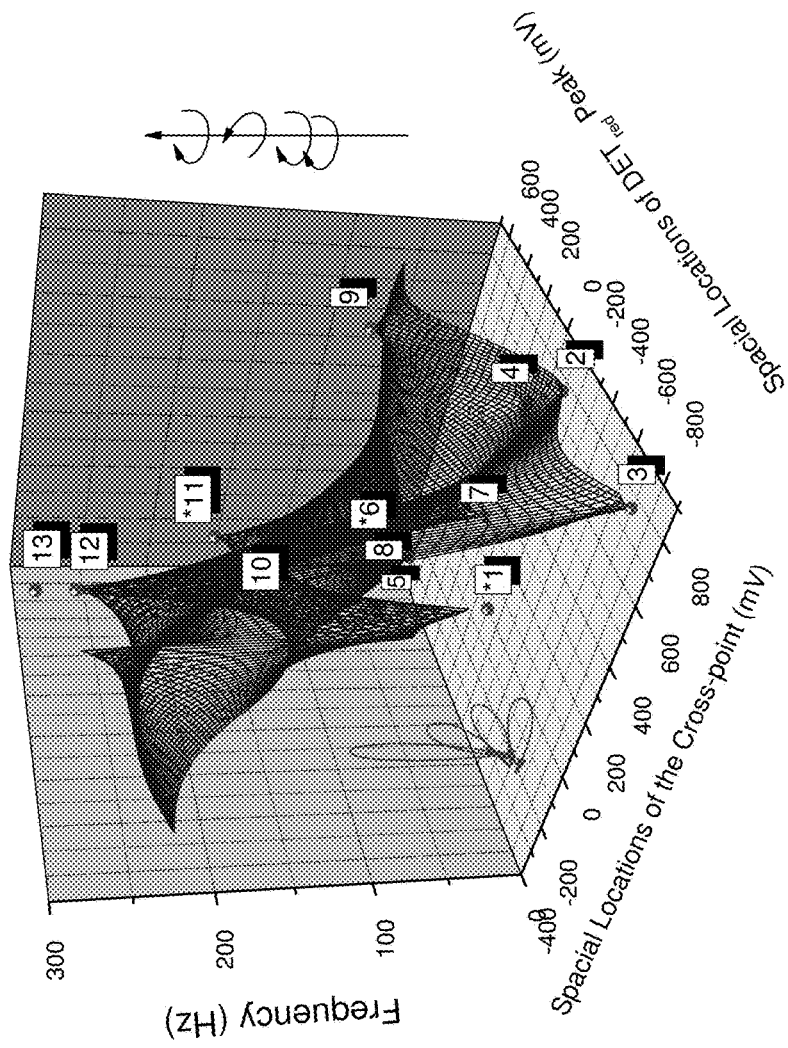
Figure 28:
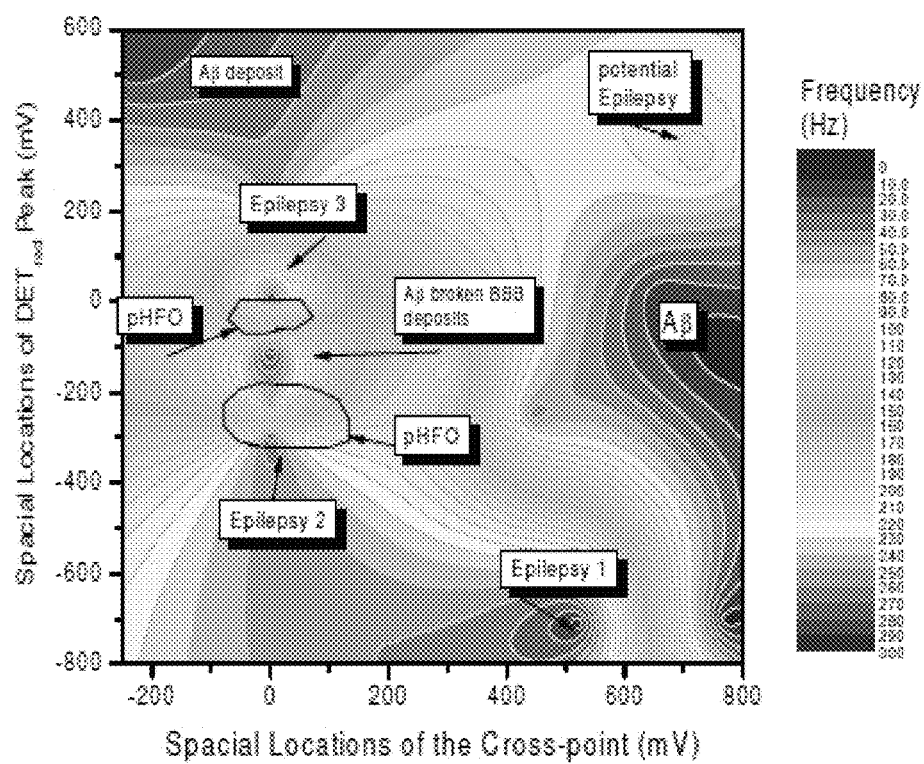
Figure 28:
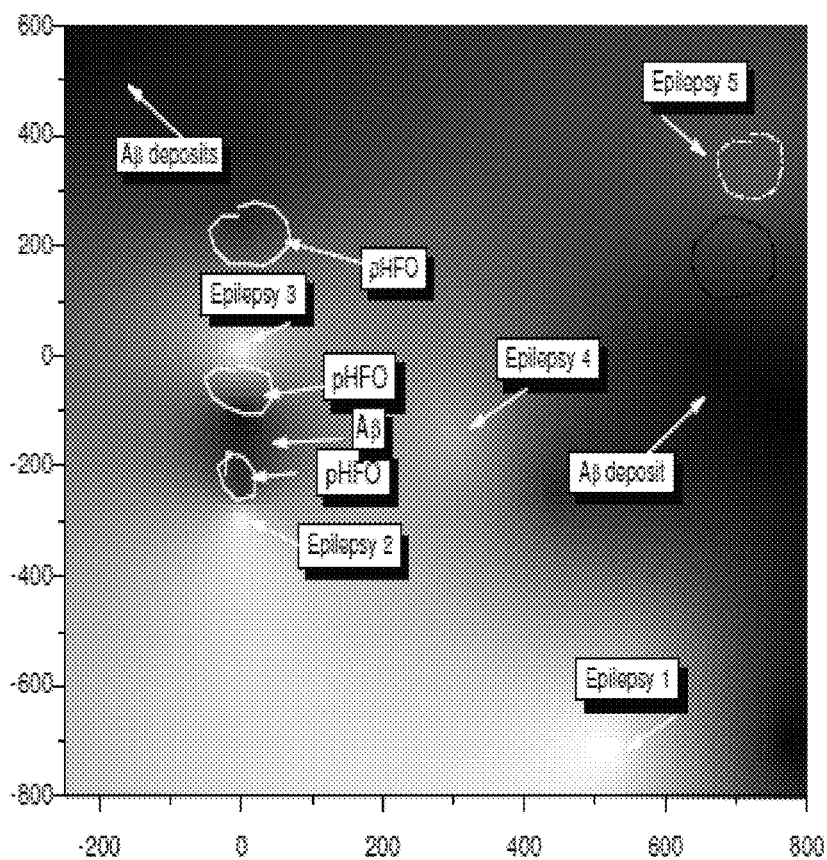

FIG. 28 in the Panel A depicts the synapse circuitry dynamic 3D Energy-Sensory map of Device 2 interacted with NIST serum after discharges a synapse pulse at 0.25 Hz, and infused the pulse energy under the condition of with 38 μM Aβ at 0.25, 40 and 300 Hz into the matrix as a * and the neural network prosthesis built under the same concentration of Aβ over 1 to 300 Hz with multiple DET peaks and multiple cross-point locations at this range. This is "Epilepsy stage 4A" and is life "threatening symptomatic". The Aβ multiple reentrant centers were labeled. The Panel B depicts the contour map with the pHFO were labeled as the "weak sport" of draining energy. The epilepsy sites were labeled. The Aβ depositions were shown as the dark blue colors. The Panel C depicts the optical image of the Energy-Sensory map with the pHFO were labeled in the optical image. The epilepsy centers were labeled. Aβ depositions were labeled.

Figure 29:
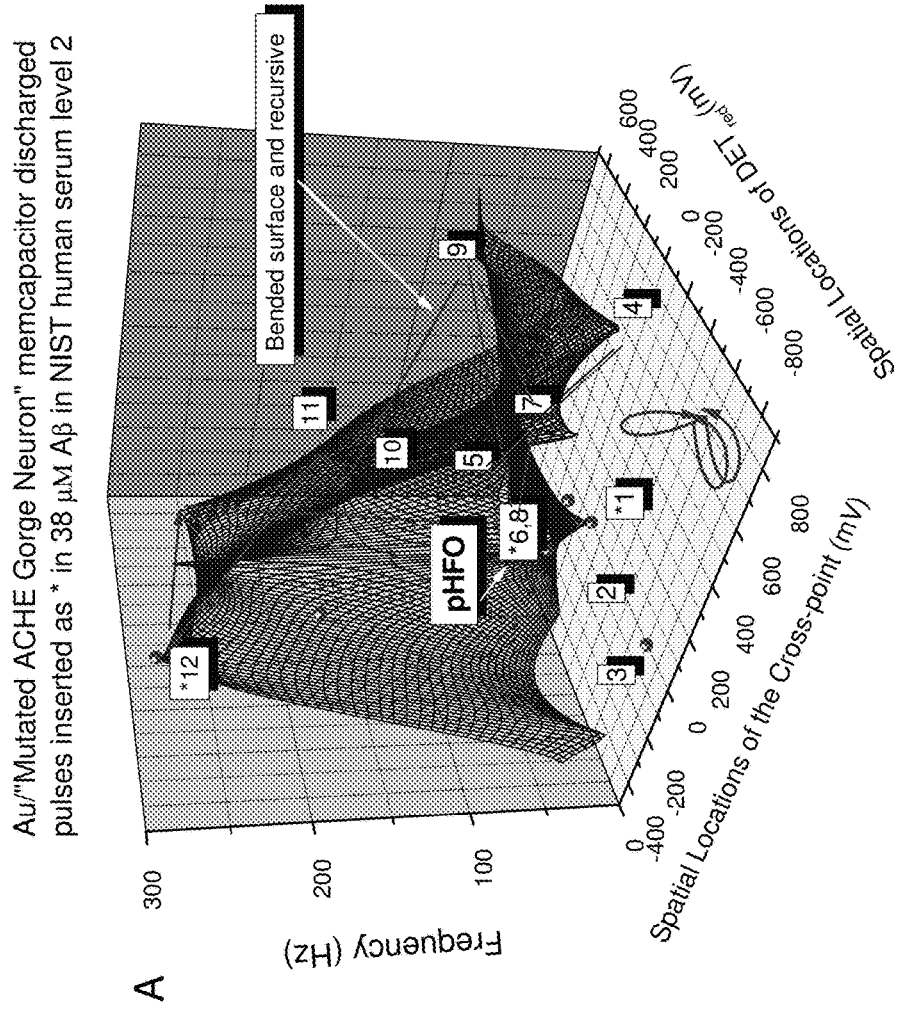
Figure 29:
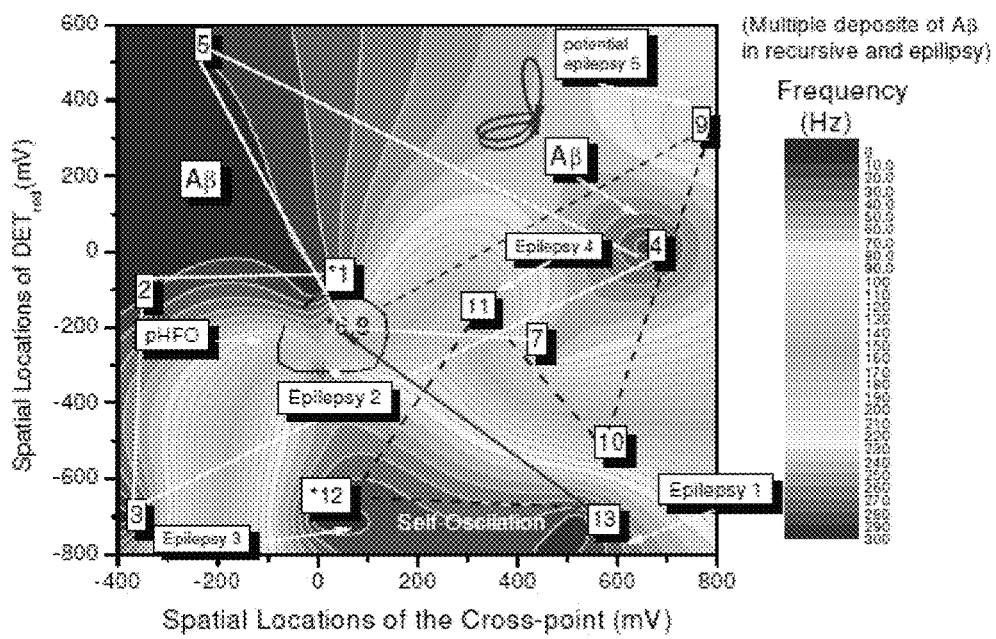
Figure 29:
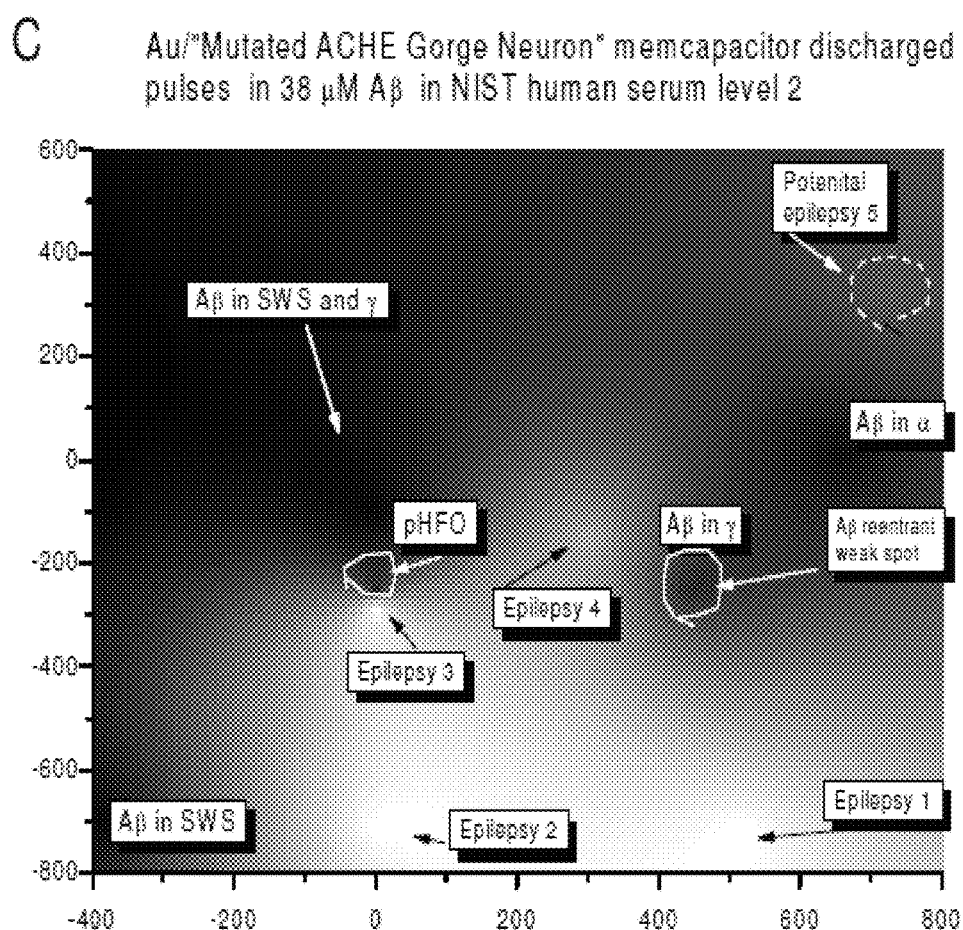
Figure 29:
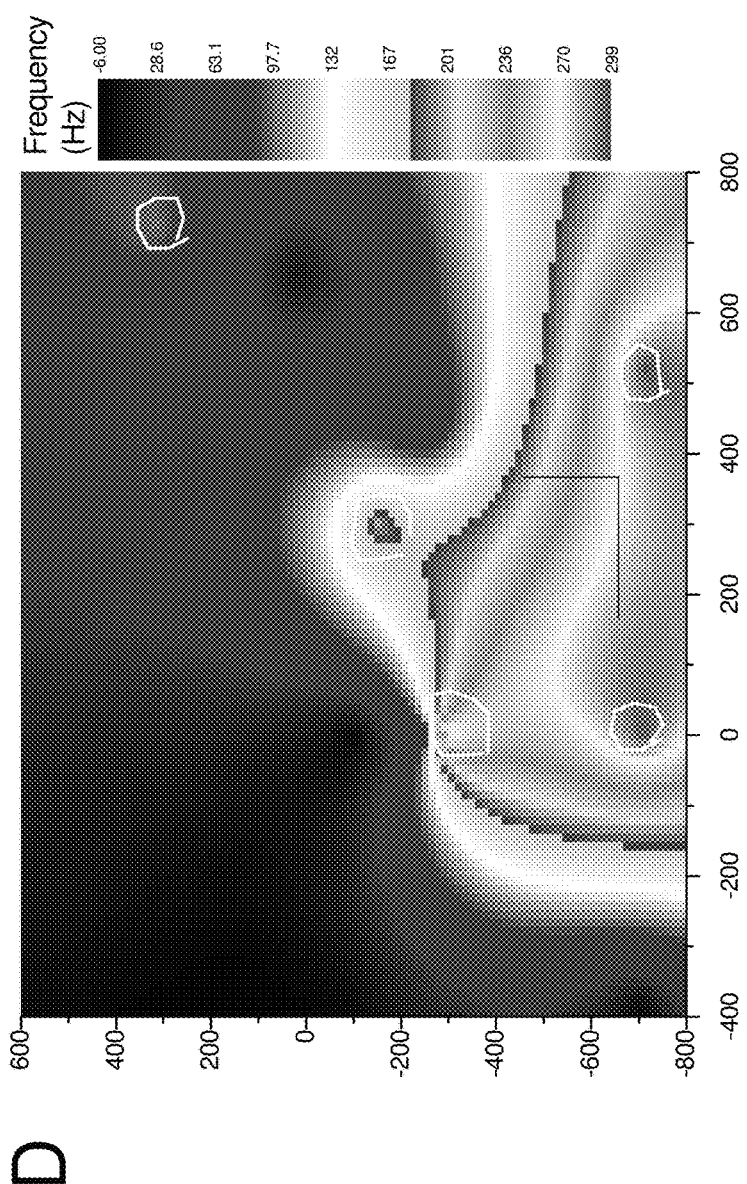

FIG. 29 in the Panel A depicts the synapse circuitry dynamic 3D Energy-Sensory map of Device 2 interacted with NIST serum under the condition of with 38 μM Aβ after discharges a synapse pulse at 0.25, 40 and 250 Hz, respectively, and infused the pulse energies into the matrix as a * and the neural network prosthesis built under the same concentration of Aβ over 1 to 300 Hz with multiple DET peaks and multiple cross-point locations at this range. This is "Epilepsy stage 4B" and is life "threatening symptomatic". The Aβ multiple reentrant centers were labeled. The Panel B depicts the contour map with the pHFO was labeled as the "weak sport" of draining energy. The epilepsy sites were labeled. The Aβ depositions were shown as the dark blue colors. The Panel C depicts the black-white optical image of the Energy-Sensory map with the pHFO were labeled in the optical image. The 5 epilepsy centers were labeled. Aβ depositions were labeled. The Panel D depicts the colorful optical image of the Energy-Sensory about the spatiotemporal trajectory using neither a tracer nor a dye.

Figure 30:
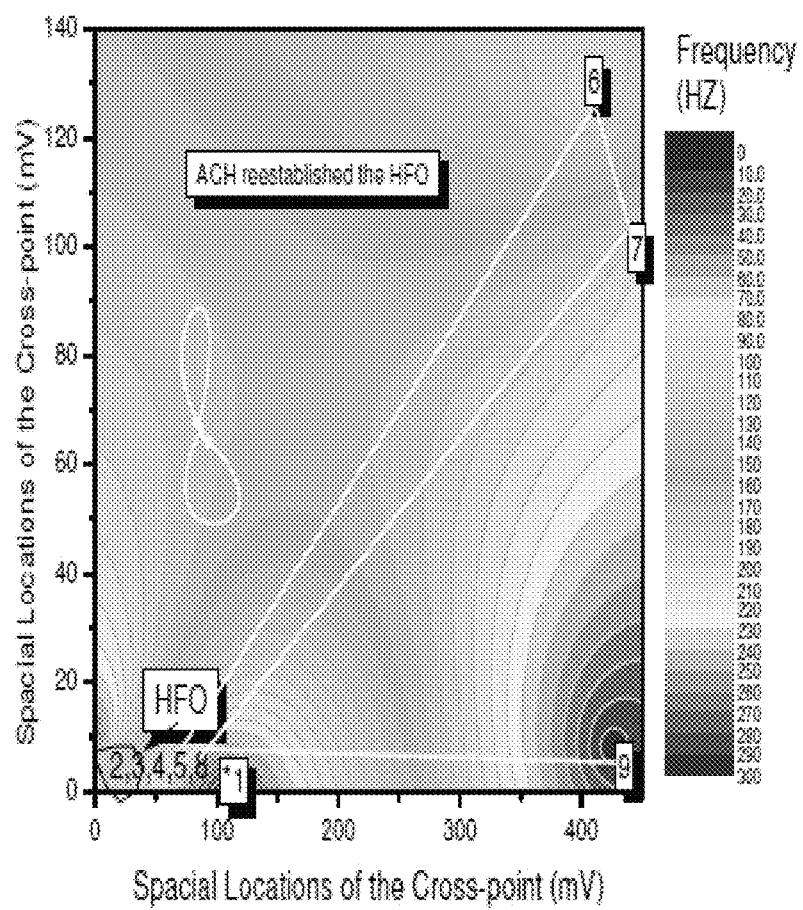
Figure 30:
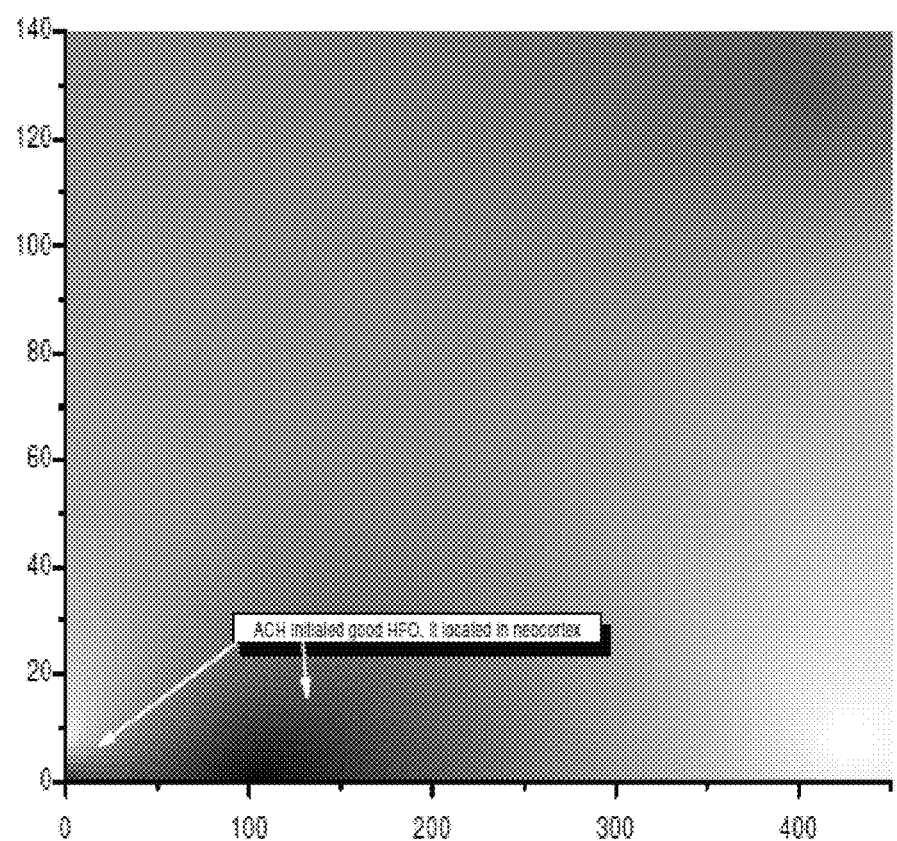

FIG. 30 Panel A depicts the synapse circuitry dynamic 3D Energy-Sensory map of Device 2 interacted with NIST serum after discharges synapse pulses and infused the pulse energy under the condition with 38 μM Aβ and 15 nM ACH at 0.25, 40 Hz and 250 Hz, respectively into the matrix as *, shown as "Early recovery" to repair a level 2.5 "epilepsy" or AD. The brain network prosthesis was made from the CV data with the same concentration of Aβ and ACH over 1-40 Hz, except the 2 mM o-NPA also presence in the solutions in 10 and 40 Hz, respectively. The CV data obtained to build the brain prosthesis from 100-300 Hz there was no reagent was present, only pure NIST serum with the assumption of Aβ will not be able to penetrate from nerocortex into the hippocampus area at an early stage of AD or epilepsy. The positive memory reentrant was labeled. There were no multiple DET and multiple cross-points in the matrix. The Panel B depicts the contour map with the HFO labeled. The Panel C depicts the optical image of the Energy-Sensory map. The HFO was labeled in the optical image.

Figure 31:
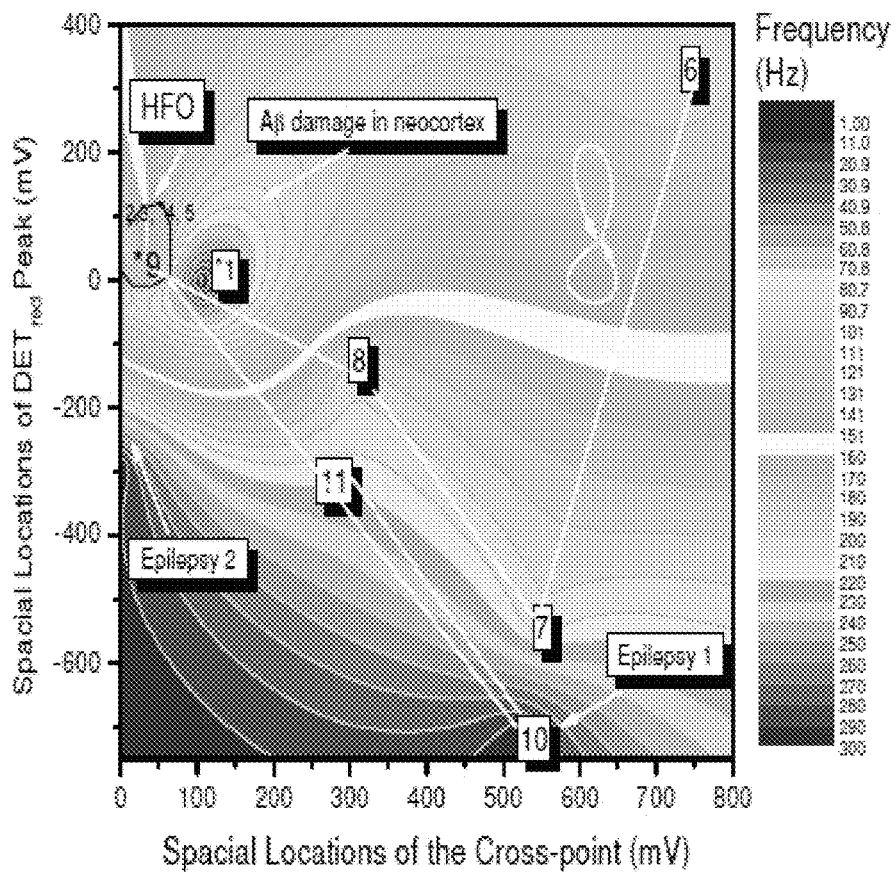
Figure 31:
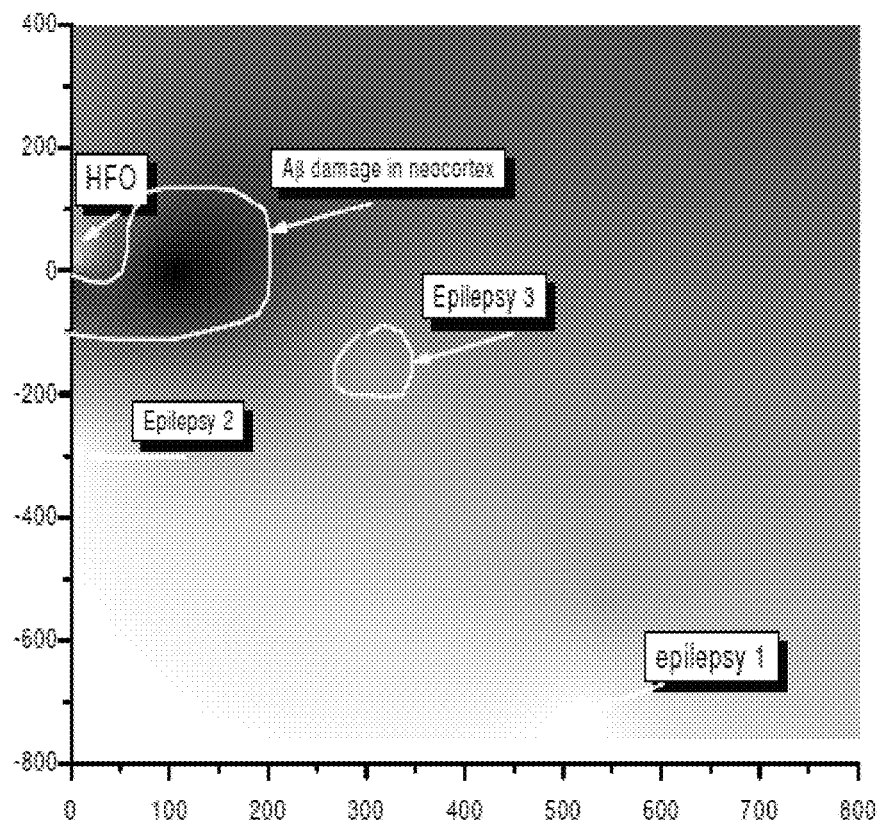

FIG. 31 the Panel A depicts the synapse circuitry dynamic 3D Energy-Sensory map of Device 2 interacted with NIST serum after discharges synapse pulses and infused the pulse energy under the condition with 38 μM Aβ and 15 nM ACH at 0.25, 40 Hz and 250 Hz, respectively into the matrix as *, shown as "Early recovery" on "Epilepsy stage 4A" or AD.

The brain network prosthesis was made from the CV data with the same concentration of Aβ and ACH over 1-40 Hz, except the 2 mM o-NPA also presence in the solutions in 10 and 40 Hz, respectively. The CV data obtained to build the brain prosthesis from 100-300 Hz with 38 µM Aβ. There were multiple DET and multiple cross-points in the matrix. The Panel B depicts the contour map with the HFO labeled. Epilepsy centers were also labeled. The Panel C depicts the optical image of the Energy-Sensory map. The HFO was labeled in the optical image. The epilepsy centers were labeled.

Figure 32:
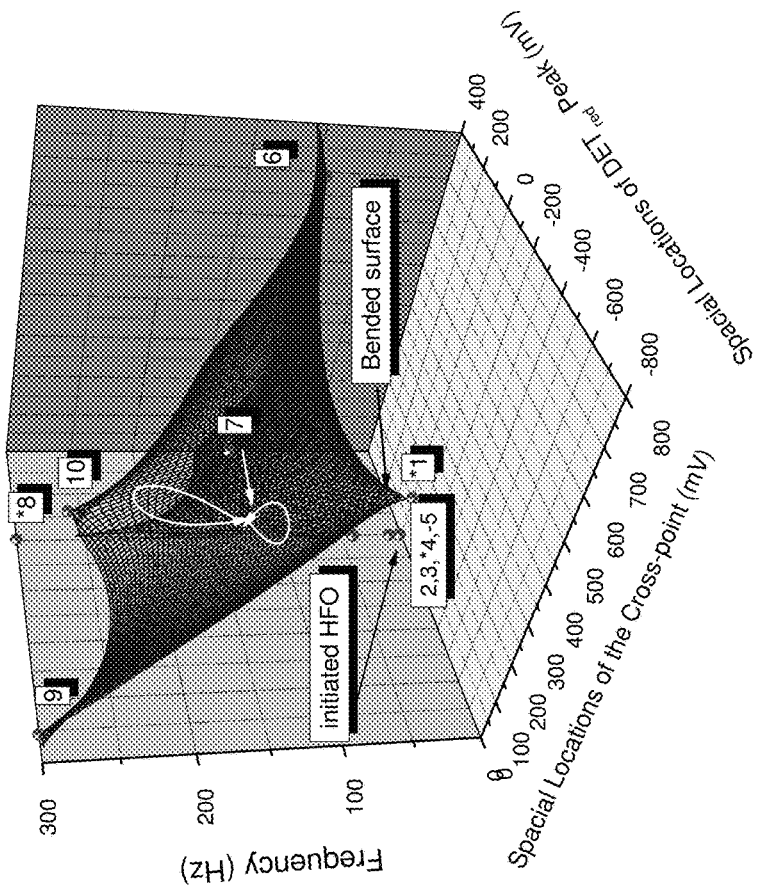
Figure 32:
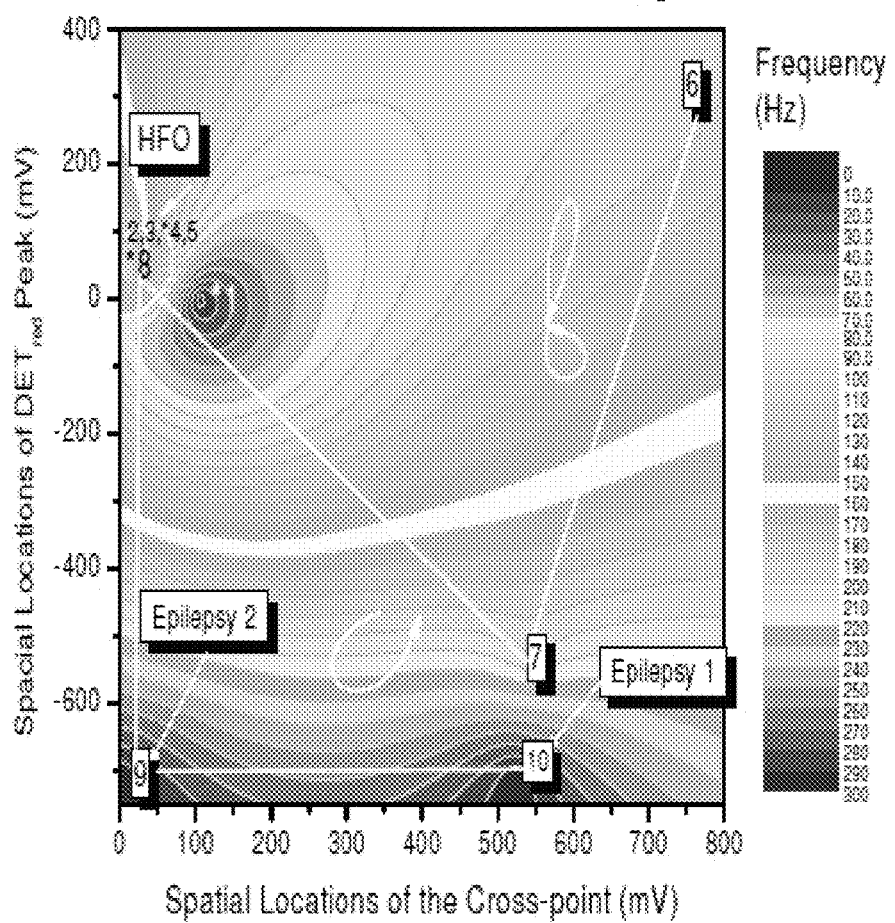
Figure 32:
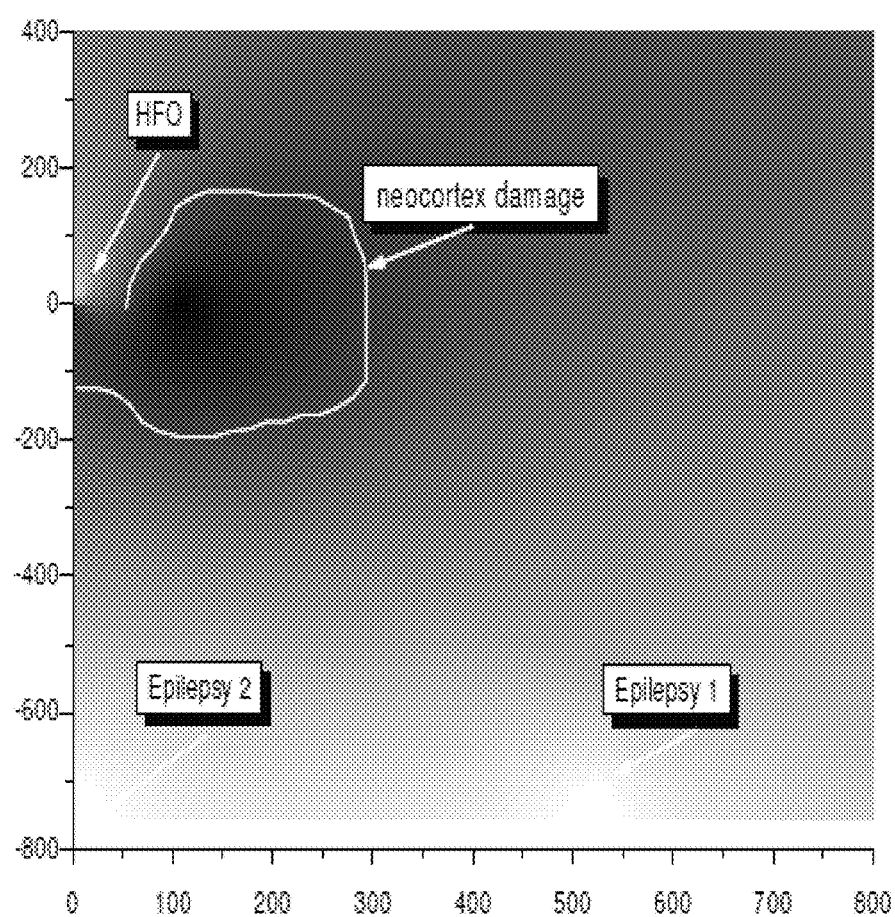

FIG. 32 the Panel A depicts the synapse circuitry dynamic 3D Energy-Sensory map of Device 2 interacted with NIST serum after discharges synapse pulses and infused the pulse energy under the condition with 38 µM Aβ and 15 nM ACH at 0.25, 40 Hz and 250 Hz, respectively into the matrix as *, shown as "Early recovery" on "Epilepsy stage 4B" or AD. The experimental conditions and explanations are same as above section. The Panel B depicts the contour map with the HFO labeled. Epilepsy centers were also labeled. Panel C depicts the optical image of the Energy-Sensory map. The HFO was labeled in the optical image. The epilepsy centers were labeled.

FIG. 33 depicts the linear least-square regressions of energy density vs. time for with and without Aβ, respectively for Device 1 in NIST human serum specimens. The Panel A depicts the conditions of NIST serum only without spiking Aβ covered the time from 0.004 to 4 s. The Panel B under the conditions with 3.8 nM Aβ, the Panel C with 76 nM Aβ, the Panel D with 151 nM Aβ and the Panel E with 471 nM Aβ.

DETAILED DESCRIPTION OF THE INVENTION

Example 1—Fabrication of the Nanostructured Biomimetic Self-Assembling Membranes (SAM)

The nanostructured biomimetic ACHE SAM with the vertical bridged conformational "Mutated ACHE Gorge" was freshly prepared. Polyethylene glycol diglycidyl ether (PEG), triacetyl-ß-cyclodextrin (T-CD), poly(4-vinylpyridine) (PVP) were purchased from Sigma. PVP was purified before use. The mono derivative dimethyl ß-cyclodextrin named as (mM-ß-DMCD) was generally synthesized according to the published procedures [35]. The appropriate amount of solutions of individual polymer and reagents were prepared [36]. The mixture solution was made up by mM-ß-DMCD (2 g/L to 2.5 g/L, T-CD 2-3 mM, PEG 2 g/L-3 g/L and PVP (40 mg/dL-80 mg/dL), the mixture was incubated in 37 C for 2-3 hrs, then added 0.02M o-NPA with the molar ratio to TCD in the range of (500-1000):1 to the mixture for device 1 with a flat membrane with nanopores. The vertical bridge membrane with nanopores for device 2 did not apply o-NPA. The Au electrode has 50 nm thicknesses and 3 mm in diameter. The mixture solution was injected onto the surface of the electrode and was incubated for 48 hrs at incubator [36]. After that, the further clean and incubating procedures were followed by literature 36.

The nanostructured biomimetic "Normal ACHE Gorge" neuronal network SAM with the flat bridged conformation, nanopores and lattices was freshly prepared by adding appropriate amount of o-nitrophenyl acetate (o-NPA) into the above described mixture solution for construction of the vertical bridged ACHE SAM. All other procedures were followed by literature 36.

Example 2—AFM Measurements

Figure 1A:
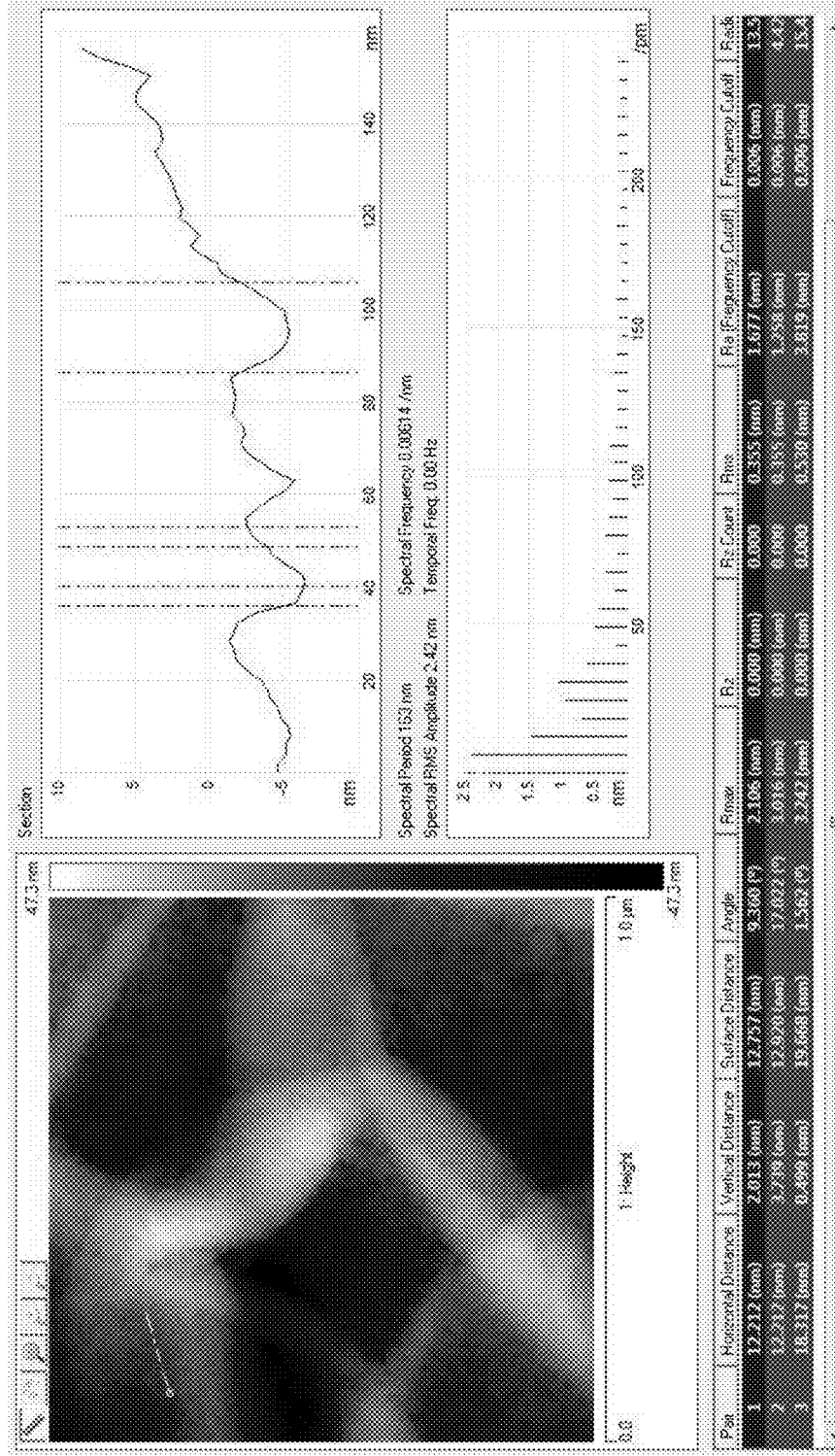
FIG. 1A is a face-to-face view of the three-dimensional atomic force microscopy (AFM) image of the nanostructured "ATP Lid" with a vertical bridge and the cross section analysis results were presented in the table.
Figure 1B:
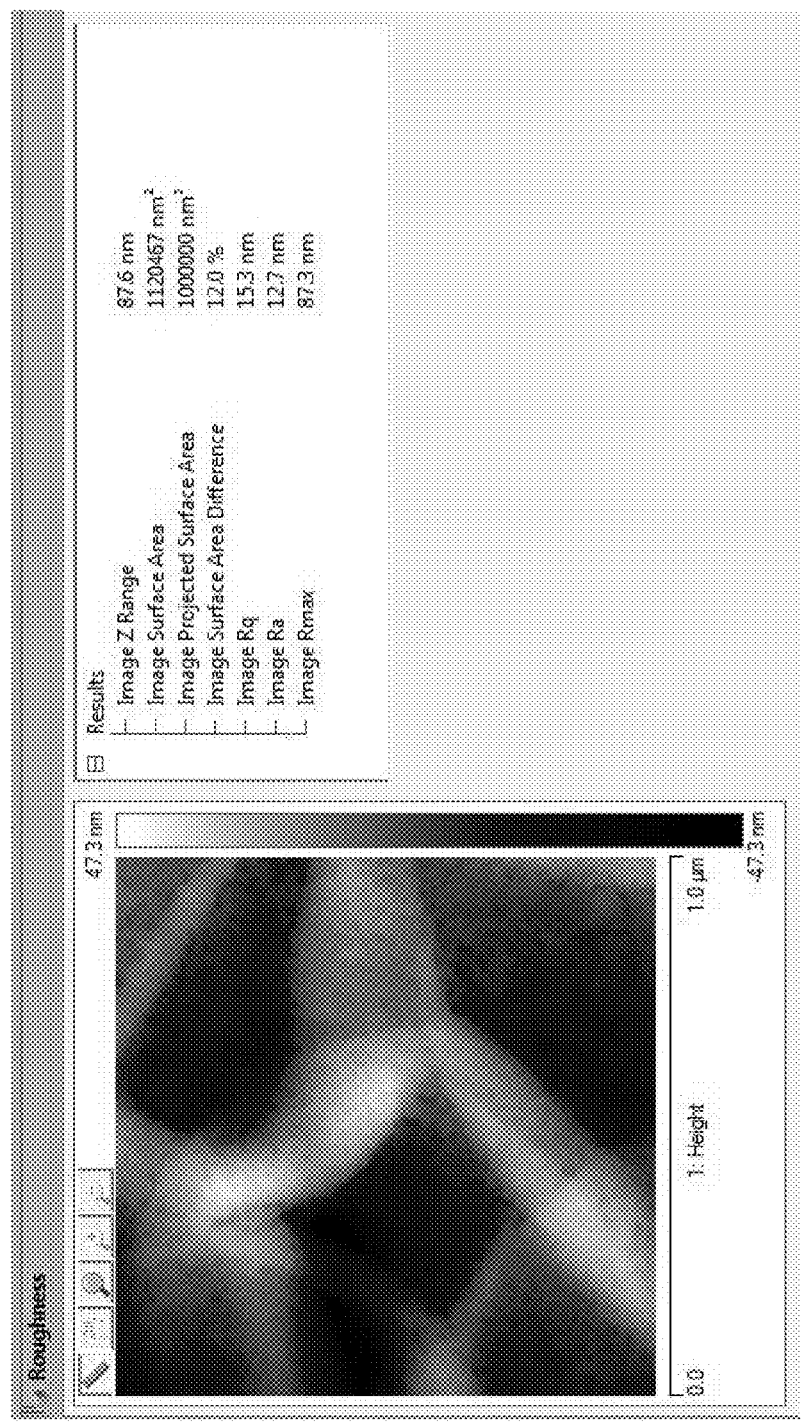
FIG. 1B is a face-to-face view of the vertical bridge with the AFM results in membrane surface roughness measurements in Peak-to-Valley (Z range), and the Root Mean Square (RMS), and Average Roughness ($R_a$) were shown in the results table that are corresponding to this image.
Figure 1C:
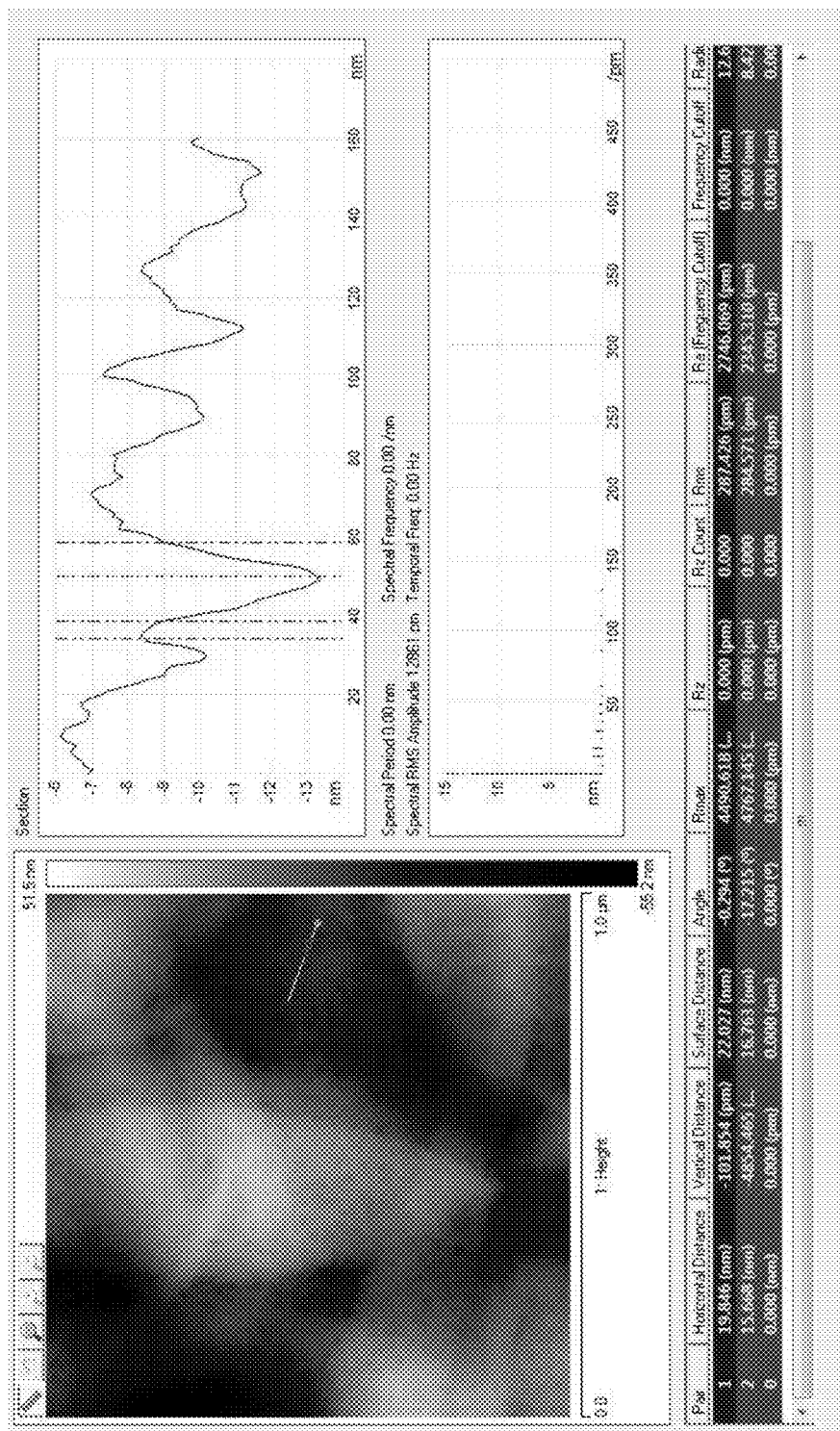
FIG. 1C is a side view of the vertical bridge as shown in the 2D AFM image with the bridge deepness in cross section analysis.
Figure 1E:
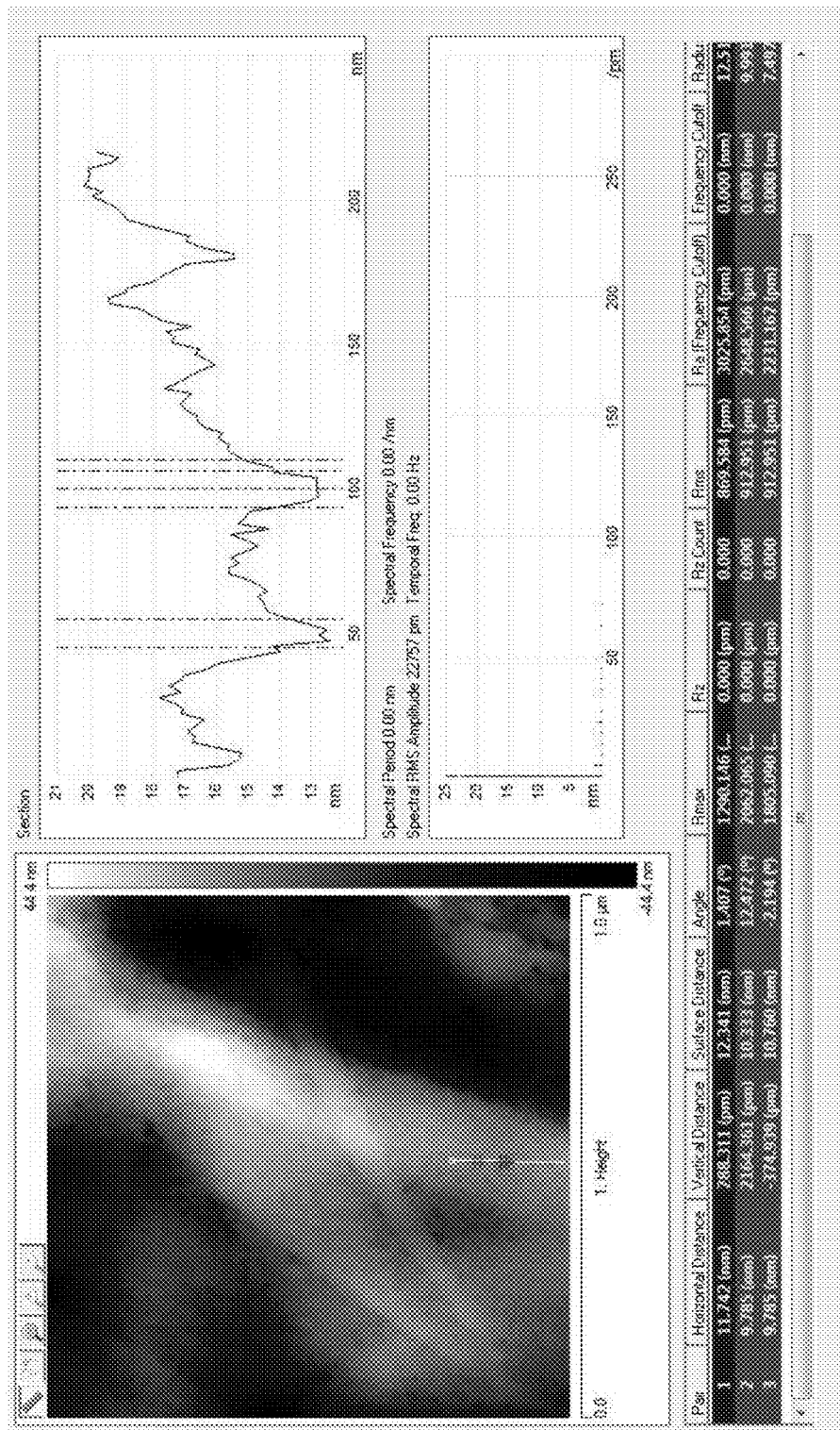
FIG. 1E is a bird-view of the enlarged AFM image of the horizontal bridge surface with the cross-section analysis and FIG. 1F is the AFM specifications results of the horizontal bridge membrane surface based on the bird-view.
Figure 1F:
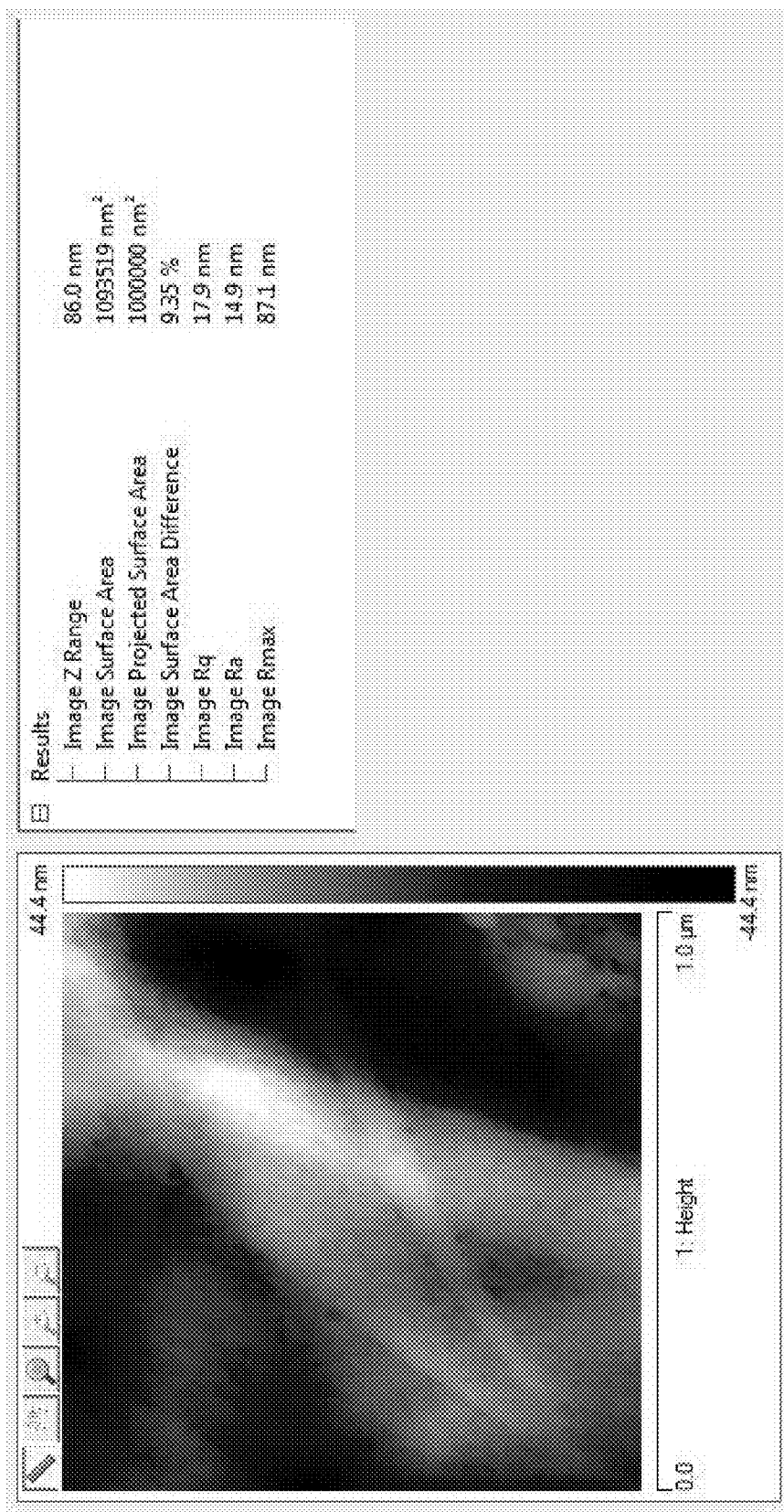
Figure 1G:
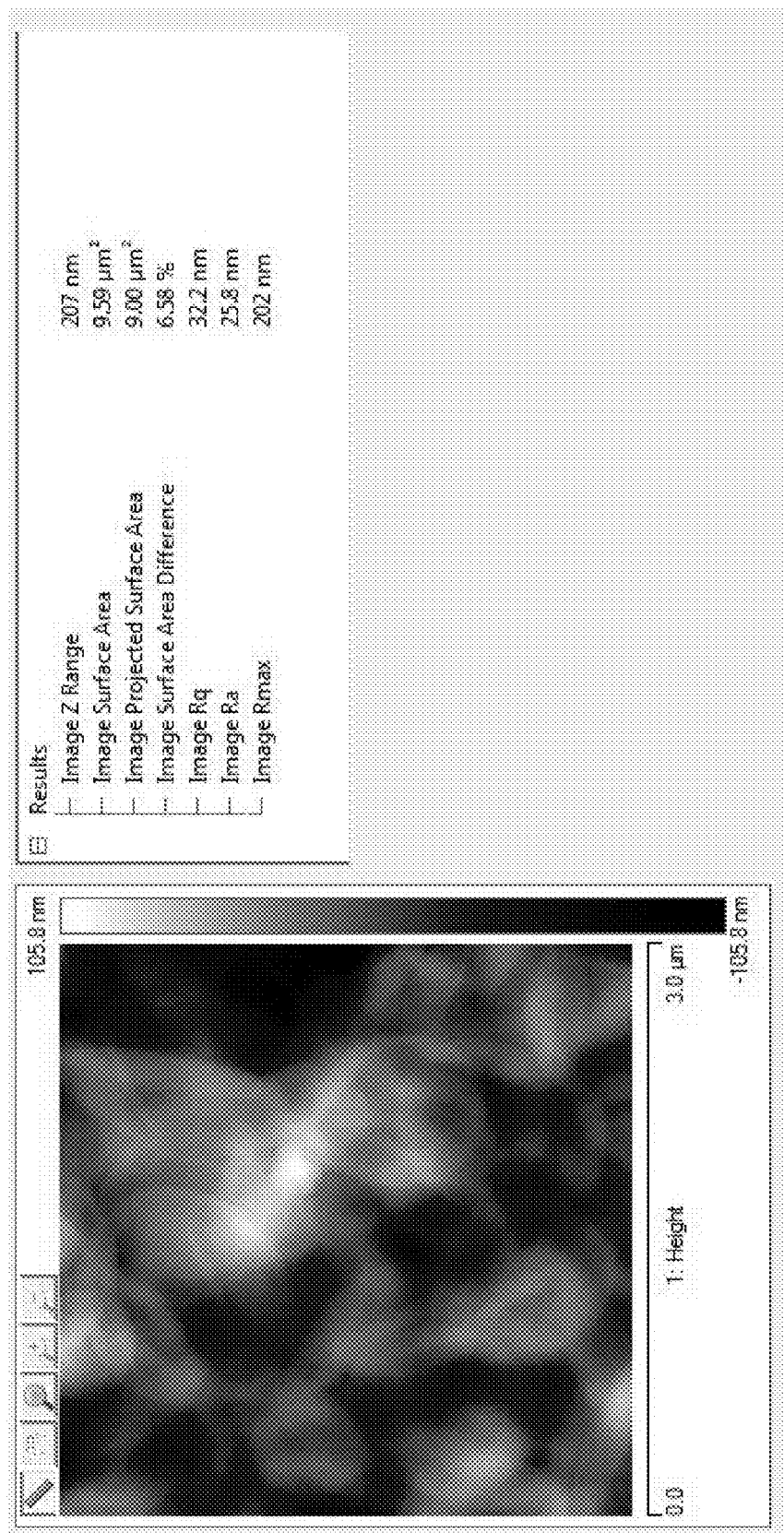
FIG. 1G is a bird-view of the vertical bridge and the underneath arrayed lattices in 9 μM² large area. The results of the specifications of the large area view of the membrane roughness are presented.

The morphology of the three CD-SAMs were characterized by using an instrument (model Multimode 8 ScanAsyst, Bruker, PA). Data collected in PeakForce Tapping Mode. Probes used were ScanAsyst-air probes (Bruker, PA). The silicon tips on silicon nitride cantilevers have 2-5 nm radius. The nominal spring constant 0.4 N/m was used. NanoScope Analysis v1.40r2 software was used. FIG. 1A illustrates the vertical conformational AFM image of ACHE bridge structure by cross analysis. The average "breathing pore" vertical height by cross section analysis is 3.74 nm with the pore width of 12.2-18 nm and the RMS (surface morphology) is 3.55 nm. The lattice distributed pores can be seen in the image. The bridge vertical height is 47.3 nm with the length of 940 nm. FIG. 1B illustrates the membrane specifications in roughness is 15.2 nm and the membrane surface thickness is 47.3 nm. FIG. 1C shows the bridge vertically oriented of 51.5 nm, underneath of the bridge is the "breath pore" with pore diameter of 15-20 nm and depth of 0.5 nm and the surface roughness is 0.287 nm. FIG. 1D shows the membrane surface roughness is 17.4 nm. FIG. 1E shows the AFM image of the shining horizontal cross bar associated with the vertical bridge of FIG. 1A. The cross bar channel width is 200-600 nm and height is 44.4 nm, and length is 1100 nm. Underneath of the bridge are "breathing pores" of 0.2 nm in depth and 10-12 nm in diameter with RMS value 0.9 nm. FIG. 1F shows the membrane surface morphology in 17.9 nm. FIG. 1G shows the AFM in a larger window view of 9 µm$^2$ and we can see the breathing pores distributed evenly filled inside of each orderly square lattices and the bridges are on top with a vertical fall difference of 50-100 nm.

Figure 2A:
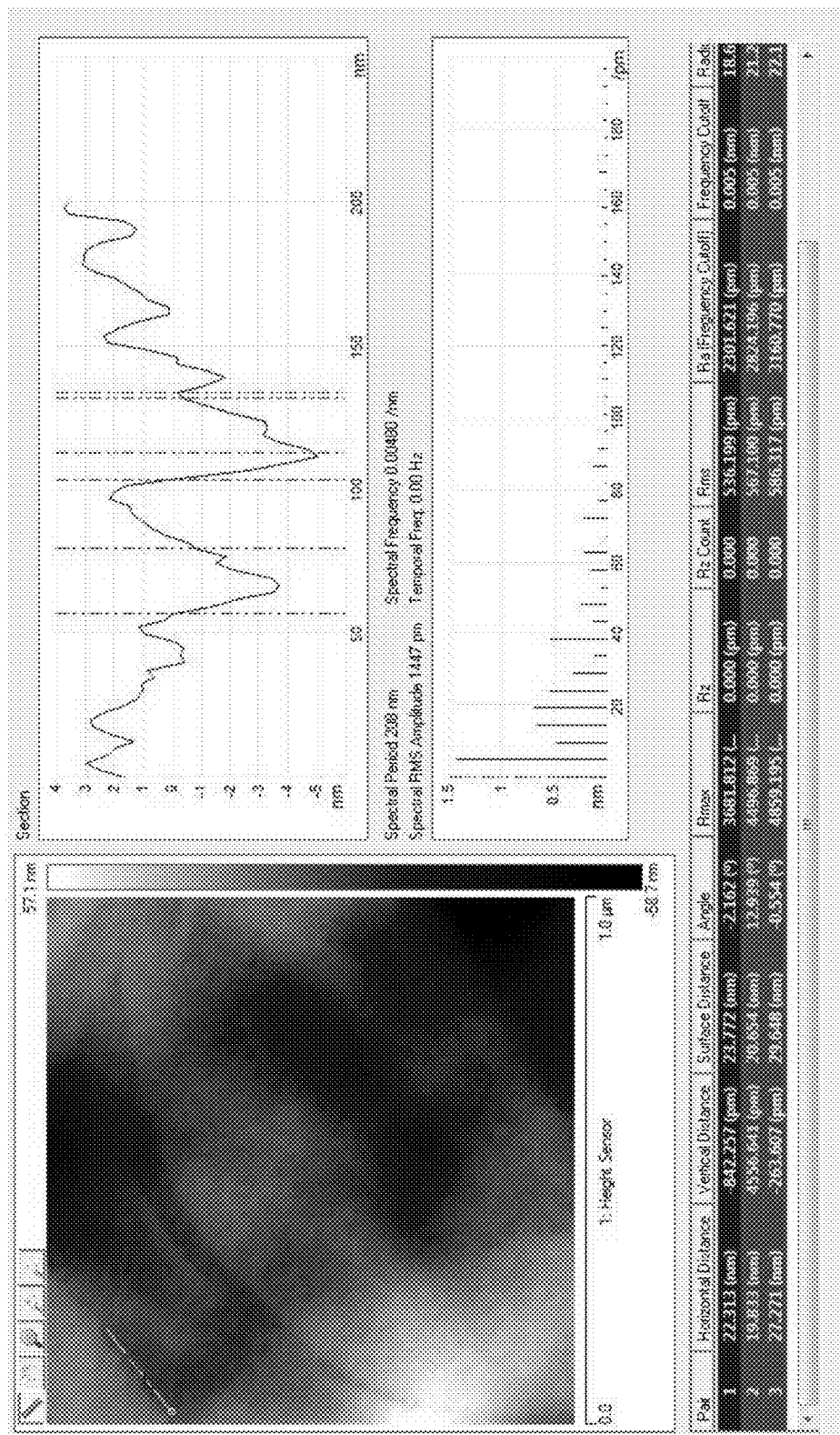
FIG. 2A shows the AFM image of the nanostructured "ATP Lid" with a flat horizontal bridge and the cross section analysis results were shown in the table listed below.
Figure 2B:
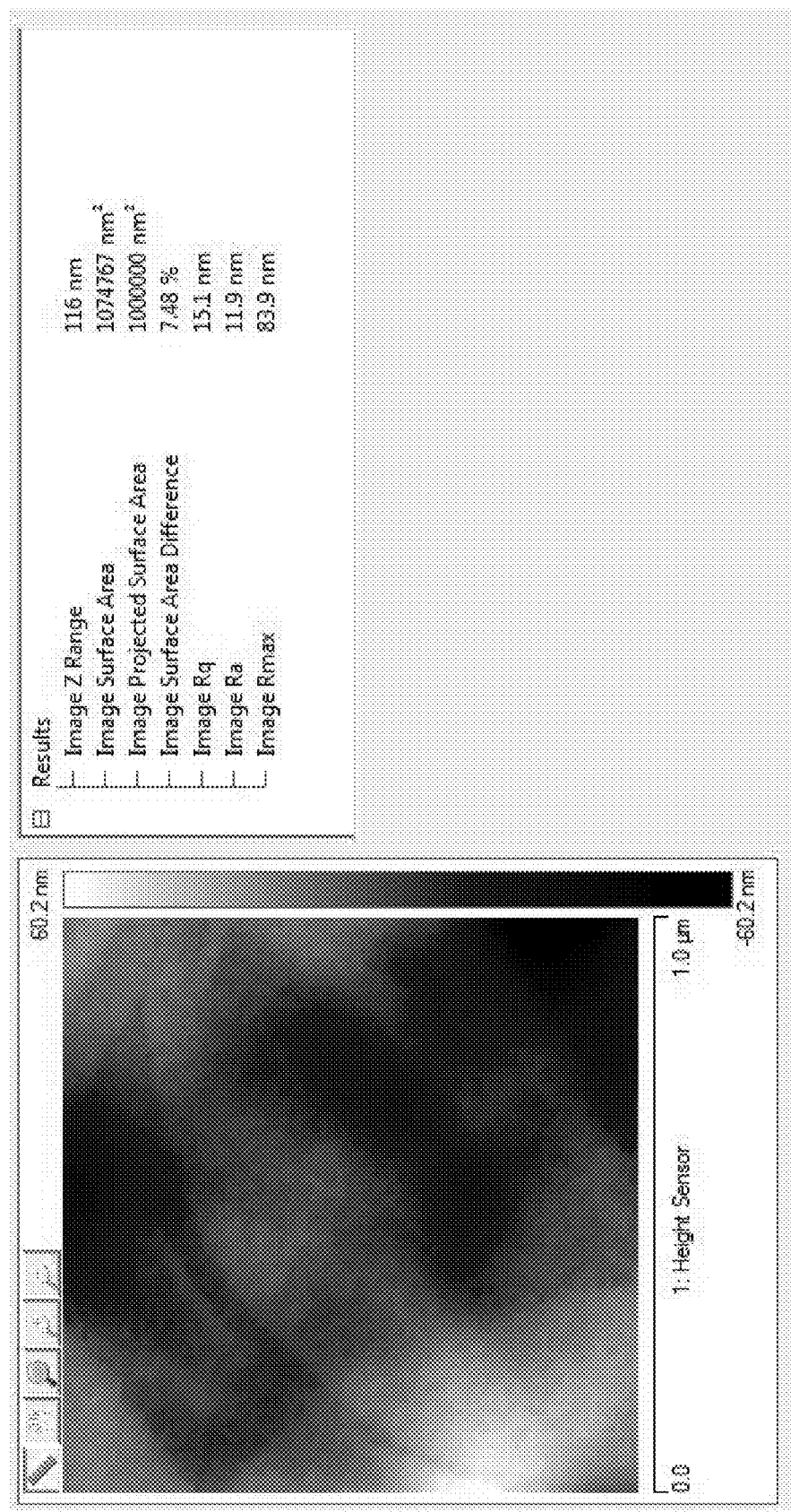
FIG. 2B is the AFM of the "ATP Lid" flat bridge specifications with the roughness values are also shown for this image.
Figure 2C:
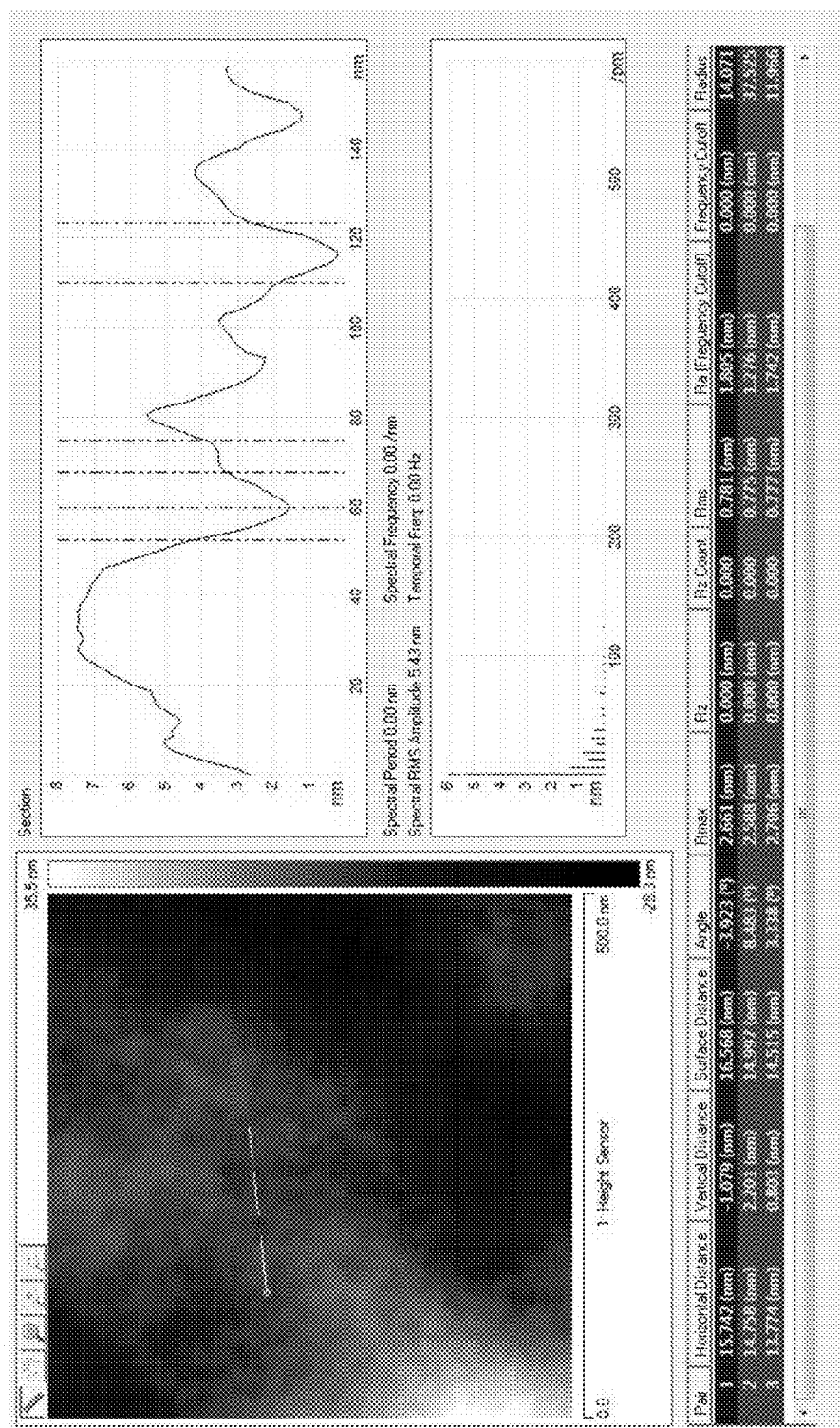
FIG. 2C shows the close look of the bridge surface in cross section analysis.
Figure 2D:
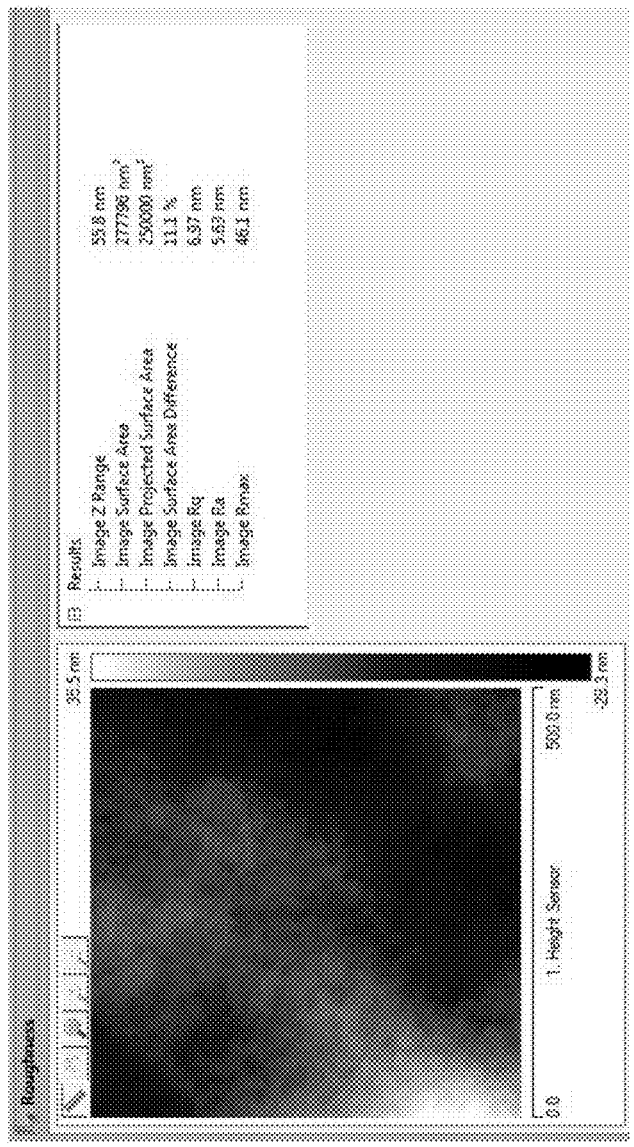
FIG. 2D shows the AFM specification of the surface roughness of the horizontal bridge with the 3D image of the flat "ATP Lid".
Figure 2E:
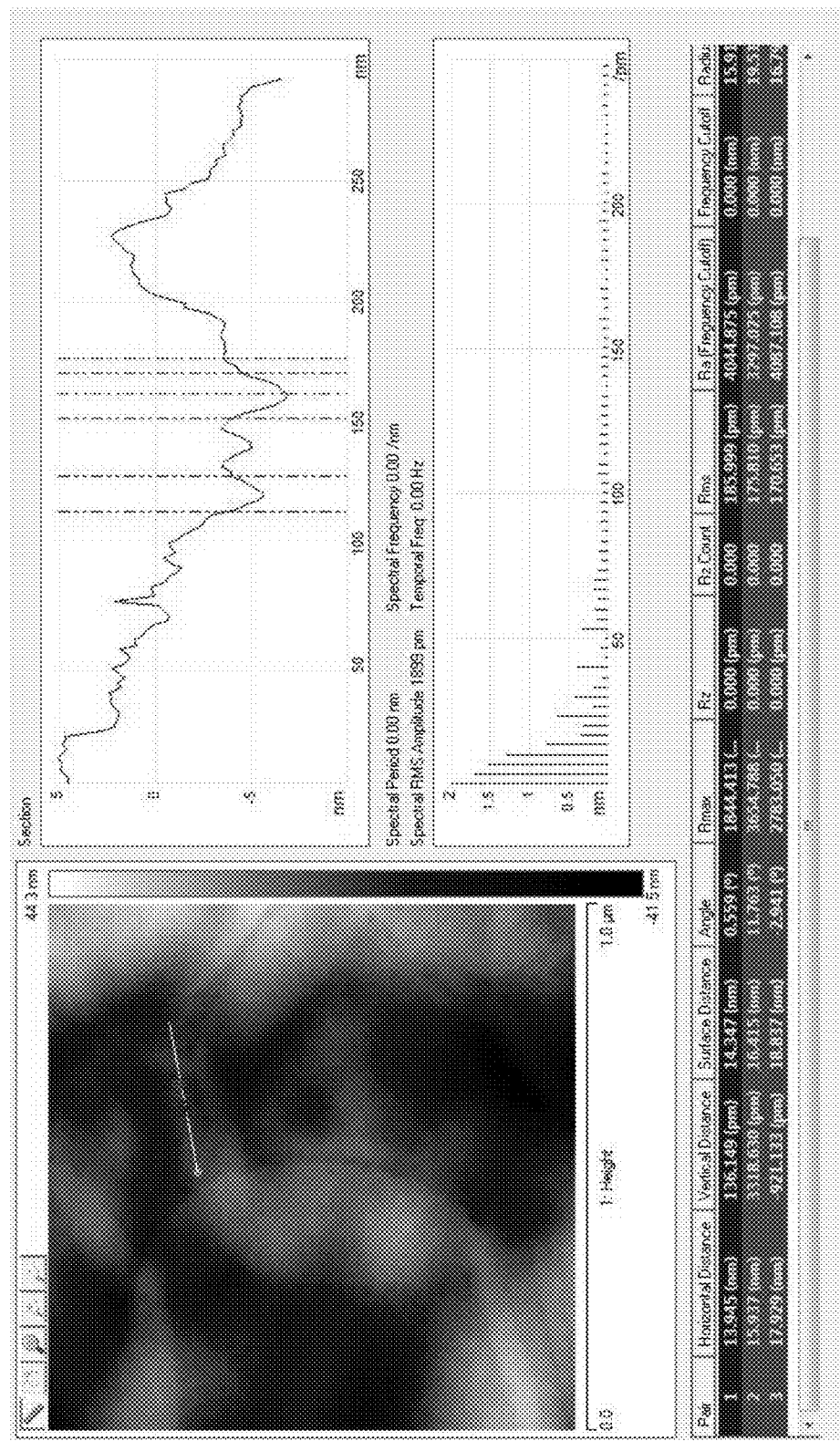
FIG. 2E shows the enlarged AFM of the "Breathing-pore" nearby the bridge for the cross-section analysis and FIG. 2F is the AFM specifications of the "Breathing-pore".
Figure 2F:
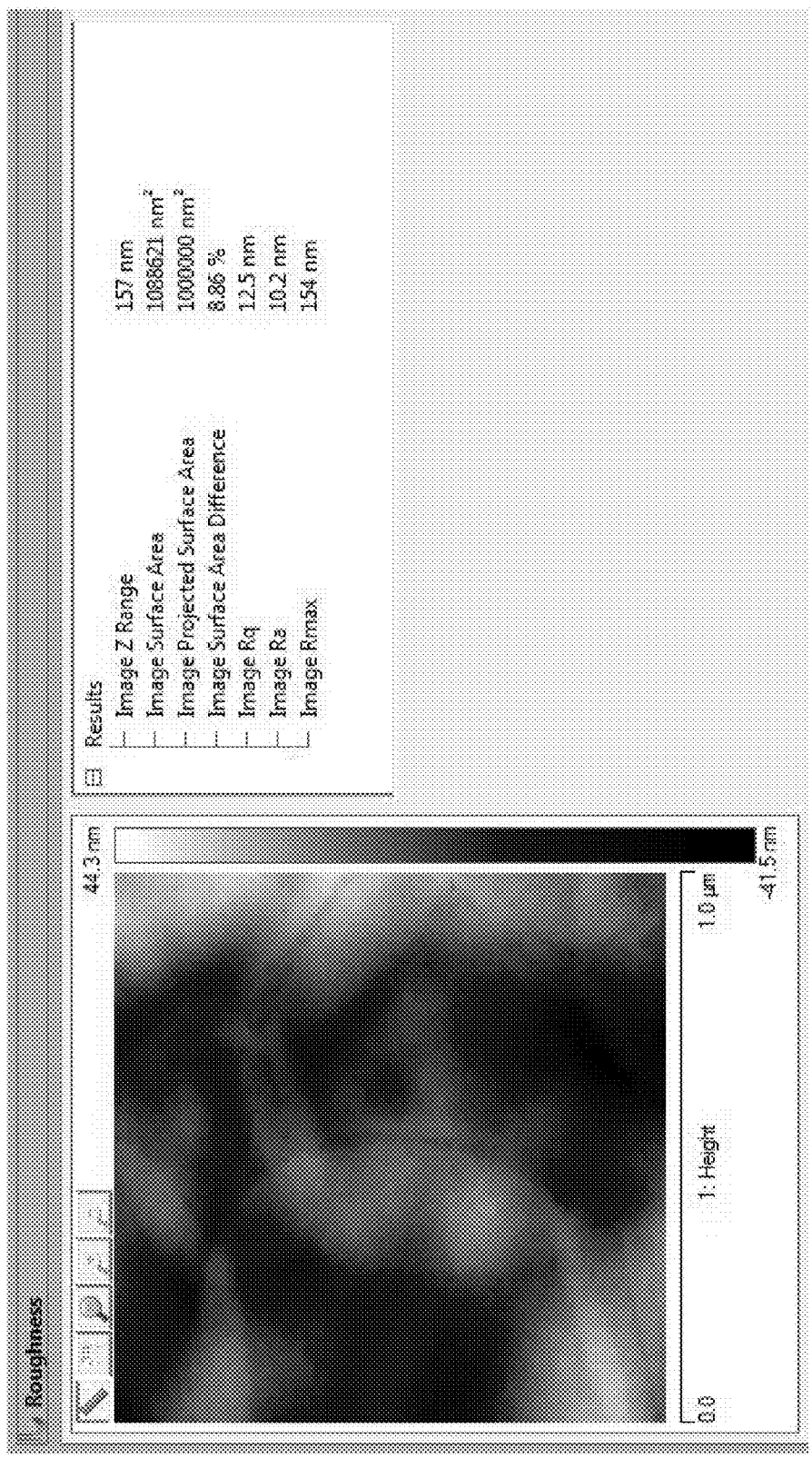

The significant structures difference from figures shown above are the SAM fabricated by added o-NPA in the mixture of mM-ß-DMCD, T-CD, PEG and PVP, that formed a flat bridge with nanopores. FIG. 2A shows the flat bridge with width 330 nm and length in 1.4 µm by cross section analysis with RMS 0.6 nm in the image. Nanopores can be seen on each side of the bridge; the pores on the left side of the bridge have a depth 0.3-0.8 nm and diameter 20-30 nm. FIG. 2B shows the membrane morphology specification in thickness 60.2 nm with the roughness 15.1 nm. FIG. 2C shows the pore size having 14-16 nm diameters on the right hand side of the flat bridge with the pore depth 0.1-2.3 nm by the cross-analysis AFM. The RMS value is 0.8 nm in a small scale view window of 500×500 nm. FIG. 2D shows the AFM specification of the surface roughness of the horizontal bridge. The body of the horizontal flat bridge was densely covered with thousands uniformly and orderly orientated donuts shaped "fish scales", density of 10$^7$ pores/cm$^2$, with the average donuts size of 22 nm in diameter and the pores in the center are 9-10 nm in diameter shown in FIG. 2D. FIG. 2E shows the AFM image of the "breathing pore" near the flat cross bridge with the pore length among 12-18 nm and the vertical pore depth is 0.1-3.0 nm and the RMS is 0.18 nm by the cross section analysis. FIG. 2F shows the membrane thickness is 44.3 nm and the membrane roughness is 12.5 nm.

Example 3—Mimicking the Active ACHE Gorge and its Linen

Figure 3A:
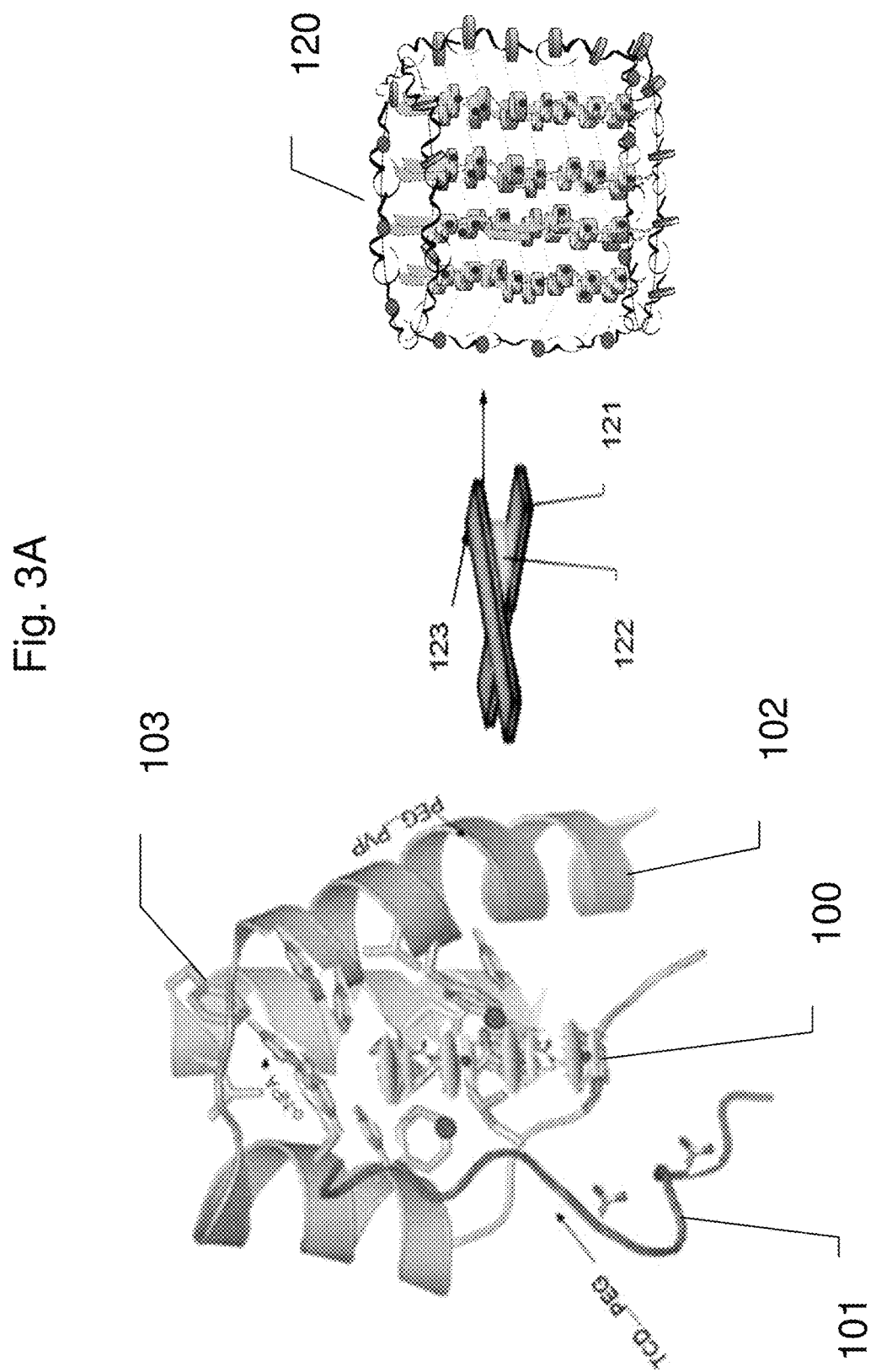
FIG. 3A depicts the art illustration of the SAM molecular polymer architecture for device 1 with an o-NPA linen in the left, "100" refers to the Biomimetic ACHE gorge with M-β-DMCD polymer chain cross-linked with PEP and has one imidazole in the carbon-3 position in each of the CD cavity as shown the red solid dot; "101" refers to the TCD . . . PEG formed polymer chains mimicking the C-terminal; "102" refers to the PVP . . . PEG polymer chains mimicking the N-terminal; "103" refers to the hydrophobic linen of o-NPA. The partial illustration of the cross bar layout from FIG. 4C's "10 to 14" was in the right. "120" refers to the toroidal structure that finally formed as detailed depiction in from "100" to "103". "121" refers to the Au electrode on a plastic substrate; "122" refers to o-NPA linen cross flat bar with TED . . . PEG//TCD . . . PVP polymer wrap; "123" refers to the nano air gap between imidazole CD polymer and the flat bridge.
Figure 3B:
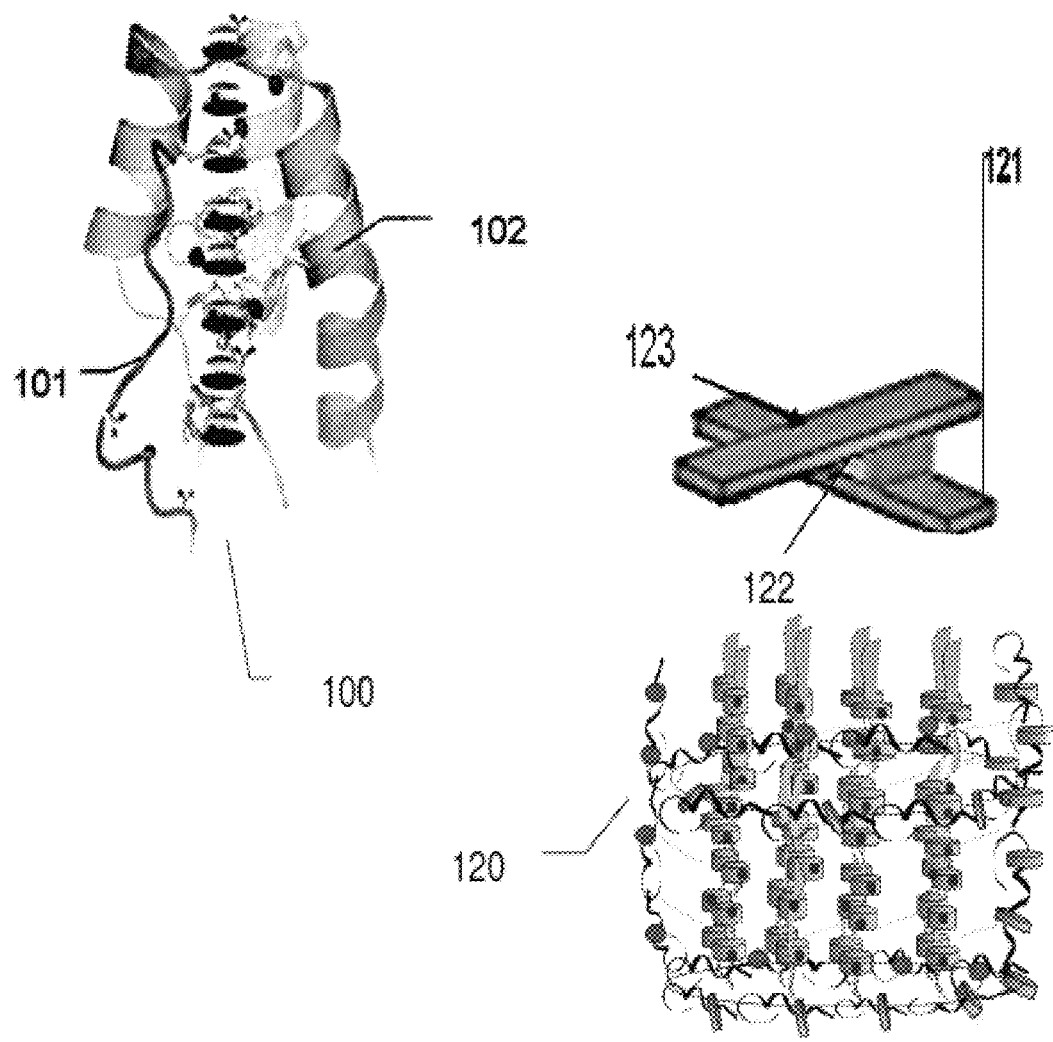
FIG. 3B depicts the art illustration of the SAM molecular polymer architecture of device 2 without an o-NPA linen in the left, and the partial illustration of the cross bar layout from FIG. 4D's "10 to 14" was in the right. "100", "101" and "102" descriptions are same as in FIG. 3A, but device 2 has no "103"—the o-NPA linen. "120" refers to a toroidal comprising of a flat bridges with the TED . . . PEG//TCD . . . PVP polymer wrapping around with the networking by hydrogen bonding; "121" description is same as FIG. 3A. "122" refers to the nano air gaps between the flat bridge and the imidazole CD polymer vertical block; "123" refers to the TED . . . PEG//TCD . . . PVP polymer flat bridge with nanopore.
Figure 4A:
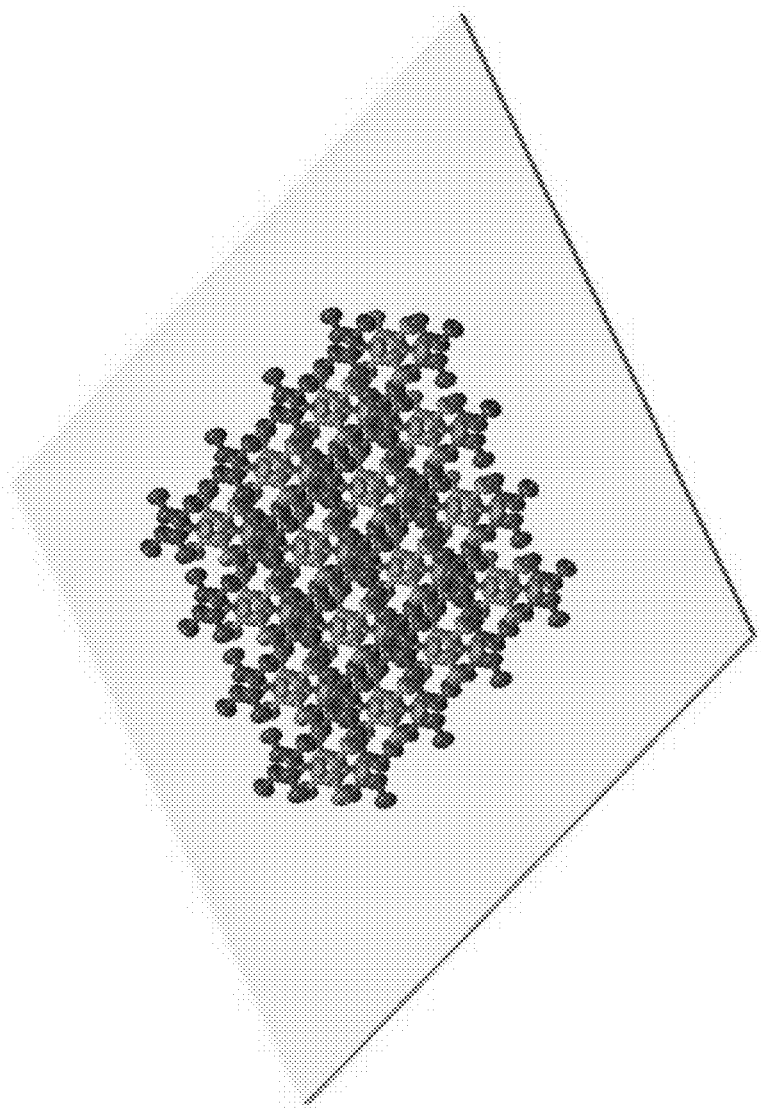
FIG. 4A depicts the art model of the memcapacitor 1 of "normal brain ACHE gorge". The light green color substrate is a 50 nm thickness pure gold plate attached onto a flexible plastic plate. The model consists of green balls and sticks in the top and bottom layer covered with conductive cross-linked polymers; The oranges represent the inner "ACHE Gorge" neuronal axons in narrow cylinders connected through the neuronal terminals and dendrites as truncated donuts in a compact flat metrics.
Figure 4B:
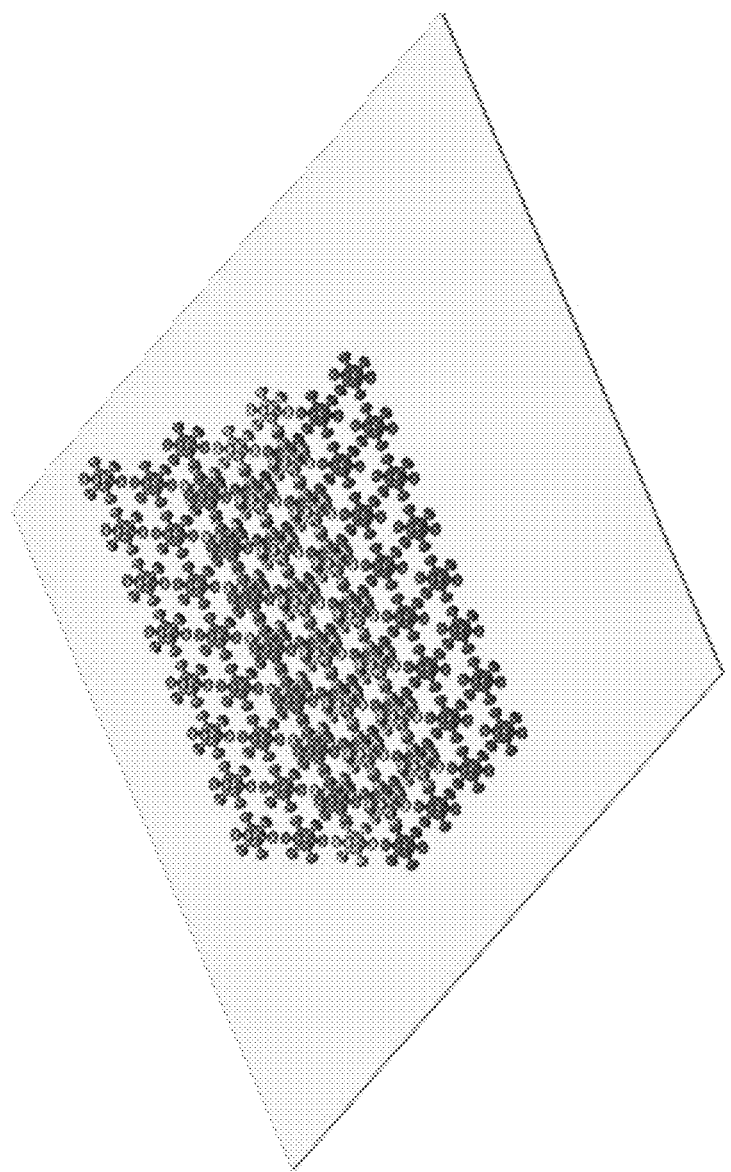
FIG. 4B depicts the art model of the working device 2, the "mutated ACHE gorge neuron" prosthesis. The dark blue, purple and browns represented the connections are partially alignment with each other, that formed a stairway type of molecular architecture that sited on a light green plate of 50 nm thickness gold onto a flexible plastic plate. The linen of the ACHE gorge was missing.

A "Normal Active Site ACHE Gorge" was defined as a linen-cylinder consists of a bipolar dome with two poles. (1): the positive isopotential pole: esteratic site of five residues containing the catalytic triad (Ser-200, Glu-327, His-440), acyl pocket Phe 288 and Phe-290 [37-40], that was mimicked by polyethylene glycol diglycidyl ether (PEG) (for Ser 200) . . . imidazolyl-dimethyl-β-cyclodextrin (M-CD) (for His 440) . . . triacetyl-β-cyclodextrin (T-CD) (for Glu327). Phe288 and 290 were mimicked by o-NPA. (2) The 14 aromatic residues for gorge lining were mimicked by excess amount of o-NPA (1:500-1000 of T-CD/o-nithophenyl acetate (o-NPA)) and W84 were mimicked by poly(4-vinylpyridine) (PVP). (3) the negative isopotential pole: the Asp-72, Tyr-121, Tyr-70, Tyr-354, and Trp-279 are the residues of the peripheral and were mimicked by TCD . . . PEG polymer and TCD . . . PVP polymers as anionic site (PAS), F330, Y121 were mimicked by o-NPA, and Trp279 was mimicked by PVP. By knock out all o-NPA out of the network, we define the second device as "Mutated Active Site ACHE Gorge" based on our hypothesis: Lacking of hydrophobic lining in the gorge might be the key issue caused diseases, because the nature of the ACHE gorge might be mem-ristive, mem-capacitive and mem-inductive in nature. FIG. 3A and FIG. 3B depict the Biomimetic ACHE gorge of a "normal brain" and a "mutated brain" gorges, respectively. In FIG. 3A, "100" refers to the biomimetic ACHE gorge with M-β-DMCD polymer chain crosslinked with PEP and has one imidazole in the carbon-3 position in each of the CD cavity as shown the red solid dot; "101" refers to the TCD . . . PEG formed polymer chains mimicking the C-terminal; "102" refers to the PVP . . . PEG polymer chains mimicking the N-terminal; "103" refers to the hydrophobic linen of o-NPA. The partial illustration of the cross bar layout from FIG. 4C's "10 to 14" was in the right. "120" refers to the toroidal structure that finally formed as detailed depiction in from "100" to "103". "121" refers to the Au electrode on a plastic substrate; "122" refers to o-NPA linen cross flat bar with TED . . . PEG//TCD . . . PVP polymer wrap; "123" refers to the nano air gap between imidazole CD polymer and the flat bridge. FIG. 3B depicts the art illustration of the SAM molecular polymer architecture of device 2 without an o-NPA linen in the left, and the partial illustration of the cross bar layout from FIG. 4D's "10 to 14" was in the right. "100", "101" and "102" descriptions are same as in FIG. 3A, but device 2 has no "103"—the o-NPA linen. "120" refers to a toroidal comprising of a flat bridges with the TED . . . PEG//TCD . . . PVP polymer wrapping around with the networking by hydrogen bonding; "121" description is same as FIG. 3A. "122" refers to the nano air gaps between the flat bridge and the imidazole CD polymer vertical block; "123" refers to the TED . . . PEG//TCD . . . PVP polymer flat bridge with nanopore.

Example 4—Engineering the Devices

The "Normal ACHE Gorge" Neuronal Network Device

Figure 4C:
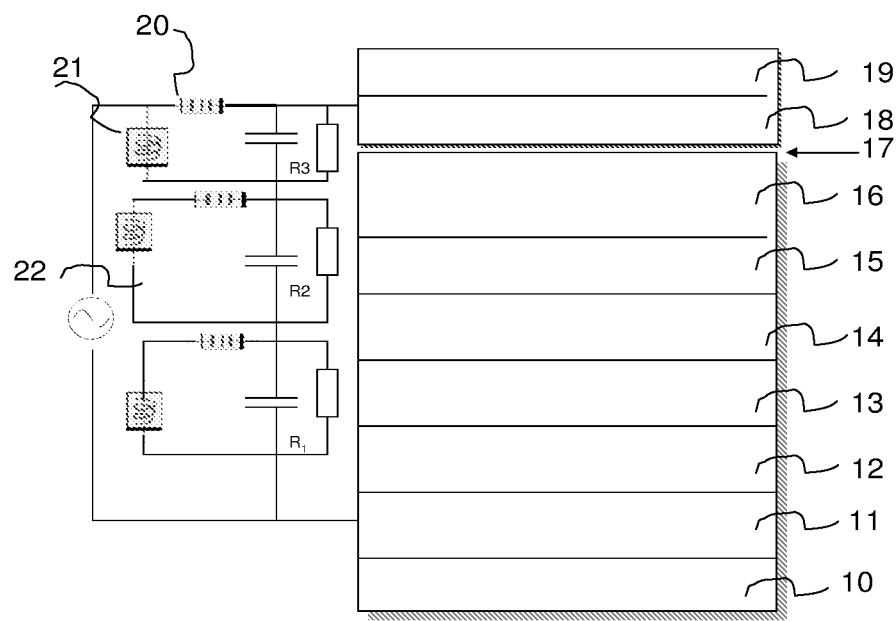
FIG. 4C depicts the schematic components of the device 1 having different layers and each one servers their own functions. "10" is the plastic plate; "11" is the Au, or Pt, or metal electrode; "12" is the imidazolyl derived mono-substitute β-dimethylcyclodextrin (m-β-DMCD, in short, MCD) cross-linked with PEG, PVP and TCD forming a self-assembled conductive organic membrane with positive and negative electron-relay circular current flow inside the cavity with opposite direction separated by nano air gap; "13" is the nano air gap between two chucked CD "donuts-like" cavity; "14" is the o-NPA formed ACHE gorge linen with other residue groups through hydrogen bonding or hydrophobic bounding wrapped around the cross bars with the TCD . . . PEG//TCD . . . PVP polymers; "15" is the nano air gap between the NPA linen and the polymer TCD . . . MCD . . . PEG . . . PVP; "16" is horizontal cross bars of NPA linen with polymer TCD . . . PEG//TCD . . . PVP; "17" is the slot for injection of biological sample; "18" is the 50 nm thickness pure gold electrode without a membrane; "19" is the plastic substrate; "20" is the memcapacitor; "21" is the meminductor; "22" is the schematic circuitry box indicating the mem-transformer function of the device 1's design based on step 10 to 19 that may produce functions equivalent to the electric circuitry box drawn on the left-hand side proposed.

The "Normal ACHE Gorge" Neuronal Network Device was built by arrays of 3D cross bars by self-assembling technology with the above section mentioned membrane in FIG. 3A. The FIG. 3A on the right-hand side is the illustration of the 3D cross bar, the vertical green bar presented here was made by the architecture of a vertical double-layer cylinder with an inner core cylinder consists of a chain of cyclodextrin chunked "donut" shape, hollow in the center, as pendants and the PEG as the necklace chain between the two relay circuits is the nanometer air gap serves as the dielectric substance; the basement bar was made of the gold; The horizontal bar was made by the o-NPA formed hydrogen bounding or hydrophobic interaction with the TCD . . . PEG//TCD . . . PVP wrapped around the flat bridge structure. This is a partial illustration of the cross bar essential block, as shown the coil wrapped in a toroid. The detailed illustrations were shown in FIG. 4A as an art model and in FIG. 4C is for a detail explanation. "10" is the plastic plate; "11" is the Au, or Pt, or metal electrode; "12" is the imidazolyl derived mono-substitute β-dimethylcyclodextrin (m-β-DMCD, in short, MCD) cross-linked with PEG, PVP and TCD forming a self-assembled conductive organic membrane with positive and negative electron-relay circular current flow inside the cavity; "13" is the nano air gap between two chucked CD "donuts-like" cavity; "14" is the o-NPA formed ACHE gorge linen with other residue groups through hydrogen bonding wrapped around the cross bars with the TCD . . . PEG//TCD . . . PVP polymers; "15" is the nano air gap between the NPA linen and the polymer TCD . . . MCD . . . PEG . . . PVP; "16" is horizontal cross bars of NPA linen with polymer TCD . . . PEG//TCD . . . PVP; "17" is the slot for injection of biological sample; "18" is the 50 nm thickness pure gold electrode without a membrane; "19" is the plastic substrate; "20" is the memcapacitor; "21" is the meminductor; "22" is the schematic circuitry box indicating the function of the device 1's design from 10 to 19.

The left-hand side of FIG. 4C depicts the electronic circuit function of the device 1's engineering architecture, that consists of 3 elements of memcapacitors, three memristors and three meminductors connected to be functioning as a "normal ACHE neuronal circuitry" to have an alternative voltage output and changed resistance and capacitance. The air gap between the CD cavity is much smaller than the air gap between the flat NPA mash bridge and the rim of the CD cavity. The variations air gaps at different sections in the flow chart reflect the essence of the flexibility, neuronal plasticity possible.

The "Mutated ACHE Gorge" Neuronal Network Device

The "Mutated ACHE Gorge" neuronal network device was built by arrays of 3D cross bars by self-assembling technology with the above section mentioned membrane in FIG. 3B. The FIG. 3B on the right-hand side is the illustration of the 3D cross bar, the vertical green bar proposed here was made by the architecture of a vertical double-layer cylinder with an inner core cylinder consists of a chain of cyclodextrin chunked "donuts" shape, hollow in the center, as pendants and the PEG as the necklace chain between the two relay circuits is the nanometer air gap serves as the dielectric substance, such as for Device 1 in FIG. 2A-2G, the 3D lattice between the flat bridge and the top rim of the surface of the pores has gaps of 40-56 nm; yet the Device 2 has gaps between 6-121 nm in FIG. 1A-1G. Device 2 can become a hybridized memristor with bridges having 115 nm apart in height, and the Device 2 has uniform distance between the bridge and the top rim of the nanopore. Hence related to Device 1, Device 2 has less characteristics of electric synapse than Sensor 1, especially at the SWS, the circuitry may be damaged due to the missing a key NPA linen that leads to a "born with" electric flow disadvantage due to the air gap was too large; the basement bar was made of the gold; The horizontal bar was made by the TCD . . . PEG//TCD . . . PVP wrap around the horizontal bars made by W84 from PVP through hydrogen bounding, that is too loose to form a well balanced one electronic unit of memristor-memcapacitor-meminductor. This is a partial illustration of the cross bar essential block, as shown the coil wrapped in a toroid. The detailed illustrations were shown in FIG. 4B as an art model with stair type architecture and in FIG. 4D depicts the schematic components of the device 2 having different layers and each one serves their own functions. "10" is the plastic plate; "11" is the Au, or Pt, or metal electrode; "12" is the imidazolyl derived mono-substitute β-dimethylcyclodextrin (m-β-DMCD, in short, MCD) cross-linked with PEG, PVP and TCD forming self-assembled conductive organic membrane with positive electron-relay circular current flow; "13" is the nano air gap between two chucked CD "donuts-like" cavity; "14" is the cross-bar consists of polymers residue groups having negative electron-relay circular current of MCD . . . PEG . . . PVP wrapping around with ribbon of TCD . . . PEG//TCD . . . PVP; “15” is nano air gap between 14 and 15 cross-bars; “16” is cross bar of MCD . . . TCD . . . PEG . . . PVP cross-linked polymer; “17” is the slot for injection of biological sample; “18” is the 50 nm thickness pure gold electrode without membrane; “19” is the plastic substrate.

Example 5—The Device Circuitry

The device 1 or device 2 circuitry consists of a memcapacitor, a memristor and a meminductor connected in series as shown in the left-hand side of the circuitry in FIG. 4C. This is a well known Tank Circuit, that the resonate circuit provides voltage amplification and a reversed sign. [http://en.wikipedia.org/wiki/LC_circuit]. The three in one system was proposed and explained in literature [41]. The detail example of the device 1 as a mems-transformer model's electromagnetic fields was depicted in FIG. 5. FIG. 5 depicts the model of the electromagnetic field of the mems-transformer and the eddy current for device 1. The blue line of the magnetic B field outside of the core cylinder is zero, only the induced circular eddy current as yellow color produced a magnetic B field inside of the core cylinder as seen to perpendicular to the blue magnetic line was the purple line. This down-bell double toroidal structure is a key function for human memory and intelligent communication consciously in wave forms; hence the ACHE gorge is the primary neuron groups provide an advanced function for human that was distinguished from other creatures.

Memristors are devices made of nanolayers that have the capability to mimic neuronal synapse with a characteristic of hysteresis loop in the i-V curve [41-46]. A memristor is a semiconductor whose resistance varies as a function of flux and charge. This allows it to “remember” what has passed through the circuit [28, 41-43]. In the equation 1, where I(t) is the current passing through the memristor, and V(t) is the potential across it, and G({x},t) which is the non-leaner conductance with state dependent. {x} is the state variable.

$$I(t)=G(\{x\},V,t)V(t) \quad (1)$$

Device 1's hysteresis i-V profiles measured by the cyclic voltammetry (CV) method are presented in FIG. 6 in NIST serum without Aβ. Data Acquisitions were conducted by connecting the memristor chips with an electrochemical station (Epsilon, BASi, IN) with the BASi software package in the computer. The gold chip consists of three gold leads, the center circle gold chip with the Biomimetic membrane is connected to the anode, and the pure gold electrode without a membrane is connected to the cathode electrode, and the gold electrode is connected to the reference electrode at a fixed scan rate under an applied electrochemical potential, the current was recorded due to the change of a direct electron-relay (DET) either in oxidation or reduction direction. DET phenomenon is a key event in sensing and energy storage that led to our several inventions [47-51]. FIG. 6 has scan rate changed from 1-300 Hz over the potential range of −800 mV to 800 mV as shown in FIG. 6 in the NIST reference SRM 965A human serum without Aβ. The characteristics of hysteresis are the loop with a pinch (as called for a cross-point) switched at zero applied potential and zero current as shown in FIG. 6-8. The intensity of the DET peak was reduced by a hundred times, and the cross-point locations were moved nonlinearly toward to negative field as frequency increased in the presence of 3.8 nM and 76 nM Aβ as shown in FIGS. 7 and 8, respectively compared to without Aβ. Various concentrations of Aβ reduced the DET peak intensity by 94-99% in SWS frequency more than any other frequencies. Device 1 showed significant bipolar nonlinear hysteresis through the CV curves at low frequency, and linear hysteresis at high frequency.

Device 2's memristor characteristics was shown in FIGS. 9 and 10 in NIST human serum without Aβ and with 38 μM Aβ, respectively over the scan frequencies 1-10 KHz. Device 2 was unable to sense at nM level. Under the influence of Aβ, it exponentially increased the DET reduction peak intensity, and the peak moved toward negative potential drastically as frequency increased thus indicating a significant circular current exists driven by the toroid forces due to the broken ACHE gorge linen [52]; multiple cross-points occurred over the whole frequency range. Again, the CV curves approved the device 2 has a bipolar double toroidal domes cylinder structure with an unusual electromagnetic disturbance inside of the gorge.

Example—7 Characteristics of Mems-Capacitors

The Synapse Energy Profiles Impacted by the Presence of Aβ

A total charge of a memcapacitor is a function of a state dependent of capacitance and the potential across it, where q(t) is the total charge on the capacitor, and V (t) is the potential across it. A capacitance C({x}, t) which is state dependent [28].

$$q(t)=C(\{x\},V,t)V(t) \quad (1)$$

The synapse energy profiles data Acquisitions were conducted by connecting the memcapacitor chips, the gold lead with nano-biomimetic membrane was connected to the anode, the bare gold lead was connected to the cathode, so was the reference connected to the pure gold lead, then the cable was connected with an electrochemical station (Epsilon, BASi, IN) with the BASi software package in the computer. The double step chronopotentiometry (DSCPO) method was used to measure the voltage change upon applied an alternative small current under ±10 nA with data rate 0.001 s at 0.25 Hz and $2\times10^{-5}$ s data rate over the frequency range of 40 Hz−1 kHz were chosen under the room temperature. The time for action potential and resting potential (discharge vs. charge steps) have to be settled in a desired time frame. The real time data was acquainted under this program. In this invention, the Origin 9.0 software was used for data analysis and plotting figures.

Device 1: Aβ concentrations of 3.8 nM and 76 nM had exponentially significantly reduced signal intensity at lower frequencies over 0.25-1 (SWS) Hz compared at higher frequencies from 10-1000 Hz in device 1, as shown in the DSCPO original data in FIG. 11$A_1$, FIG. 11$A_2$ and FIG. 11$A_3$ for spiked Aβ=0, 3.8 nM and 76 nM, respectively. FIG. 11B depicted the volumetric energy density plot vs. frequencies 0.25 Hz to 333 Hz for comparison of with or without Aβ. The key characteristic of a memcapacitor is the nonlinearity impact of charge on frequencies; we have demonstrated using CV and DSCPO method that at lower frequency has higher impact of charge to the peak intensity (either current, or voltage) than at higher frequencies nonlinearly. Overall, Device 1 is very sensitive to the presence of Aβ than device 2.

Figure 9:
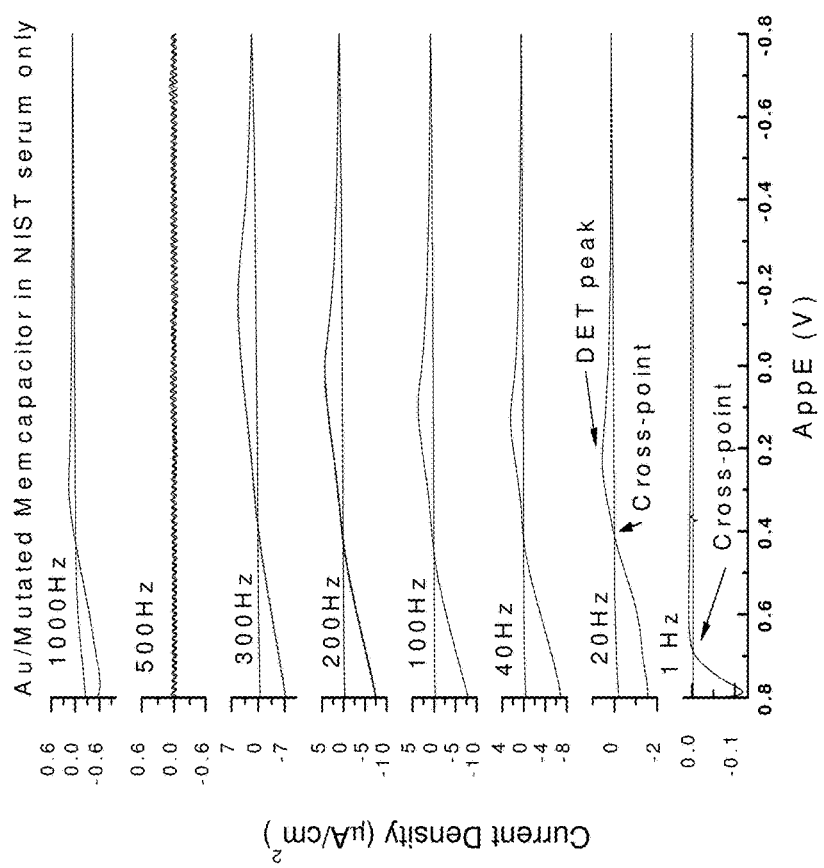
FIG. 9 depicts CV profiles of device 2 without spiking Aβ over scan frequencies 1 to 1 kHz in NIST human serum.

Device 2: It has very small energy discharge magnitude compared with device 1 using the voltage sensing method, regardless of whether device 2 is with or without Aβ over 0.25, 40 to 250 Hz, as shown in FIG. 12A, FIG. 12B and FIG. 12C, respectively. Device 1 has a several magnitude higher intensity at SWS than device 2. Device 2 is in short of the characteristics as a memcapacitor in respect to the capacitance nonlinearity impacts on the voltage as frequency increase using the DSCPO method as seen in FIG. 12A, FIG. 12B and FIG. 12C. However, FIG. 13 demonstrated the perfect memcapacitor behavior of charge of the DET peak at an applied voltage vs. frequency for device 2 over 1-500 Hz, which is nonlinear when frequency increased to >200 Hz, the charge values were dropped abruptly based on the data obtained from FIGS. 9 and 10 using the CV method.

Another example of the specific characters is the charge vs. voltage at 100 Hz using a CV method for Device 1 compared with Device 2 in pure NIST serum without Aβ in FIG. 14. Device 1 demonstrated a typical memcapacitor's behavior that the charge density is a function of the product between voltage and capacitance, and also dependents on the state of the capacitance, because the capacitance is various in positive and negative. Device 1's switch is at zero potential, but Device 2's pinch point moved far away from it. At −0.7V, Device 1 has the highest negative capacitance of 10 μF/cm$^2$ compared with Device 2 with a positive capacitance of 2.7×10$^{-3}$ μF/cm$^2$, it means Device 1 has a great potential to be spontaneously discharge an electron than accept an electron. In contrast, Device 2 has a hard time to fire a synapse. Even at +0.1V, Device 2 has its highest capacitance of +0.37 μF/cm$^2$ compared Device 1 still has a negative capacitance of −0.37 μF/cm$^2$.

Example—8 The Nanostructure Mems-Transformer Characteristics of Mems-Inductor

The memory of the inductance can depend on both the magnetization history as well as on the geometrical changes of the inductor [28].

$$\Phi(t)=L(\{x\},I,t)I(t) \quad (1)$$

where Φ(t) is the flux-linkage (integral of the voltage), I(t) the current, and the inductance L depends also on some state variables with their own equations of motion[28].

The discharge potential curve at 0.25 Hz (4 s) is about 14.7V/cm$^3$ according to FIG. 11A panel A and it reversed the sign to a resting potential of −15V/cm$^3$, that was amplified by 150-fold at each end compared with the initial applied potential for active of the device, it was −0.1V as shown the initial activation curve b in FIG. 16 panel B. This event has confirmed that the device has the equivalent function of the resonate tank circuit, that is a voltage amplifier.

Figure 5:
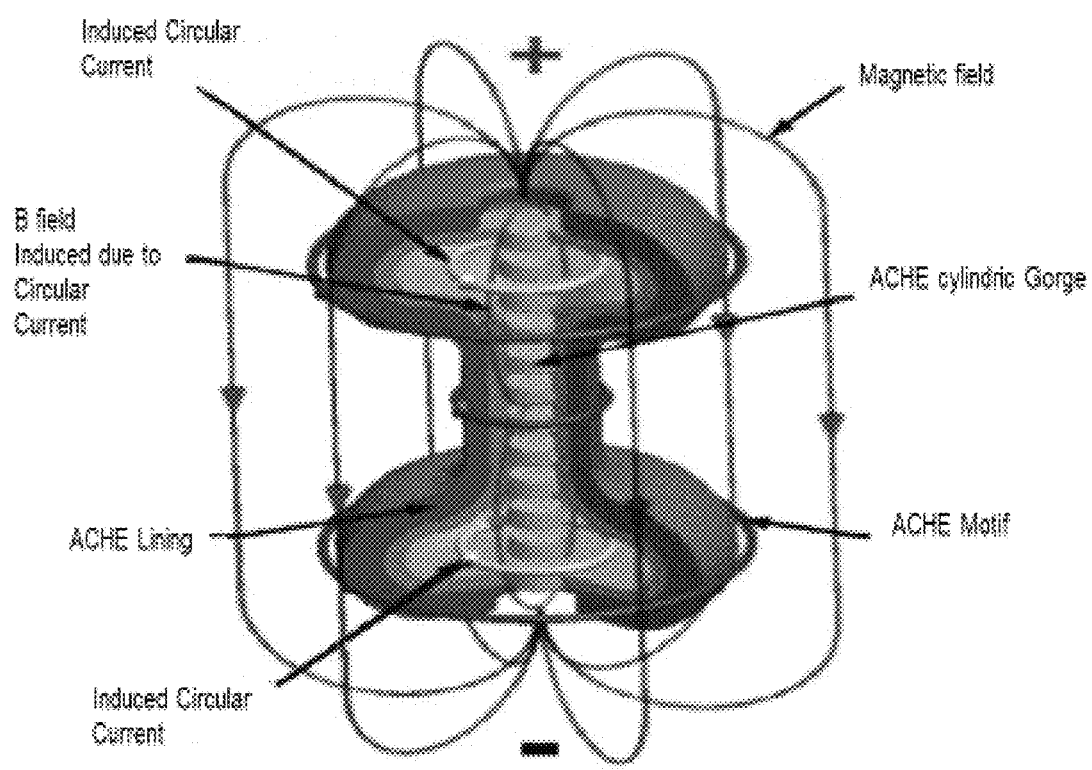
FIG. 5 depicts the model of the electromagnetic field of the mems-transformer and the eddy current for device 1.
Figure 6:
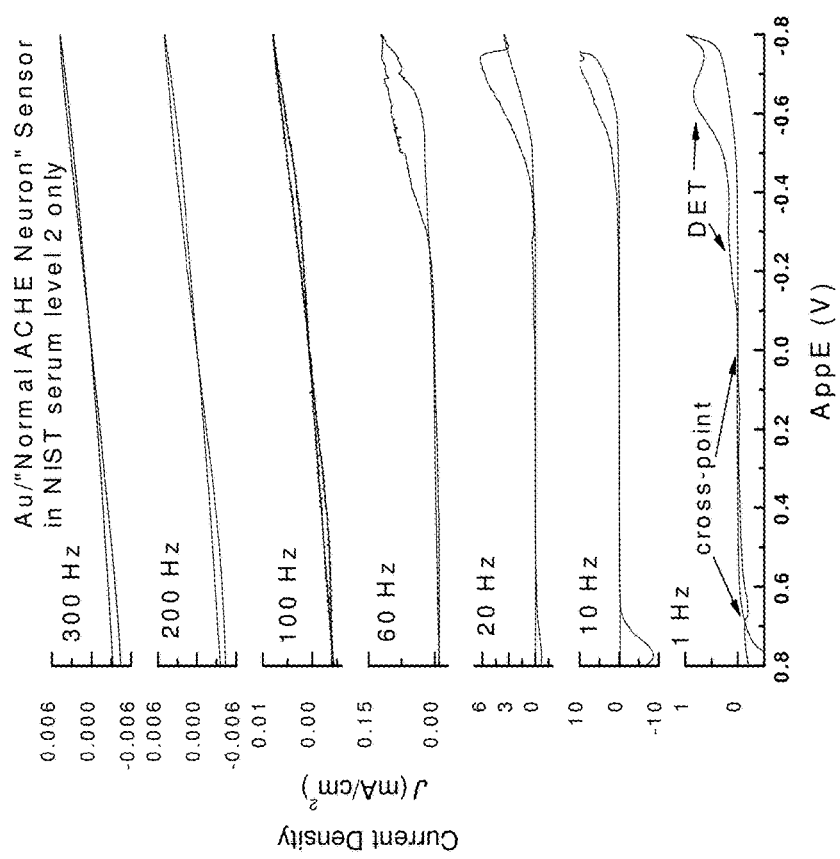
FIG. 6 depicts device 1's CV profiles without spiking Aβ in NIST serum over frequency 1-300 Hz. The DETs peak and the cross-point locations are labeled in arrows.
Figure 7:
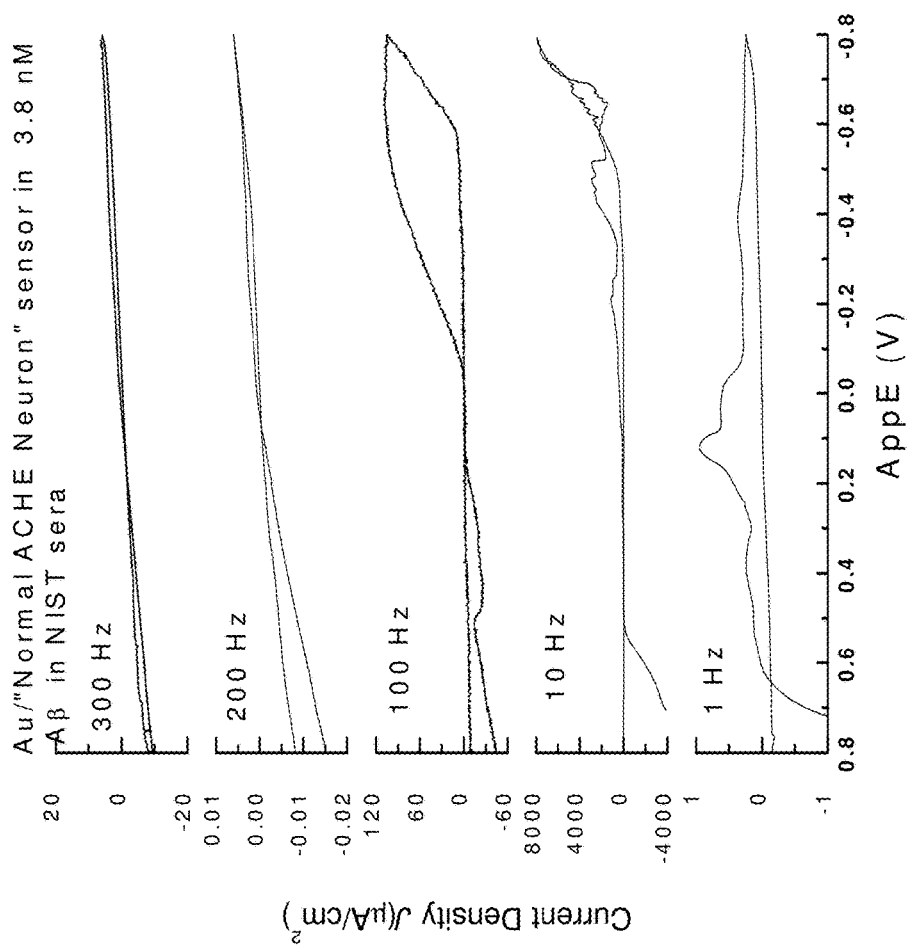
FIG. 7 depicts CV profiles of device 1 in 3.8 nM Aβ in same serum as in FIG. 6.
Figure 8:
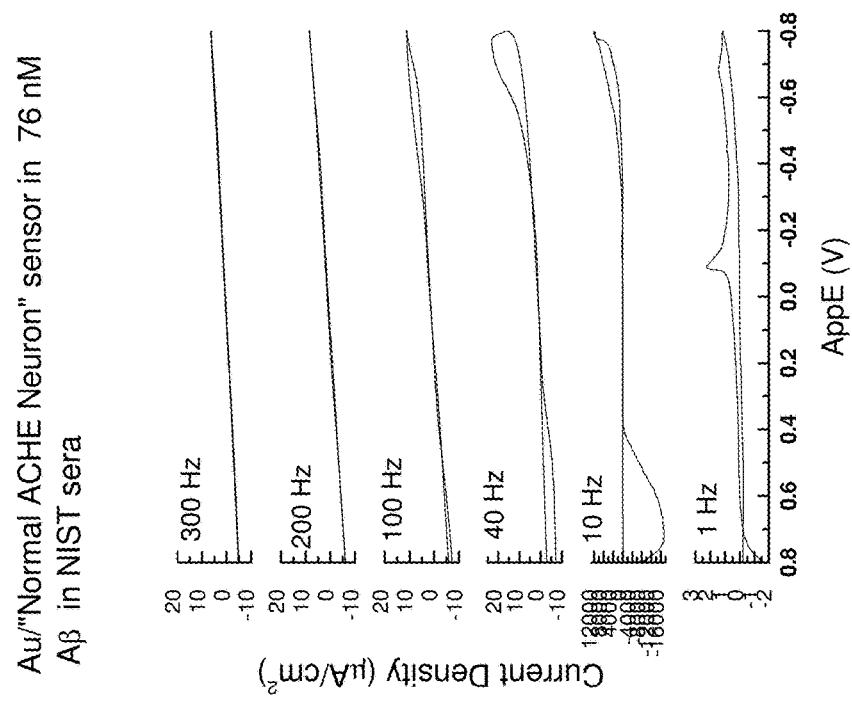
FIG. 8 illustrates CV profiles of device 1 with 76 nM Aβ in same serum as in FIG. 6.

It also is an alternative current amplifier under a DC potential of −0.2V in fresh human capillary whole blood specimens with triplicates using a chronoamperometric (CA) method was shown in FIG. 15. The AC out put current curves indicate a longitudinal cylinder tunneling effect exist that was caused by the bipolar double toroidal nano-channeling ACHE gorge formation of the membrane against an initial activation/equilibrium at −0.1V DC potential with an s-s current 1.3 nA, which the biomimetic ACHE cylinder has amplified the current by 46-fold without adding any circuitry, that offers a significant advantage of reducing the system size and avoiding lose energy compared to the pure electronic circuitry assembling method. Because the present invention is solely based on the unity of bipolar memristor/memcapacitor/meminductor membrane formed the innovative transformer in double toroid vertex architecture shown in FIG. 5B, hence there was no heat produced because of the field dominating rather than thermal dominating, based on the teaching from the literature [53].

An electromagnetic transformer is an electrical device that transforms voltage levels between two circuits. A transformer operation is based on the principle of electric induction. When a changing magnetic flux links to a circuit and a voltage is induced or electromotive force (emf) is induced in the circuit. The induced voltage is proportional to the number of turns linked to the changing flux [65-66]. The present invention utilized the principles of induction through a self-assembled cross-linked membrane as shown the models in FIGS. 3A and 3B along with the AFM images from FIG. 1 to FIG. 2 that facilitates a center core-form of solenoid that consists of a chain of "donut"-shaped cyclodextrin cavities described in example 3 [00064], and the green color polymer chains shown in FIGS. 3A and 3B facilitate the out layer toroid covering the center solenoid, and stabled by the horizontal hydrogen bonding and hydrophobic bounding. When a potential is applied to the system, there is an inductive effect happened in the center core, so promoted an amplification of the outlet voltage as shown in FIG. 16 panel A curve A increased the volumetric voltage density by 130-fold compared with the initial applied potential of −100 mV. By fitting a linear regression model of the normalized volumetric voltage density divided by the mean data, we obtained the equation to solve the initial rate within the first 10 ms is y=0.2+148x, r=0.998, Sy/x=0.03, p<0.0001; while the control for the initial rate of increased current after normalization of the current divided by the mean current produced an equation of y=−2+7.7x, r=0.99, Sy/x=0.09, p<0.09 within the first 150 ms in curve C. The result indicates the mem-transformer has about 20-fold faster initial rate to raise the voltage than do to the current that is an evidence of the eternal toroid mem-inductivity gain.

FIG. 16 panel B depicts the curve A has 54-fold increased the voltage intensity as well as the raising speed compared with the control curve C, that has a very slow rate of current increase, the phenomena explained a net inductance gain through the inner core toroid; The toroid fall time of the voltage is slower than that of the control curve C compared with curve A when switched, and the curve C in current drop, indicates an inductance gain. The inductance gain phenomena also show in FIG. 15 panel A and B, the sine waved base line curves were dropping slowly than that of the control as Aβ concentration increases, that indicates an inductance gain. In FIG. 15 panel B the curve "a" has a signal AC current intensity increased by 14-fold using human capillary whole blood specimen without spiking Aβ compared with the control shown in FIG. 15 panel A. Wherein, the transformer is also a DC to AC converter converting DC current to an AC wave shown in FIG. 15 in aqueous and in human whole blood medias.

Example 9—Evidence of the Nanometer Air Gap Existence in the Mems-Transformer

FIG. 16 panel C depicts a 0.5 cm$^2$ GC membrane electrode assembling (MEA) comprising of a self-assembled membrane of TCD/PEG/PVP/β-cyclodextrin (CD) co-polymer with an insulator and a Pt current collector at each end in solid dry state under nitrogen as curve "A", compared with the same solid dry device in an open air situation as the insert curve "C", Curve "C" has the typical behavior as a meminductor (includes the origin in the hysteresis loop)

with an order of magnitude higher current raise slope in a perfect diagonal related to origin than that of curve "A" and it also has a 1.5-fold higher current intensity than curve A. That indicates air gap is a crucial element in the toroidal type transformer to make functions more effectively and flexible. The curve "B" has shown the typical hysteresis loop at the cross-pint of origin with a current intensity of 10-fold higher than that of curve "A", and 7-fold higher than curve "C" in 1 M methanol in the presence of 0.02 M o-NPA under nitrogen, that indicates o-NPA is the most important element in the toroid to make the function properly to lining the ACHE gorge cylindered cavity. The rates to switch current directions over the scanned potential range from the lowest potential to the highest potential for the three curves in decrease order are: Curve C>Curve B>Curve A with the values of 2.7 mA/s>2.5 mA/s>0.14 mA/s under the same scan rate of 20 mV/s. In another words, the values of 135 mA/V>125 mA/V>6.8 mA/V scanned voltage to switch the current is curve C the most efficient one as a transformer having the nanometer air gap in the toroid. Curve B also confirmed the FIG. 16 panel D depicts an energy cell consists of a 0.5 cm² GC/MCD/PEG/PVP MEA and a 0.5 cm² GC/TCD/PEG/PVP/CD/O-NPA MEA separated with an insulator connected with Pt wires at each end in 1M methanol without nitrogen as curve "A" compared with the control of a pure gold in solid stage without an insulator in dryness as curve "B". Curve A has very normal transformer characteristics as cited in literature [65]. Herein, the devices made either with GC or gold with membranes described in FIG. 16 panels A, B C and D work well either air-free or with air; However for a toroid with a membrane of MCD/PEG/PVP/TCD without a laminate agent o-NPA, it needs nano air gap to avoid destruction.

Example 9—the "Sensory Biomarkers"

From the CV profiles, we constructed a Hippocampal-neocortical (HPC-NECOR) biomimetic neural sensory prosthesis as a control. The "Sensory Biomarkers" components were defined: locations of Direct Electron Transfer (DET) peaks in mV, the Hysteresis switch point location in mV. In lieu of all human sensory organs produced smile, vision, touch, taste and sound, are all transformed from an outside stimuli to chemical and electric synapses and it went to the CNS for processing information and give a feedback to the organs. Above section has demonstrated the invention is a closely mimicking the ACHE gorge's radio wave producing bipolar double toroid vertex, hence it is necessary to define such a sensory using the key characteristics of the mem-elements, the pinch field location and the DET peak location in the field. The circular current forma by the DET peak at the bipolar poles were the important electrochemical biomarkers. We are especially interested in the orientations of the biomarkers at SWS, because dysfunction spatiotemporal orientations are associated with diseases.

Example 10—Making of Energy-Sensory Images

Using the CV method to build a data matrix for a sensory prosthesis: the locations of the values of the DET peaks in mV were set up in Y-axis, the Hysteresis switch point location values were in mV set up in X-axis and Frequency associated with the biomarkers were entered in Hz (Z-axis). The real-time data obtained from the voltage sensing DSCPO method was converted to volumetric energy density, $E=C_s \cdot (\Delta V)^2/(2 \times 3600)$, $C_s$: specific volumetric capacitance $C_s=[-i \cdot \Delta t/\Delta V]/L$, $C_s$ is in F/cm³ [54-55], the $\Delta t$ is time change in second, $\Delta V$ is voltage change in V, i is current in Amps, and L is volume in cm³. The energy density data were infused into the sensory matrix sheet before Aβ and compared with that of after Aβ was spiked, and each matrix sheet has a fixed Aβ concentration. The frequencies are covered from the lowest to highest. The lowest frequency reflects a darker color and the high frequency is in a bright color. Following is the flow chart for building the 3D synapse map and the optical images of the energy-sensory interaction. It is a tool for identify early asymptomatic diseases by find the pHFOs in an electric synapse level.

Example 11—Assessing CR Dysfunction, Memory Status and Predicting of "Epilepsy" and "AD"

Evaluation of the CR dysfunction, memory status and predicting of "epilepsy" and "AD" is in two-fold: First is the energy-sensory mapping through the HFO or the pHFO. Forming HFO indicates good memory because of promoting right circuitry flow and network circuitry conformation, and forming pHFO indicates loss of memory because of the mischief circuitry flow direction and conformation, especially through the CR abnormality in the SWS; second is to calculate the sensitivity of the energy density per second using the linear regression model at a fixed Aβ concentration against that without Aβ. Prediction of "epilepsy" or "AD" was accessed by identifying the presence of the pHFO center through the energy-sensory map.

Recently, our ACH sensors have demonstrated the capability for detection of Aβ [56]. Reports show the ACHE has been overly expressed in cancer and AD, and pharmaceutical companies developed drugs to inhibit the ACHE expressions in order to increase the level of ACH [57-58]. Therefore, the purpose of the research is to test the hypothesis that ACH may restore the broken hippocampus-neocortical neuronal circuitry by using a biomimetic ACHE gorge memcapacitor/memristor device in vitro during SWS. Our next goal is to verify the relationship between a normal HFO in hippocampus-neocortical neuronal circuitry and the pHFO after the ACH added into the Aβ-spiked human serum communicates with our neuronal network device. The scope of this section is to focus on the ACH applications on the memristor/memcapacitor/meminductor device before and after presence of Aβ and to verify the hypothesis that applying ACH at SWS will be able to repair Aβ's damage on the Biomimetic neuron prosthesis, and implies the direction to go for the potential patients who suffer the neuronal damages.

The Energy-Sensory Image output comprises five steps: (1) identify the "Sensory Biomarker" (2) at the biomarker potential locations enter a discharge pulse energy data into the DET peak potential location in the "y" data column, and enter data at its spatial location of the cross-point in the "x" column, then enter a scan frequency data in the "z" column; (3) convert the xyz columns to a random correlative gridding matrix; (4) highlight the matrix and convert the matrix (5) plot the 3D energy-sensory interactive dynamic synapse map; contour map and the optical image, respectively.

Example 11A—Circadian Rhythm Profiles

The CR profiles are presented in FIG. 17. Without spiking Aβ, Device 1's original signal intensity at SWS is a hundred times stronger than the "mutated ACHE" neural device 2's signal over three replications. That indicates device 2, with a broken internal ACHE lining HPC-NECOR neuron network, has a pool memory during SWS and a dysfunctional CR. The damaged ACHE cylinder gorge device has very low net voltage discharge magnitude in SWS compared at other frequencies indicating the CR dysfunction regardless with or without Aβ over 0.25, 40 to 250 Hz shown in FIG. 17. Our former work revealed that a "normal ACHE gorge" memcapacitor device has several magnitude higher voltage intensities at SWS than this device [59] and that indicates there is a lack of memory consolidation. FIG. 17 shows the device 2 is not sensitive to energy change in the presence of Aβ. Aβ drags the energy toward a more negative field. In the middle panel of FIG. 17, the phase lag and change frequency occurred from 40 Hz to 160 Hz indicating the neural network synapse is abnormal.

Example 12—Assessing the ACH's Repairing Function

Evaluations of ACH's repairing of neuronal network circuitry damage is in two-fold: first is to analyze the energy-sensory map and see the pHFO situation before and after ACH applied; second is to calculate the sensitivity of the energy density per second change using the linear regression model at a 38 μM Aβ concentration against that without Aβ over 0.25-250 Hz using DSCPO method. ACH repairs dysfunctional CR at SWS was demonstrated in FIG. 18 using Device 2, regardless of whether conditions are with or without Aβ with the DSCPO method. With ACH, the device 2 discharges highest voltage at SWS compared to that at 40 and 250 Hz. All curves were averaged for three replicates. Electric synapse strength enhanced by orders of magnitude, it means the memory of the damaged neuronal prosthesis was restored, and it also implies to the potential patient that uses the 15 nM ACH at SWS is a right path to repair memory damage. However, it is only a suggestion, because the appropriate dosage has not established yet. The inversed trend was reflected in FIG. 19 from the CV profiles as expected, however, after applied the ACH, the Aβ signal was eliminated.

Example 13—Using Energy-Sensory Technology to Predict and Monitor the Early Signs of Neuronal Diseases The goals of using Energy-Sensory image map technology are to predict and monitor early signs of neuronal related diseases, here we use AD, epilepsy and dysfunction CR as examples. Device 1's energy-sensory images without Aβ are presented in FIGS. 20 and 21. For the initial "neural network prosthesis" before discharging a pulse, the circuitry synapse networking flow is an "8" shape on a flat 45° surface without forming HFO in FIG. 20 panel A. The contour map is in panel B and the optical image in panel C has strong light intensity indicating the healthiness of the left or right-side of semi sphere in neocortex-hyppocampus in contact with the human serum. After the neural network discharged pulses, the HFO was formed and labeled in FIG. 21 with locations at the "Sensory Origin" (SO) (cross-point 0.0 mV, DET 0.0 mV) over 60-140 Hz. The bright star-like image in FIG. 21 panel C optical image was reflected at the exact spatiotemporal location in FIG. 21 panel A and B and indicates the HFO is a good reentrant center; not only does it have the same circuitry flow direction, it also enhances the brain energy and memory. It was initiated by a yellow circle located at the bottom floor overlapping the SO, shown in FIG. 21 panel A, from neocortical to hippocampus through entorhinal cortex (EC)-subiculum-CA1-CA3-DG flowing on a 45° flat surface. It has an agreement with the observation made from FIG. 17 that the normal neuron device 1 has a better CR function than device 2 in voltage discharge intensity at SWS using the DSCPO method. In contrast, Aβ in the biomimetic neural network environment, acted not only as a biomaterial, but also as an agent to kill the good HFO by altering the network circuitry confirmation from a flat orientation to a vertical stereo structure; changing the circuitry direction by close to DET's 0 mV; and re depositing Aβ in multiple areas at neocortex through mutated-reentrant with bended surfaces as worsened in the order of FIG. 21<FIG. 22<FIG. 23 with a heavy damage in SWS discharge pulses. Hence device I demonstrated its function to monitor the early CR dysfunction by using the energy-sensory image technology. As the concentration increases from 3.8 to 76 nM Aβ, the light intensity in the images were greatly darkened from 60% at 3.8 nM to 96% at 76 nM. It indicates a brain volume loss by the correspondence percentage of light intensity diminish. To a "normal ACHE gorge neuron network" device 1, at 76 nM level, the brain faces "life-threatening" danger and yet without any symptom of epilepsy, because of lack of the pHFO induction center. However, the "death" was caused by the neuron shrinkage from both of the neocortex and the hippocampus neurons loss evidenced by our images in FIG. 23. The event has matched with the clinical fMRI evidences [60-61]. Schuff's group reported a multiple-center clinical study for AD, it discovered the hippocampus volume loss is proportional to the severity of AD progress [60]. Vijayakumar's study revealed AD patients' hippocampus volumes reduced by 25% compared with the control group and led to a same conclusion as drawn from Schuff [61]. Detailed explanations of the neuronal loss for AD see reference 62.

"Mutated Neural Network" Device 2. Four stages of AD or epilepsy are presented in 6 groups of figures from FIG. 24 to 29. Each group consists of three panels of figures as similar as above section. The epilepsies are a spectrum of brain disorders impacted by or presented in a wide range of diseases, such as diabetes, cancer, traumatic brain injury, brain tube deficiency, Alzheimer's, asthma, heart failure, Parkinson's and depression. The degrees of severity vary. There is an urgent unmet need to predict epilepsy in order to develop devices that are able to reliably predict and monitor seizures and help avoid life-threading episode. Our "mutated ACHE gorge" neural device is able to provide first-hand information regarding the prognosis of epilepsy in different stages when the neural toxin Aβ in high concentration interacts with the damaged prosthesis in an electric field. The sensory brain prosthesis was built by the biomarker CV data with only one cross-point and one $DET_{red}$ peak locations at each of the frequencies from 1 to 300 Hz without Aβ; there was no brain synapse pulse discharged. Three categories of maps are presented in 3D Energy-Sensory map before energy infusion without Aβ, as shown in FIG. 24 panel A, there was no pHFO to be observed. Panel B in FIG. 24 is the contour map, the panel C shows the original "damaged neuron" device 2's light image, and the light intensity was a 1-2% of the "normal ACHE neuron" device 1 at the same situation compared in FIG. 20 in the panel C. FIG. 24 presents the AD or Epilepsy in "Stage Zero". The epilepsy or AD "stage 1" sensory prosthesis was built by the biomarkers CV data with only one cross-point and one $DET_{red}$ peak locations at each of the frequencies from 1 to 300 Hz without Aβ; the brain pulse discharges energy values at 0.25, 40 and 250 Hz were infused in the matrix without Aβ was defined as "Stage One" for epilepsy and AD. It was presented in FIG. 25. The pHFO center can be seen in all three panel figures after discharged pulses and without Aβ. The network circuitry surface has more curvature than FIG. 24 panel A, and the direction of the circuitry flows against that of the original network current flow and was initiated by the energy infusion at SWS, as shown in the panel B with the pHFO shown as a dark mark image; the potential epilepsy center created can be seen at the (0, 0) mV sensory origin (SO) in the optical image in the panel C in FIG. 25. It paved a road for reentrant of pHFO and Aβ, and this nonsymptomatic stage was defined as "Stage One" for epilepsy or AD.

The second stage was under the conditions: the prosthesis made by the sensory biomarker CV data from 40-300 Hz was without Aβ, but the biomarker's CV data at 1 Hz was with Aβ, so it was same for the discharge energy pulses, at 0.25 Hz with Aβ, and pulses discharged at 40 Hz and 250 Hz without Aβ. It indicates Aβ only invades the neocortex, not entered the deep brain. It was found there is an epilepsy center at the DET peak location of 0 mV and the cross-point 0 mV, and it clearly self-synchronized with the brain network at the sensory location of the cross-point at 420 mV and the DET location at 0 mV at 250 Hz with a small amount of Aβ deposited, as shown in FIG. 26 for the symptomatic AD or epilepsy with short-term memory loss, and led to dysfunctional sensory. The circuitry flow surface was more bended and the direction was anti origin compared in FIG. 24 panel A, and FIG. 26 panel A has an indentified reentrant spot, and the energy sinking hole was the pHFO spot and was labeled in the panel B of FIG. 26. The CA1 sector has been identified as an extremely vulnerable spot to traumatic insult; however the explicit mechanism is unknown according to literature [63]. Using the invented device 2, the vulnerable spot was shown and shorn a light with the flow circuitry and conformation information to the researchers. One epilepsy center was labeled in the contour map as well as in the panel C, the light image map.

Figure 10:
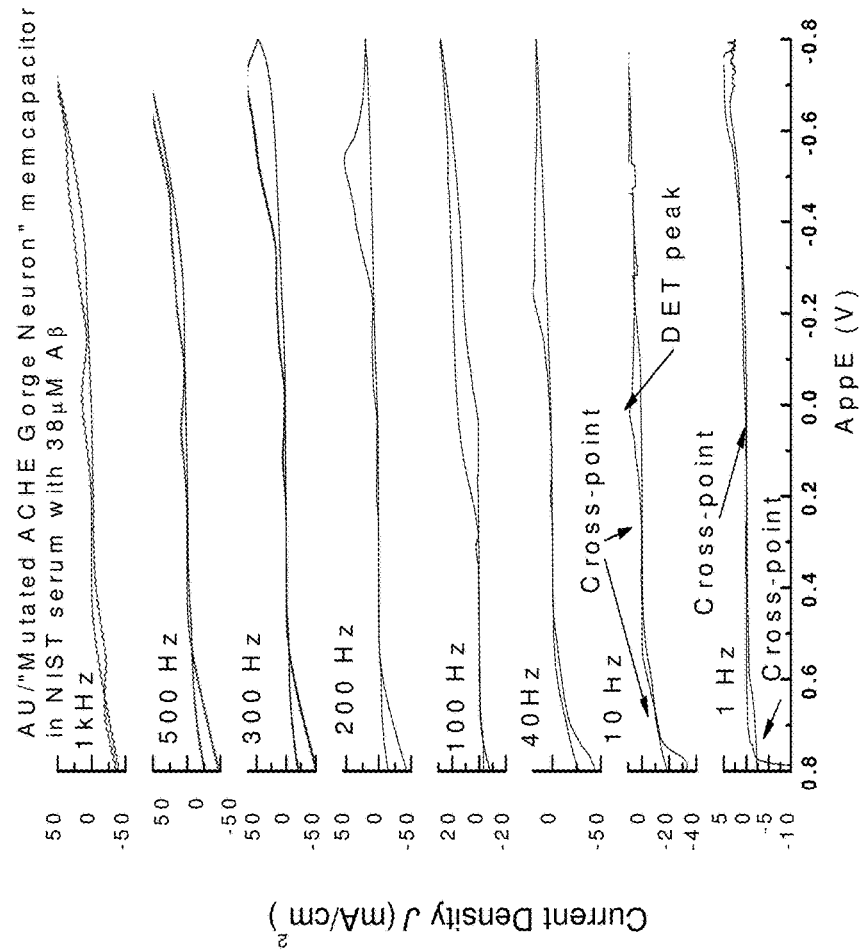
FIG. 10 depicts CV profiles with 38 μM Aβ of device 2 over scan frequencies 1 Hz to 1 kHz in NIST human serum.

The third stage was under the conditions: the discharge pulse energies infused in the matrix were under the similar conditions as in stage 2, but the sensory "prosthesis" matrix made from the CV data of sensory biomarkers used 2 cross-points and 2 $DET_{red}$ peaks at 1 and 10 Hz, respectively according to the CV curves in FIG. 10. This means Aβ is able to influence the formation of sensory biomarkers, hence the stage 3 AD or epilepsy has increased pHFO centers with larger Aβ depositions, therefore the prosthesis's original light intensity was greatly reduced. Numbers of pHFO as a "mutated reentrant center" were increased, and areas of Aβ depositions increased which led to a deep darkened brain image with the light intensity reduced by more than 90%, it means the volume of the hippocampus brain was reduced by 90% as shown in FIG. 27 panel A, B and C. This stage is the Aβ in deposition in neocortex, while the epilepsy is not in domination. Aβ formed new sensory biomarkers are important to notice that played a crucial role to be in control of the AD.

The "Epilepsy IV" is a "life threatening stage" in stage 4A and 4B parallel situations. The sensory "prosthesis" made from the CV data of sensory biomarkers used multiple $DET_{red}$ and multiple cross-points over 1-300 Hz with 38 μM Aβ. The manner of discharge pulses are same as stage 3, that discharge energy pulses at 0.25 Hz with 38 μM Aβ, and pulses discharged at 40 Hz and 300 Hz without Aβ. The Aβ's accumulation in cortex is no longer a predominate factor, rather than to transform the epilepsy as a dominate factor at hippocampus with an evidence of forming 4 epilepsy centers and 4 pHFO centers as shown in FIG. 28 panel B and C. The 3 pHFOs were in alignment at cross-point 0 mV and one of the pHFO was alignment at DET 0 mV forming a channel led to epilepsy synchronized over 40-300 Hz in the hippocampus. An "eye of tornado" in the center of the channel as a dark sport as seen due to the overheated epilepsy-causing the edema of hippocampus, which is in agreement with the clinical acute epilepsy stage reported with hyppocampus edema and hyper-intense initially, then late atrophies [64] as shown in the panel B of FIG. 28. The FIG. 28A shows the circuitry surface conformation as a standing beast and the synapse current flow direction consisted of three clock wise flow circles and one counter clock flow circle, and the flow circles in neocortex is perpendicular to that of the hippocampus that a "tornado" forming force was in place bearing destruction capability, as a fire vertex that is spontaneous and difficult to put off. We had identified this force as a toroid destruction force caused by the missing of the ACHE gorge linen through our experiment study [24]. The end stage AD patients who suffer symptoms of epilepsy, involunteering mussel contraction have matched the stage 4A. Stage 4B is same for the prosthesis building as for 4A, that all biomarkers' CV data obtained with Aβ over 1-300 Hz; but the energy infused entered the matrix by pulse discharge through the entire range of frequencies are with Aβ. FIG. 29 panel A shows the synapse circuitry with two anti clockwise circles of 1 to 4, and 4 to 7 forming surfaces almost paralleled to the neocortex, however at the reentrant point at number 7 at 40 Hz as the reentrant point that connected to a flow surface from number #7 to #13 which is perpendicular to the early formed circles. The synapse flows from 40 Hz at #7 to #13 at 300 Hz is in a manner of helix has given to the epilepsy a new level of fire vertex with the epilepsy center #1, #2 and #3 in 300 Hz in the hippocampus with severe edema and the two more epilepsy centers are mobile in 100-200 Hz. It is an agreement with the clinical observations that the epilepsy hurts the hippocampus more severe than to hurt the neocortex [64] as shown in the panels B and C in FIG. 29. FIG. 29 panel D depicts the colorful optical image of the progressing of the AD or epilepsy using neither a tracer nor a dye.

Example 14—Applications in Assessing Repairing of "Damaged Neuron" in "Hippocampus" by the Energy-Sensory Images The early treatment of 15 nM ACH at "Epilepsy or AD Stage 2" in NIST serum with spiked Aβ had received great results. The sensory prosthesis was modified under the conditions: at 1 Hz with 38 μM Aβ in human serum with 15 nM ACH, the biomarker CV data obtained at 10 and 40 Hz had 2 mM o-NPA treated the above mentioned serum containing ACH and Aβ; 100-300 Hz was serum only; the energy infused entered the data matrix from the discharge energy pulses: at 0.25 Hz and 40 Hz with ACH and Aβ; at 250 Hz was pure serum. FIG. 30 panel A showed the synapse flow circuitry was again in a flat "8-shape" and ACH presence at SWS had initiated a formation of HFO located at the origin (0, 0) mV and removed the pHFO spot as shown in the panel B of the contour plot, so the sensory prosthesis's light was restored and enlightened as shown in the panel C of the light image. The key of the recovery is established the hydrophobic linen at the reentrant gamma frequency (40 Hz had been identified is the weak spot in hippocampus) and ACH imitated right direction and conformation of synapse flow at SWS. However, at a late stage of 4A or 4B, even treated with the same procedures, the completely restoration is not possible as seen in FIG. 31 panel A, B and C for stage 4A and FIG. 32 panel A, B and C for stage 4B, respectively. Even the HFO was created by the treatment procedures, and the brain sensory prosthesis light intensity become great, but the numbers of the epilepsy centers did not completely erased, it still remains several. It is called "non curable". At an early stage treatment, it is much better.

Example 15—Quantitation of Re-Entrant

We had qualified the memory reentry and recursive using the energy-sensory image technology in above sections through HFOs. This section is to establish the quantitation of the reentrant events. Without Aβ, device 1 has the appropriate reentrant time frame to store-retrieve information for 18, 20, 26.6, 160-fold higher reentry energy sensitivity compared at 3.8, 76, 151 and 471 nM Aβ, respectively, and the desire for a low energy per bit consumption in pJ/bit/μm³ was in a reversed order as shown in Table 1. The results were calculated by a linear regression model. Support data are shown in FIG. 33. All results are less than 0.01 pJ/bit/μm³, that is the goal of 2020 [5] for chips in the slope column, except without Aβ, which is 0.1186 pJ/bit/μm³, and that is a magnitude advance over current reported performance [5].

TABLE 1

Information storage and retrieve sensitivity fitting by the linear least-squire equation between energy density vs. time (s) using device 1.

| Aβ nM | Slope Reentry Sensitivity (pJ/bit/μm³)/s | r | Top range Reentry pJ/bit/μm³ | Bottom range Reentry pJ/bit/μm³ |
|---|---|---|---|---|
| 0 | 0.11862 | 0.9994 | 0.4716 | 6.84E−6 |
| 3.8 | 0.0067 | 0.9999 | 0.02675 | 1.188E−4 |
| 76 | 0.00605 | 0.9918 | 0.02434 | 4.32E−6 |
| 151 | 0.00446 | 0.9926 | 0.01789 | 3.6E−6 |
| 471 | 7.56E−4 | 0.9143 | 0.00302 | 6.12E−7 |

Early non-symptomatic epilepsy was indentified and predicted by device 2 due to pHFO and large areas of Aβ re-depositions. Our data shown early CR dysfunction is not due to the entrance of Aβ for device 2, but the damaged ACHE gorge linen itself along with a synapse pulse discharge at SWS, which initiated a pHFO sport synchronized with the brain motif. Aβ played a heavy damage when pHFO occurred. We have identified the weak spot in the hippocampus that positively linked to epilepsy. Device 1 is more sensitive about Aβ damage in an early stage because of its HFO with higher reentrant energy sensitivity of 0.12 pj/bit/s/μm³ without Aβ compared with 13 aj/bit/s/μm³/nM over 3.8-471 nM range over 0.003-4 s. Device 1 reliably detected early CR dysfunction.

For Device 2, the results of linear regression of the volumetric energy density vs. time after 15 nM ACH applied in the 38 μM Aβ produced an equation of y=−0.075+9.89x, r=1.0 $S_{y/x}$=0.055, over 0.25-250 Hz, p<0.001, over the energy range from 39.5 μWHr/cm³ at 0.25 Hz to 3.76×10⁻³ μWHr/cm³ at 250 Hz. The memory at neocortex-hippocampus reached 30% of the strength of a healthy brain for the long-term memory [59].

TABLE 2

Information storage and retrieve sensitivity fitting by the linear least-squire equation between energy density vs. time (s) using device 2.

| ACH nM | Aβ μM | Slope Reentry Sensitivity (pJ/bit/μm³)/s | r | Top range Reentry pJ/bit/μm³ | Bottom range Reentry pJ/bit/μm³ |
|---|---|---|---|---|---|
| 0 | 0 | 0.0002 | 0.88 | 0.00079 | 4.0 × 10⁻⁷ |
| 0 | 38 | 0.000058 | 0.78 | 0.00088 | 5.3.0 × 10⁻⁷ |
| 15 | 38 | 0.0356 | 1.00 | 0.1422 | 1.35 × 10⁻⁵ |

REFERENCES

1. Indiveri G, Linares-Barranco B, Legenstein R et al., *Integration of nanoscale memristor synapses in neuromorphic computing architectures*, arxiv:1302:7007V1, 2013.
2. Chua. L O. *Memristor—The Missing Circuit Element*, IEEE Transactions on Circuit Theory, CT-18 (5): 507-519, 1971.
3. Chua, L O. *Resistance switching memories are memristors*. Applied Physics A 102 (4): 765-783, 2011.
4. *Artificial synapses could lead to advanced computer memory and machines that mimic biological brains*, HRL Laboratories, Mar. 23, 2012.
5. *Chips 2020, the frontier of nanoelectronics*, Editor B. Hoefflinger, Springer. 2012.
6. *Advances in neuromorphic memristor science and applications*, Editor Kozma R, Pino R E, Pazienza G E Springer Series in cognitive and neural systems, 2012.
7. Chen E T, Thornton J T, Ngatchou C, Duh S H, *Nanostructured Memristor Sensor Mimics Acetylcholinesterase (ACHE) Active Sites In The Gorge For fM Detection Of Acetylcholine*, NSTi-Nanotech, 2, 200-203, 2014.
8. www.iom.edu/sleep report
9. Slats D, Claassen J A H R, Verbeekb M M, Overeem S, *Reciprocal interactions between sleep, circadian rhythms and Alzheimer's disease: Focus on the role of hypocretin and melatonin*, Ageing Research Reviews 12, 188-200, 2013.
10. Yan J J el al., *Protection against β-amyloid peptide toxicity in vivo with long-term administration of folic acid*, British J of Pharmacology, 133, 89-96, 2001.
11. Toledo J B, Shaw L M, Trojanewski, *Plasma amyloid beta measurements, a desired but elusive Alzheimer's disease biomarker*, Alzheimer's Research and Therapy 5(8), doi: 10.1186/alzrt162, 2013.
12. Dobrawolka J A et al. *Diurnal patterns of soluble Aβ precursor proteins metabolites in the human central nervous system*, Plos One, 9(3), e89998, 2014.
13. Morley J E and Favi S A, *The role of amyloid-beta in the regulation of memory*, Biochemical Pharmacology, 88(4), 479-485, 2014.
14. Roh J H, Huang Y, Bero A W et al., *Disruption of sleep-wake cycle and Diurnalfluctuation of β-amyloid in mice with Alzheimer's disease pathology*, Science Translational Medicine 4, 150ra-122, 2012.
15. Duh S H, Thornton J T, Kissinger P T and Chen E T, *A Nanobiomimetic Neuronal Memcapacitor Serves as a Voltage Sensor and an Amperometry Sensor for Reagentless Direct Detection of Sub pM Soluble Amyloid-beta*, NSTi-NanoTech, in press, 2015.
16. Chen E T, Thornton J and Mulchi Jr C. *Mapping Circular Current for a Single Brain Cancer Cell's Spa-*

*tial-Temporal Orientations Based on a Memristor/Memcapacitor*, Sensors & Transducers, 183(12), 72-83, 2014.

17. Steffen G and Born J P, *Low acetylcholine during slow-wave sleep is critical for declarative memory consolidation*, PNAS, 101(7), 2140-2144, 2004.
18. Power A E, *Slow-wave sleep, acetylcholine, and memory consolidation*, PNAS, 101(7), 1795-1796C, 2004.
19. Edelman G M and Gaily J A, *Reentry: A key mechanism for integration of brain function*, Frontiers in Integrative Neuroscience, 2013. doi: 10.3389/fnint.2013.00063
20. Raffone A, Srinivasan N and Leeuwen C V, *Perceptual awareness and its neural basis: bridging experimental and theoretical paradigms*, Phil. Trans. R. Soc. B 369: 20130203. http://dx.doi.org/10.1098/rstb.2013.0203
21. Kauffman L H, *Self-reference and recursive forms*, J Social Biology Structure, 10, 53-72, 1987.
22. Chen E T, Thorten J, Ngatchou C, Duh S-H, Kissinger P T, *Nanostructured biomimetic pyruvate dehydrogenase complex (PDC) sensors selectively detect single brain cancer cell having the ability to mimic the "ATP Lid"*, NSTi-NanoTech 2, 107-110, 2013.
23. Chen E T and Thornton J, *Nanostructured Acetylcholinesterase (ACHE) Memristor/Memcapacitor Mimicks Brachyhypopomus Electric Fish's Signal-Cloaking Behavior*, NSTi-Cleantech, 3, 63-66, 2014.
24. Cabaret T et al., *Electro-grafted organic memristors: Properties and prospects for artificial neural networks based on STDP*, Nanotechnology (IEEE-NANO). IEEE 14th International Conference, p 599-504, 2014. 10.1109/NANO.2014.6968169
25. Martínez-Montes E, Valdés-Sosa P A, Miwakeichi F, et al., *Concurrent EEG/fMRI analysis by multiway Partial Least Squares*, Neuron Image, 22, 1023-1034, 2004.
26. Alvarado-Martinez R, Salgado-Puga K and Pena-Ortega F, *Amyloid-beta inhibits olfactory bulb activity and the bility to smell*, Plos One, 8(9),e5745, 2013.
27. Pena-Ortega F and Bernal-Pedraza R, *Amyloid-beta slows down sensory-induced hyppocampal oscillation*, International J of Peptides, 2012, 2012. http://dx.doi.org/10.1155/2012/236289
28. Ventra M D and Pershin Y V, *On the physical properties of memristive and memcapacitive and meminductive systems*, J of Physics D, arXiv: 1302.7063v2, 2013.
29. *Jasper's Basic Mechanisms of the Epilepsies*, fourth edition by Noebels J L, Voli M, Oxford Press Publisher, N Y, 2012.
30. Marshall L, Binder S, *Transcranial oscillatory stimulation to research on neural networks, an emphasizes on hippocampus-neocortical rhythms*, Frontiers in Human Neuroscience, 7(614), 1-6, 2013.
31. *The hippocampus book*, edited by Anderson P, Morris R, Amaral D, Bliss T and O'keefe J, Oxford University Press, 2007.
32. El-Kady M F, Strong V, Dubin S, Kaner R B, *Laser Scribing of High-Performance and Flexible Graphene-Based Electrochemical Capacitors, supplement materials*, Science 335, 1326, 2012.
33. Miller J R and Outlaw R A and Holloway B C, *Graphene double-layer capacitor with ac line-filtering performance*, Science, 329, 1637, 2010.
34. Pyka M and Cheng S, *Pattern Association and Consolidation Emerges from Connectivity Properties between Cortex and Hippocampus*, 9(1), e86016, 2014.
35. Chen E T and Pardue H L, *Analytical applications of catalytic properties of modified cyclodextrins*, Anal Chem, 65 (19), 2563-2567, 1993.
36. Chen E T, Thornton J T, Ngatchou C, Duh S H and Kissinger P T, *Nanostructured Biomimetic Pyruvate Dehydrogenase Complex (PDC) Sensors Selectively Detect Single Brain Cancer Cell Having The Ability To Mimic The "ATP Lid"*, NSTi-NanoTech (2), 107-110, 2013.
37. Sussman J L, Harel M, Frolow F, Oefner C, Goldman A, Toker L, Silman I, *Atomic structure of acetylcholinesterase from Torpedo californica: a prototypic acetylcholine-binding protein*. Science 253, 872-879, 1991;
38. Gilson M K. Straatsma T P, McCammon J A. Ripoll D R, Faerman C H, Silman I. Sussman J L, *Open "back door" in a molecular dynamics simulation of acetylcholinesterase*, Science 263, 1276-1278, 1994.
39. Silman I, Sussmana J L, *Acetylcholinesterase: How is structure related to function?* Chem Biol Interact. 175, 3-10, 2008.
40. Mira A, Yamashita S, Katakura Y, and Shimizu K. *In vitro neuroprotective activities of compounds from angelica shikokiana makino*, Molecules 20, 4813-4832, 2015.
41. Biolek D, Di Ventra M, Pershin Y V, *Reliable SPICE Simulations of Memristors, Memcapacitors and Meminductors*, Radioengineering 22 (4), 945-968, 2013.
42. Martinez-Rincon J and Pershin Y V, *Electron Devices. IEEE Transactions* 58 (6), 1809-1812, 2011.
43. Martinez-Rincon J, Ventra M D, Pershin Y V, *Solid-State Memcapacitive System with Negative and Diverging Capacitance Physical Review B*, 81(19), 195430-1-195430-7, 2010.
44. Pickett M D, Medeiros-Ribeiro G and Williams R S, A Nature Materials, DOI: 10.1038/NMAT3510, 2012.
45. Kozma R, Pino R E, Pazienza G E, *Advances in neuomorphic memristor science and applications*, Springer publisher, 2012.
46. Ventra M D, Pershin Y V, Nanotechnology 24, 255201, 2013.
47. Chen E T, Nanopore Array Structured Devices for Biosensing and Energy Storage, U.S. Pat. No. 8,641,876, Feb. 4, 2014.
48. Chen E T, Nanopore Structured Electrochemical Biosensor, U.S. Pat. No. 8,083,926, Dec. 27, 2011.
49. Chen E T, Apparatus and Methods for Making High Performance Fuel Cell, U.S. Pat. No. 8,632,925 issued by USPTO, Jan. 21, 2014.
50. Chen E T, Nanostructured Biomimetic Device with Contour Map of Multiple Variable Correlation Method to Visually Display the Cancer Progresses, US 20,140,178, 925, Jun. 26, 2014.
51. Chen E T, Nanobiomimetic Supercapacitors with High Rate High Energy Storage, US 20,140,104,751, Apr. 17, 2014.
52. Chen E T and Thornton J, Nanostructured Acetylcholinesterase (ACHE) Memristor/Memcapacitor Mimicks Brachyhypopomus Electric Fish's Signal-Cloaking Behavior, NSTi-Cleantech, 3, 63-66, 2014.
53. Yang J J, Strukov D B, and Stewart D R, *Memristive devices for computing*, Nature Nanotechnology, 8, 13-24, 2013.
54. El-Kady M F, Strong V, Dubin S, Kaner R B, Science 335, 1326, 2012.
55. Miller J R and Outlaw R A and Holloway B C, *Graphene double-layer capacitor with ac line-filtering performance*, Science, 329, 1637, 2010.
56. Duh S H, Thornton J T, Kissinger P T and Chen E T, NSTi-NanoTech, in press, 2015.

57. Zanini D et al., Biomedicine and Pharmacotherapy 66(4), 249-255, 2012.
58. Gauresh S, Chinmay K, Prashant S, Rupesh S, Kirti L. Sadhana S, Journal of Pharmacy and Bioallied Sciences, 7 (1), 32-36, 2015.
59. Chen E T, Thornton J T and Mulchi J C. *Nano-biomimetic Memcapacitor Memory Devices Identify Circadian Rhythm Dysfunction and Predict Early Signs of "Epilepsy" Using Reentrant Energy-Sensory Images*, NSTi-NanoTech, in press, 2015.
60. Schuff N, Woerner N et al., *MRI of hyppocampal volume loss in early Alzheimer's disease in relation to ApoE genotype and biomarkers*, Brain 132, 1067-1077, 2009.
61. Vijayakumar A, and Vijayakumar A, *Comparison of Hippocampal Volume in Dementia Subtypes*, Internationally Scholarly Research Notices (ISRN) Radiology, 174525/2013. http:/dx.doi.org/10.54021/2013/174524
62. *Brain circuitry and signaling in psychiatry: Basic science and clinical implications*, edited by Kaplan G B and Hammer R P, Amer Psychiatric Pub; 1st edition, 2002.
63. Davolio C C, Greenamy J T, *Selective vulnerability of the CA1 region of hippocampus of indirect excitotoxic effects of malonic acid*, Neuroscience Letter 192,29-332, 1995.
64. Bronen R A, *The status of status: seizures are bad for your brain's health*, The American Journal of Neuroradiology 21, 1782, 2000.
65. Delvecchio R M, Feghali B P P T, Shah D M, Ahuja R, *Transformer design principles with applications to core-form power transformers*, second edition, CRC Press, 2010.
66. McCarthy S et al., Electromagnetic system with no mutual inductance and an inductive gain, U.S. Pat. No. 8,427,805.

What is claimed is:

1. An electromagnetic mems-transformer comprises;
  (a) a first electrode with a first and a second array of a nanometer sized first toroid made by a self-assembling organic cross-linked copolymer conductive membrane;
  (b) a vertical solenoid inserted in a cavity of the first toroid made by a second type of toroid forming the second array with nano donut shaped cyclodextrin (CD), in the hollow cavity of the CDs contains different electronegativity functional groups that mimics the function of acetylcholinesterase (ACHE) and also mimics its cylindrical gorge;
  (c) an organic laminate agent o-nitrophenyl acetate (o-NPA) forms a linen forming cross-bars in the first cavities of the arrayed toroids that is perpendicular to the first and second toroid and leave nanometer space air gap between them;
  (d) injecting a sample fluid into the mems-transformer, that comprises a first and a second array toroid, upon applying a DC potential across two electrodes in a fluid medium for initiation of the mems-transformer, changing current flows in the bipolar toroids in an electron-relay circular form until reached to a s-s state at a nano-ampere level; when held a nano-ampere current for conducting spontaneous discharge pulses at a fixed data rate and time, the current induced an electromagnetic flux change with orders of magnitude higher output voltage produced compared with the initiation potential; upon scanning a potential at a defined potential range across the electrodes at a fixed scan rate, bi-hysteresis i-V curves were promoted for memory function based on an embedded on-off switch.

2. According to claim 1, wherein the copolymer is further comprised of one or more β-cyclodextrin (β-CD) molecules having at least one or more acetyl groups.

3. According to claim 1, wherein the vertical solenoid made by the second toroid is further comprised of a cross-linking reagent of polyethylene glycol diglycidyl ether (PEG).

4. According to claim 3, wherein a PEG is cross-linked with one or more second β-cyclodextrin molecules having at least one or more imidazolyl groups in the cavity of β-CD.

5. According to claim 4, wherein a PEG is cross-linked with one or more poly(4-vinylpyridine) (PVP) polymers.

6. According to claim 1, wherein a PEG has another cross-linking fashion with PVP and triacetyl-β-cyclodextrin (TCD) without having an imidazolyl group in the cavity.

7. According to claim 6, wherein the polymer wire winding forms a first toroid in the same direction as the second toroid.

8. According to claim 1, wherein the first and the second electrode are made of either gold or glassy carbon or platinum.

9. According to claim 1, wherein the mems-transformer is an electromagnetic sensor detecting magnetic flux change due to the mems-inductivity of the electron-relay circular current when an object communicated with the sensor.

10. According to claim 1, wherein the device membrane is free from metal or metal oxide substances.

11. According to claim 1, wherein the device membrane has nanometer air gaps between the cross-bars.

12. According to claim 11, wherein by adjusting the air gap, the concentration of o-NPA is adjusted leading to more or less mems-inductivity.

13. According to claim 1, wherein the device works in various media of aqueous solution, organic solvent of alcohol and or human biological specimens.

14. According to claim 1, wherein the device is a mems-inductor with varying inductance based on the change of the (Direct Electron Transfer) DET current in the first array toroids and induced a current in the second array of toroids in the presence of an applied voltage.

15. The use of a device according to claim 1, further including injecting a sample fluid into the mems-transformer, that comprises a first and a second array toroid, upon applying a DC voltage to the first electrode with a membrane and the second electrode without a membrane, separated by a medium, a changing current flows in the bipolar toroidal arrays in an electron-relay circular current fashion until reached to a s-s state in a nano-ampere level, then held the nano-ampere current for discharge pulses, therefore setting up an appropriate stepping time period in order to measure the voltage change under a fixed current; or setting up an appropriate fixed potential in order to measure the current change; and setting up a fixed data rate in order to monitor the signals in the presence of an analyte against a control in the medium is necessary; it induced orders of magnitude amplifications in output voltage or current compared with the device's initiation state; a solenoid in the center core winding promoted a hysteresis wave for changing flow direction based on the cross-bar on-off switch, that corresponding to a mems-capacitor, a mems-ristor and a mems-inductor connected in series and its function is of a Tank Circuit.

16. The use of a device according to claim 1, further including an Energy-Sensory Image output comprising five steps: (1) identify a "Sensory Biomarker" (2) at the biomarker potential locations enter a discharge pulse energy data into the DET peak potential location in the "y" data column, and enter data at its spatial location of the cross-point in the "x" column, then enter a scan frequency data in the "z" column; (3) Convert the xyz columns to a random correlative gridding matrix; (4) highlight the matrix and convert the matrix (5) plot the 3D energy-sensory interactive dynamic synapse map; contour map and the optical image, respectively.

17. According to claim 16, wherein the devices direct detects reentry energy change highly sensitive in 13 aj/bit/s/$\mu m^3$/nM of Amyloid-$\beta$ (A$\beta$) over 3.8-471 nM range with the time range of 0.003-4 s.

18. According to claim 1, wherein the device is a memory device with a baseline information reentry sensitivity of 0.1 pj/bit/$\mu m^3$ over an interval 0.003-4 s.

19. According to claim 16, wherein the method can identify the presence of at least one or more pathological high frequency oscillation.

20. According to claim 16, wherein the method has a broadband of energy density change between 0.5 to 6.1× $10^{-7}$ pJ/bit/$\mu m^3$.

21. According to claim 16, wherein the memory device detects neuronal network circuitry integrity without using a tracer or dye.

* * * * *